US006860147B2

(12) United States Patent
Gunter et al.

(10) Patent No.: US 6,860,147 B2
(45) Date of Patent: Mar. 1, 2005

(54) PROCESS FOR PREDICTING POROSITY AND PERMEABILITY OF A COAL BED

(75) Inventors: William Daniel Gunter, Edmonton (CA); Matthew John Mavor, Park City, UT (US)

(73) Assignee: Alberta Research Council Inc., Edmonton (CA)

(*) Notice: Subject to any disclaimer, the term of this patent is extended or adjusted under 35 U.S.C. 154(b) by 167 days.

(21) Appl. No.: 10/261,201

(22) Filed: Sep. 30, 2002

(65) Prior Publication Data

US 2004/0060351 A1 Apr. 1, 2004

(51) Int. Cl.[7] .............................................. E21B 49/00
(52) U.S. Cl. ............................ 73/152.05; 73/152.05; 73/152.11; 73/152.02; 166/263; 166/266; 166/268; 166/280.1; 166/305.1; 166/253; 166/267; 166/402
(58) Field of Search ........................ 73/152.05, 152.11, 73/152.02; 166/263, 268, 266, 280.1, 305.1, 253, 267, 402

(56) References Cited

U.S. PATENT DOCUMENTS

| | | | |
|---|---|---|---|
| 5,099,921 A | 3/1992 | Puri et al. | |
| 5,501,273 A | 3/1996 | Puri | |
| 6,412,559 B1 | 7/2002 | Gunter et al. | |

OTHER PUBLICATIONS

Arri et al. "Modeling Coalbed Methane Production with Binary Gas Sorption" SPE 24363; 1992.
Brill et al. "Multiphase Flow in Wells" Monograph 17, Henry L. Doherty Series, Society of Petroleum Engineers; 1999.
Chaback et al. "Sorption Irreversibilities and Mixture Compositional Behavior During Enhanced Coal Bed Methane Recovery Processes" SPE 35622; 1996.
Earlougher *Advances in Well Test Analysis* Society of Petroleum Engineers of AIME; New York, p. 203–204; 1977.
Gash "Measurement of 'Rock Properties' in Coal for Coalbed Methane Production" SPE 22909; 1991.

(List continued on next page.)

*Primary Examiner*—Hezron Williams
*Assistant Examiner*—André K. Jackson
(74) *Attorney, Agent, or Firm*—Kurt D. Van Tassel; Deborah G. VandenHoff; Van Tassel & Associates

(57) ABSTRACT

A method for predicting the secondary porosity system (SPS) porosity, and thereby permeability, of a coal bed involves determining an initial condition in the coal bed, including an initial SPS pressure and an initial sorbed gas composition, determining a pressure strain effect due to increasing the SPS pressure to a value greater than the initial SPS pressure, and determining a sorption strain effect due to changes in the sorbed gas composition resulting from decreasing the methane content and increasing the content of a stronger adsorbing fluid (SAG) relative to the initial sorbed gas composition. Preferably, the method uses data from test injections of water and/or a weaker adsorbing fluid (WAG) and a SAG. The data is used in the inventors' model to compute a SPS porosity and an absolute permeability at a reference SPS pressure and a reference sorbed gas composition. Preferably, the reference pressure is atmospheric pressure. The inventors' model accounts for both dynamic pressure strain and dynamic multicomponent sorption strain effects. As a result, a calibrated model can be produced for the coal bed for predicting the coal bed's SPS porosity, and thereby permeability, as a function of a pre-selected injection or production fluid's composition and/or SPS pressure conditions.

60 Claims, 7 Drawing Sheets

OTHER PUBLICATIONS

Gash et al. "The Effects of Cleat Orientation and Confining Measurement on Cleat Porosity, Permeability and Relative Permeability in Coal," Paper 9321, *Proceedings of the 1993 International Coalbed Methane Symposium* The University of Alabama/Tuscaloosa; May 17–21; 1993.

Gidley et al., *Recent Advances in Hydraulic Fracturing*; Monograph 12, Society of Petroleum Engineers; p. 225; 1989.

Gray "Reservoir Engineering in Coal Seams: Part 1—The Physical Process of Gas Storage and Movement in Coal Seams" SPE 12514; 1987.

Greaves et al. "Multi–Component Gas Adsorption–Desorption Behavior of Coal" Paper 9353, *Proceedings of the 1993 International Coalbed Methane Symposium* The University of Alabama/Tuscaloosa; May 17–21: 1993.

Harpalani et al. "Influence of Matrix Shrinkage and Compressibility on Gas Production from Coalbed Methane Reservoirs" SPE 20729; 1990.

Harpalani et al. "Gas Slippage and Matrix Shrinkage Effects on Coal Permeability" Paper 9325, *Proceedings of the 1993 International Coalbed Methane Symposium* The University of Alabama/Tuscaloosa; May 17–21; 1993.

Huber, NIST Thermophysical Properties of Hydrocarbon Mixtures, NIST Standard Reference Database 4, Standard Reference Data, National Institute of Standards and Technology, Gaithersburg, MD; 1999.

Johnson et al. "Calculation of Relative Permeability from Displacement Experiments" *Trans. AIME* 216:370–372; 1959.

Levine "Model Study of the Influence of Matrix Shrinkage on Absolute Permeability of Coal bed Reservoirs," Gayer, R. and Harris, I. Eds., *Coalbed Methane and Coal Geology* Geological Society Special Publication No. 109, The Geological Society, London, p. 197–212; 1996.

Mavor, M.J. et al. "Measurement and Evaluation of Coal Sorption Isotherm Data," Paper SPE 20728, 65th Annual Technical Conference of the Society of Petroleum Engineers, New Orleans, Louisiana, Sep. 23–26; 1990.

Mavor, M. and Saulsberry, J. "Testing Coalbed Methane Wells" in *A Guide to Coalbed Methane Reservoir Engineering* GRI Report No. GRI–94/0397, Chapter 5; Mar. 1996.

Mavor, M. et al. "Coalbed Reservoir Gas–In–Place Analysis" GRI Report No. GRI–97/0263, p. 3.1–3.20; Nov., 1997.

Mavor et al. "Increasing Coal Absolute Permeability in the San Juan Basin Fruitland Formation" SPE 39105; 1998.

Palmer et al. "How Permeability Depends on Stress and Pore Pressure in Coalbeds: A New Model" SPE 36737; 1996.

Palmer et al. "How Permeability Depends on Stress and Pore Pressure in Coalbeds: A New Model" SPE 52607; 1998.

Puri et al. "Measurement of Stress Dependent Permeability in Coals and its Influence on Coalbed Methane Production" Paper 9142, *Proceedings of the 1991 Coalbed Methane Symposium*, The University of Alabama/Tuscaloosa; May 13–16, 1991.

Puri et al. "A Micro–Pilot Approach to Coalbed Methane Reservoir Assessment" Paper 9556, *Intergas '95* The University of Alabama/Tuscaloosa; May 15–19; 1995.

Seidle et al., "Application of Matchstick Geometry to Stress Dependent Permeability in Coals" SPE 24361; 1992.

Shu, et al. "Estimation of In–Situ Coal Permeability from Slug and Packer Tests" SPE 28664; 1994.

Stevens et al. "Enhanced Coalbed Methane Recovery Using $CO_2$ Injection: Worldwide Resource and $CO_2$ Sequestration Potential" SPE 48881; 1998.

Stevenson et al. "Adsorption/Desorption of Multicomponent Gas Mixtures at In–Seam Conditions" SPE 23026; 1991.

Whitson et al. "Phase Behavior," Monograph 20, Henry L. Doherty Series, Society of Petroleum Engineers, Ch. 3; 2000.

Zheng et al. "Static and Dynamic Testing of Coal Specimens" Paper 9120, 1991 Society of Core Analysts, 5th Annual Technical Conference; Aug. 1991.

PROCESS FOR PREDICTING POROSITY AND PERMEABILITY OF A COAL BED

FIELD OF THE INVENTION

The present invention relates to the field of coalbed methane and, in particular, to a method for predicting a coal bed's porosity, and thereby a coal bed's permeability.

BACKGROUND OF THE INVENTION

Coalbed methane (CBM) has become a significant component of U.S. natural gas supplies. CBM production increased to 2.9 Bscf/day of gas supply in 1997, accounting for about 6% of total U.S. natural gas production (Stevens et al., "Enhanced Coalbed Methane Recovery using $CO_2$ Injection: Worldwide Resource and $CO_2$ Sequestration Potential" SPE 48881; 1998).

Most CBM reservoirs are produced under primary recovery methods, i.e., without secondary recovery methods involving injection of recovery-enhancing fluids. The proportion of original gas-in-place that can be recovered is dependent on reservoir properties, in particular, the absolute permeability of the coal bed. In high permeability reservoirs (>20 millidarcy (md)), recovery can theoretically be up to 80% of original gas-in-place. CBM recovery in moderate permeability reservoirs (5 to 20 md) can range from 50 to 70%, while recovery in low permeability reservoirs ($\leq$5 md) can range from 10 to 50%. CBM recovery is also dependent on production economics. Presently, low permeability reservoirs are unlikely to produce CBM at commercial rates without some form of enhanced recovery. Moreover, the volume of CBM remaining after primary production, especially in moderate and low permeability reservoirs, is significant. For example, it is estimated that primary production in developed areas of the San Juan Basin alone, which are generally high permeability reservoirs, may leave behind as much as 10 Tscf of natural gas in areas with depleted coal beds (Stevens et al., ibid).

New technologies have been proposed for enhanced coalbed methane recovery (ECBM) to recover a larger fraction of CBM in place. The two principal variants of ECBM are (1) inert gas stripping by injecting nitrogen ($N_2$), which is a weaker adsorbing gas (WAG) than methane ($CH_4$), and (2) displacement desorption by injecting carbon dioxide ($CO_2$), a stronger adsorbing gas (SAG) than $CH_4$.

Generally, as an injected WAG enters a coal bed through a wellbore, the partial pressure observed for CBM in the vicinity of the wellbore is substantially reduced. Most significantly, it is believed that the CBM partial pressure in the wellbore vicinity can be reduced to particularly low levels as a WAG is injected. Consequently, it is believed that as the CBM partial pressure is reduced, the CBM desorption rate from coal increases dramatically and the CBM is swept substantially through the coal bed in a mixture with the WAG to a production well. The production rate of the WAG and CBM is controlled by the total pressure in the formation, which is maintained as high as possible by injection during this process. Some WAG is sorbed into the coal, but there is a net reduction in the total gas (i.e., CBM and WAG) content of the coal.

By contrast, generally, as a gas that is more strongly adsorbing than $CH_4$ is injected into the coal bed, it is believed to be preferentially adsorbed into the coal. Since the SAGs are generally not produced, this process works well for both ECBM recovery and sequestration of SAGs, such as $CO_2$ or hydrogen sulfide ($H_2S$). And there is a net increase in the total gas (i.e., SAG and CBM) content of the coal. Also, the SAG is typically trapped in-situ and is not produced unless the injected SAG front reaches the production well (i.e., breakthrough). At breakthrough, this type of SAG injection and CBM displacement process would be terminated.

Thus, a secondary benefit associated with a SAG injection/CBM displacement process, such as a $CO_2$-ECBM process, is that it can sequester large volumes of $CO_2$. There is an increasing concern that some gaseous effluent streams from industrial processes may cause environmental problems, and, as a result, these streams should not be released into the atmosphere. $CO_2$ is a constituent of many gaseous effluent streams released from industrial processes and whose release into the atmosphere is causing increasing concern. Should global restrictions on $CO_2$ emissions be promulgated, $CO_2$-ECBM could be one of the few profitable technologies for sequestering $CO_2$. For instance, tradable credits for $CO_2$ sequestration could dramatically improve $CO_2$-ECBM economics over current performance levels.

Some global warming proponents relate excess nitrous oxide ($N_2O$), as well as $CO_2$, emissions to climatological change. Also, nitrogen oxide ($NO_x$) emissions, such as nitric oxide (NO) or nitrogen dioxide ($NO_2$), in sufficient concentration, can be toxic to health and the environment. Additionally, sulfur oxide ($SO_x$) emissions, in sufficient concentration, can contribute to the production of "acid rain," which can have a detrimental effect on various plant and aquatic life.

Thus, it is possible that many or all of these gases could become more stringently regulated, at least in certain market-developed countries or regions, such as the United States, Canada, Japan and Europe. Consequently, this prospect of increasing regulatory stringency for some or all gaseous emissions can hamper many industries because the combustion of virtually any hydrocarbon fuel with air produces an effluent containing $CO_2$, $N_2$, and gaseous combustion products.

For instance, various countries, including, among others, France, Germany, the United Kingdom, Canada and Japan have agreed to seek internal approval and adoption, within their respective jurisdictions, of the Kyoto Protocol. The Kyoto Protocol ensued from the United Nations Framework Convention on Climate Change, held in December 1997 at Kyoto, Japan. Under the Kyoto Protocol, each participant agreed in principle to "implement and/or further elaborate policies and measures in accordance with its national circumstances" to, among other things, enhance energy efficiency and protect reservoirs of certain atmospheric gases not controlled by the Montreal Protocol (e.g., $CO_2$). Generally, the Kyoto Protocol addressed emissions of greenhouse gases, including $CO_2$, $CH_4$, $N_2O$, hydrofluorocarbons (HFCs), perfluorocarbons (PFCs), and sulfur hexafluoride ($SF_6$). While the United States and Australia have elected not to follow the Kyoto Protocol, they tend to address greenhouse gas emissions with national programs.

In addition to being a hydrocarbon combustion product, $CO_2$ can be produced by natural processes and released to the environment during a non-combustion process. For example, $CO_2$ is produced by thermal and biogenic processes, which are believed to form hydrocarbons such as oil, natural gas, or coal. $CO_2$ often is recovered with these hydrocarbons and released to the atmosphere by various post-production steps.

The increasing concern over the atmospheric release of $CO_2$ and other undesired gas-emission compounds demands a method(s) for disposing of the compounds, once collected.

As discussed above, various ECBM recovery and sequestration processes have been disclosed. For example, U.S. Pat. No. 6,412,559 (Gunter, Mavor and Law, Jul. 2, 2002) describes a process for recovering $CH_4$ from a coal bed and/or sequestering a SAG in a coal bed by cyclic SAG injection with intervening shut-in periods.

In order to make injection and/or production processes more efficient, it is desirable to determine the coal bed's porosity, absolute permeability and effective permeability to gas and water for a given injection pressure, production pressure, injected gas composition and/or produced gas composition. These data would then be used to design, monitor, and improve the efficiency of ECBM and/or sequestration processes. These data can also be used to design, monitor and improve the efficiency of primary production processes.

Coal is characterized by two distinct porosity systems, discussed more fully below: a primary porosity system and a secondary porosity system ("SPS"). The primary porosity system contains the vast majority of the gas-in-place and the sequestration capacity, while the SPS provides the conduit for mass transfer between wells and the primary porosity system.

Primary porosity system gas storage is dominated by adsorption phenomena because of the high surface area to volume ratio caused by very small pore spaces within the organic material and the close proximity of gas molecules to molecules within solid materials. The gas and solid molecules attract each other due to weak intermolecular forces known as Van der Waals forces. Due to attraction to the solid, gas molecules are packed closer together than expected from the pressure and temperature conditions. The equivalent density of the molecules in the sorbed state is similar to the density of the molecules in a liquid state. In coal beds, the primary porosity system is relatively impermeable due to the small pore sizes. Mass transfer for each gas molecular species is dominated by diffusion that is driven by the concentration gradient (i.e., change in concentration along a flow path divided by the length of the flow path) for each molecular species.

Commercially productive CBM reservoirs contain a well-developed SPS. Without natural fractures, commercial production from CBM reservoirs would not be possible due to the low permeability of the primary porosity system. Flow through the SPS is due to pressure gradients through the fracture system towards production wells.

Gray ("Reservoir Engineering in Coal Seams: Part 1—The Physical Process of Gas Storage and Movement in Coal Seams" SPE 12514, 1987) recognized that coal permeability changes during production due to (1) phase relative permeability effects (i.e., degree of saturation affects gas and water relative permeabilities) and (2) changes in effective stress within the coal seam. Generally, Gray observed that permeability is a function of effective stress within the coal seam. So, when the coal matrix shrinks with gas desorption, a concomitant decrease in effective stress leads to increased permeability. On the other hand, when coal bed cleats close with reduced fluid pressure, a concomitant increase in effective stress leads to decreased permeability. More specifically then, Gray teaches that permeability decreases when fluid pressure is reduced (i.e., coal bed cleats close). On the other hand, he observes an opposing effect where permeability is increased when coal shrinkage occurs with gas desorption.

Later, Stevenson et al. ("Adsorption/Desorption of Multicomponent Gas Mixtures at In-Seam Conditions" SPE 23026, 1991) produced adsorption isotherms for binary and ternary mixtures of $CO_2$, $CH_4$ and/or $N_2$. The adsorption isotherms showed that equilibrium gas (free gas) and adsorbate phase (sorbed gas) compositions differ considerably. Accordingly, Stevenson et al. teach that the total amount of gas adsorbed strongly depends on a gas mixture's composition and the system pressure.

And Arri et al. ("Modeling Coalbed Methane Production with Binary Gas Sorption" SPE 24363, 1992) described multi-component gas sorption using extended Langmuir isotherms as the basis for equilibrium between free and sorbed gas.

In the mid-1990's, those skilled in the art recognized that a significant feature of coal is its ability to sorb substances, including gases and stimulation chemicals. Upon sorption, the coal matrix swells and closes natural fractures, thereby reducing natural fracture permeability. Likewise, when a gas that is more weakly adsorbing than the in-situ gas is injected into the formation, the coal matrix will shrink, as weaker adsorbing fluid displaces the stronger adsorbing fluid from the coal matrix. Consequently, matrix shrinkage and swelling affect the coal bed's SPS porosity, absolute permeability and effective permeability to gas and water.

However, coal beds are most frequently heterogeneous and may exhibit significant anisotropy in both the vertical and horizontal directions. Also, coal is often found in layers separated by shale or sandstone. Therefore, core samples frequently fail to provide reliable estimates of a coal bed's in-situ SPS porosity or permeability. Likewise, pressure fall-off tests on their own typically yield insufficient information to sufficiently characterize a coal bed.

Accordingly, those skilled in the art have endeavored to produce a model for calculating SPS porosity and/or permeability. As an example, Levine developed a rock mechanics model to evaluate the effect of matrix shrinkage on fracture aperture width and absolute permeability as fluid pressure declines during primary CBM production ("Model Study of the Influence of Matrix Shrinkage on Absolute Permeability of Coal bed Reservoirs," Gayer, R. and Harris, I. eds., *Coalbed Methane and Coal Geology* Geological Society Special Publication No. 109, The Geological Society, London, pg. 197–212; 1996).

Levine recognized that absolute permeability could increase during primary production due to coal matrix shrinkage resulting from CBM desorption. But, citing Gray (ibid), Levine also recognized that, without matrix shrinkage, fractures could be sealed due to increasing pore volume compressibility with decreasing fluid pressure. Levine's model covered the relationship between gas desorption strain and fluid pressure decrease during CBM production. More specifically, Levine's CBM production model assumed a curvi-linear relationship between sorption strain and pressure during production. The model also used the Langmuir isotherm model for determining $CH_4$ and $CO_2$ data. Fracture width changes during primary production were modeled by Levine using five relationships:

$$\frac{d\varepsilon}{dp} = \frac{(\varepsilon_{max} \cdot P_{50})}{(P_{50} + P)^2}$$

$$k = \frac{(1.013 \times 10^9) \cdot b^3}{12 \cdot s}$$

$$\varepsilon_p = \frac{1}{E} \cdot (1 - 2v) \cdot \Delta P_f$$

$$\epsilon_s = M_s \cdot \Delta P_f$$

$$b_2 = b_1 + \epsilon_p \cdot s + \epsilon_s \cdot s$$

where
$\epsilon_{max}$ theoretical maximum strain at infinite pressure
$P_{50}$ pressure at 50% of maximum strain
P pressure
k permeability
b fracture width
s fracture spacing
$\epsilon_p$ fracture closure strain due to pressure change
E Young's modulus
v Poisson's ratio
$P_f$ pressure of fluids residing within coal
$\epsilon_s$ matrix shrinkage coefficient
$M_s$ matrix shrinkage coefficient
$b_2$ new fracture width
$b_1$ previous fracture width Levine selected "base case" and ranges of values for $b_1$, E, v, s, $\epsilon_{max}$ and $P_{50}$ and conducted parameter sensitivity analyses to show the effect of each variable. In each case, one of the six variables was changed while the remaining variables were held constant at the "base case" value. Although Levine acknowledges that there are interrelationships between the variables, there is no suggestion on how to account for the interrelationships. For example, Levine's sensitivity analysis showed that "permeability should increase more for coals with a higher Young's modulus; however, coals with a higher Young's modulus will tend to have a correspondingly lower matrix shrinkage coefficient as well and would probably actually exhibit a smaller increase in permeability." (Levine, p. 211)

Although Levine recognized parameter sensitivity in predicting permeability, including the sorption effect of $CO_2$ over CBM, he did not provide guidance on how to use each equation to predict a specific absolute permeability value for a specific reservoir condition. Levine's analysis also did not account for effects by or on injection processes. Accordingly, Levine's model was limited to primary production cases.

Recognizing some of the limitations of Levine's model, Palmer and Mansoori ("How Permeability Depends on Stress and Pore Pressure in Coalbeds: A New Model" SPE 36737; 1996 and SPE 52607; 1998) developed a theoretical model for calculating pore volume compressibility and permeability, during primary production, as a function of effective stress and matrix shrinkage. The theoretical model was intended to be more rigorous than the Levine model. The Palmer & Mansoori Model ("P&M Model") is presented below:

$$\frac{\phi}{\phi_0} = 1 + \frac{c_m}{\phi_0}(P - P_0) + \frac{c_0}{\phi_0}\left(\frac{K}{M} - 1\right) \cdot \left(\frac{bP}{1+bP} - \frac{bP_0}{1+bP_0}\right) \quad \text{(P \& M Model)}$$

where
$\phi$ porosity
$\phi_0$ porosity at original reservoir pressure
P reservoir pressure
$P_0$ original reservoir pressure
$c_m$ matrix compressibility, psi$^{-1}$
$c_0$, b parameters of Langmuir curve match to volumetric strain change due to matrix shrinkage
K bulk modulus
M constrained axial modulus But again the P&M Model was limited to predicting strain effects during primary production, without accounting for strain effects arising with gas injection or changes in gas composition. Palmer & Mansoori also identified the following relationship between permeability and porosity:

$$\frac{k}{k_0} = \left(\frac{\phi}{\phi_0}\right)^3$$

where
k permeability
$k_0$ virgin permeability

For convenience, hereinafter, we will refer to the portion of any model that accounts for porosity changes arising from pressure changes as pressure strain. Meanwhile, we will refer to the portion of the model that accounts for porosity changes arising from gas content changes as sorption strain.

Mavor et al. ("Increasing Coal Absolute Permeability in the San Juan Basin Fruitland Formation" SPE 39105; 1998) used the P&M Model to match the pressure and production behavior of three wells completed in Fruitland Formation coal seams in the San Juan Basin of Colorado. Primary CBM production resulted in coal seam permeability increases of 2.1 to 7.1 times the original permeability. Well tests were conducted in three wells early in the life of the well and later after significant depletion had occurred. The P&M Model was calibrated with the data from one well. The calibrated model was then used to compute the expected permeability ratio as a function of the pressure ratio. The computed relationship matched the results for the other two wells without additional changes. This analysis confirmed that the P&M Model was applicable to a primary CBM production and that the cubed power of the porosity ratio used to quantify the relationship between coal bed permeability and SPS porosity was correct.

The P&M Model accounts for changes in SPS porosity when pressure is reduced and when the coal matrix shrinks as the volume of gas sorbed into the coal matrix declines during production.

However, while the P&M Model accounts for coal matrix shrinkage, it is only applicable for a constant (i.e., static) gas composition. Moreover, the P&M Model is used to predict how permeability changes as pressure is decreased in drawdown, but not during injection. According to Palmer & Mansoori, "During drawdown of a reservoir by primary production, effective stress increases and permeability decreases due to cleat compression. However in coalbeds, drawdown leads to desorption of methane, and this is accompanied by matrix shrinkage which opens the cleats and leads to permeability increase. The two effects of cleat compression and matrix shrinkage act in opposite directions on permeability."

Accordingly, the P&M Model accounts only for changes in permeability and porosity during production, in particular during primary production. Because primary production does not involve injecting other gases, as in the case of ECBM recovery techniques, the produced gas composition is relatively constant until late in the life of a reservoir. And because the P&M Model assumes a constant gas composition, it is applicable only to production of original in-situ gas composition.

However, in ECBM recovery and/or fluid sequestration projects, the produced and/or injected gas compositions are dramatically different from the original in-situ composition. Such changes also affect the strain parameters dramatically. Accordingly, the P&M Model is not useful for predicting permeability or porosity changes in ECBM or fluid sequestration projects where gas other than original in-situ CBM is produced and/or injected into the coal bed. Also, the P&M Model uses initial coal bed reservoir properties as a reference point for determining the extent of change in reservoir permeability. However, after a fluid is injected or produced, the reservoir properties at the initial reservoir pressure have changed even if the reservoir pressure is substantially the same. Accordingly, the P&M Model becomes less effective, if not inapplicable, for predicting changes in permeability or porosity due to fluid injection or production with changing gas composition. These same disadvantages also apply to the less rigorous Levine model.

As an alternative approach to determining reservoir permeability, among other reservoir properties, such as CBM recovery rate and % CBM that can be economically recovered, Puri in U.S. Pat. No. 5,501,273 (Mar. 26, 1996) and a 1995 conference paper by Puri et al. ("A Micro-Pilot Approach to Coalbed Methane Reservoir Assessment," *Intergas '95 Proceedings*, University of Alabama/Tuscaloosa, pp. 265–274, May 15–19, 1995) describes a method using field data obtained from an injection flow-back test, which data, in turn, is used in a numerical reservoir simulator, along with injection data and any prior primary production data, to model the coal bed reservoir. More specifically, Puri's method is particularly suited for predicting CBM recovery rate and % CBM recovered in an ECBM recovery process. Meanwhile, the injection/flow-back test involves injecting a gaseous desorbing fluid containing at least 50% (vol.) $N_2$ into a formation. Injection rate data is collected during the injection step. The wellbore is then shut-in and the pressure response is measured. In a subsequent flow-back step, at least a portion of the injected fluid is produced, while production rate data and produced fluid composition data are obtained. Then, the collected field data is used in conjunction with reservoir modeling techniques, preferably by history matching with a numerical reservoir simulator for modeling the formation so ECBM recovery characteristics can be determined.

Puri teaches that the injection rate increase obtained for a given increase in injection pressure is dependent on the stress dependent permeability relationship exhibited by the formation. As defined by Puri, the stress-dependent permeability relationship describes the change in the effective permeability that occurs in the formation as the pore pressure changes. Puri further teaches that as injection pressure increases, pore pressure increases, which, in turn, causes the effective permeability of the formation to increase. Accordingly, Puri considers only changes in permeability arising from fluid pressure changes, such as a drop in fluid pressure that leads to cleat closure, and hence, reduced permeability for the SPS. But Puri fails to account for coal matrix shrinkage or swelling arising from the effects of different gases on the coal matrix.

For instance, the relationship between the effective permeability ratio, $K_f/K_i$, and pore pressure is illustrated in Puri's FIG. 1, (U.S. Pat. No. 5,501,273) which compares a theoretical relationship based on laboratory data (curve 25), history matching coal seam behavior before and during air injection (curve 27) and history matching coal seam behavior during flow-back after air injection (curve 29).

In fact, in 1991, Puri et al. published the theoretical relationship between $K_f$ and $K_i$, which was later re-introduced in FIG. 1 of U.S. Pat. No. 5,501,273 as curve 25 (see "Measurement of Stress Dependent Permeability in Coals and its Influence on Coalbed Methane Production" Paper 9142 *Proceedings of the* 1991 *Coalbed Methane Symposium*, University of Alabama/Tuscaloosa; May 13–16, 1991). The theoretical relationship is based on absolute permeability measurements performed on a coal sample maintained under uniaxial strain conditions to simulate an overburden with constant axial stress. The testing avoided relative permeability effects, as the coal sample was saturated with brine and then depleted of brine while maintaining a constant axial confining stress.

But, since the coal sample contained no gas, the theoretical relationship cannot account for changes in permeability arising from gas content changes. In fact, when comparing the history-matched and theoretical $K_f/K_i$ relationships in FIG. 1 of his patent, Puri stated that "The discrepancy between theoretical curve 25 and fitted curve 27 during the pre-injection production and air injection period is believed to be a result of the simulator not accounting for the relative permeability relationship exhibited over time by the formation." (col. 21:4–8). Therefore, Puri fails to recognize the importance of, and thereby account for, a sorption strain component to better predict the coal bed's permeability in view of different types of injection gas compositions.

Moreover, Puri suggests that his method for determining ECBM recovery characteristics using a test gas containing at least 50% (vol.) $N_2$ could equally be applied to ECBM recovery techniques using an injected gaseous desorbing fluid containing either at least 50% (vol.) $N_2$ or at least 50% (vol.) $CO_2$. And yet Puri does not account for matrix shrinkage or swelling due to gas composition. However, as discussed more fully below, $N_2$ and $CO_2$ have quite different effects on a coal bed's permeability and porosity.

Accordingly, there is a need for a method for predicting a coal bed's SPS porosity and/or permeability for different injected and/or produced fluid compositions at different injection and/or production pressures. Moreover, there is a need for a model that can be applied to injection and/or production processes. More particularly, there is a need for a method for predicting a coal bed's SPS porosity and/or permeability for better assessing the economics and efficiency of both CBM production and/or sequestration projects.

SUMMARY OF THE INVENTION

According to the present invention, there is provided a method for producing a calculated secondary porosity system (SPS) porosity value in a coal bed, comprising:

(a) determining an initial condition in the coal bed, including an initial SPS pressure and an initial sorbed gas composition having an initial $CH_4$ content;

(b) determining a pressure strain effect on the coal bed due to increasing the SPS pressure to a value greater than the initial SPS pressure;

(c) determining a sorption strain effect on the coal bed due to changes in the sorbed gas composition resulting from decreasing the $CH_4$ content and increasing the content of a SAG relative to the initial sorbed gas composition;

(d) selecting a reference SPS pressure and a reference sorbed gas composition;

(e) correlating the initial condition, the pressure strain effect and the sorption strain effect in a quantitative relationship to determine:

(i) a reference SPS porosity,
(ii) a reference absolute permeability, and
(iii) reference characteristic sorption strain parameters for at least $CH_4$ and SAG, for the reference SPS pressure and reference sorbed gas composition; and (f) producing the calculated SPS porosity value for a pre-selected SPS pressure and a pre-selected sorbed gas composition using the quantitative relationship and reference values determined in part (e).

According to the present invention, there is also provided a method for producing a calculated SPS porosity value for a coal bed having an in-situ sorbed gas composition, the method comprising:

obtaining test results from at least three independent field tests, $c_1$, $c_2$ and $c_3$, on the coal bed comprising an initial-condition field test, an injection field test using an injection fluid selected from the group consisting of water and a WAG, and a production field test using a SAG, where the test results from of $c_1$, $c_2$ and $c_3$ each independently include at least:

a field test SPS pressure, a field test absolute permeability, and a field test sorbed gas composition, so that the test results from each of $c_1$, $c_2$ and $c_3$ can be correlated in a quantitative relationship to determine:

(i) a reference SPS porosity, (ii) a reference absolute permeability, and (iii) reference characteristic sorption strain parameters for at least $CH_4$ and SAG, for a reference SPS pressure and a reference sorbed gas composition; and there by allowing the calculated SPS porosity value to be produced for a pre-selected SPS pressure and a pre-selected sorbed gas composition, using the quantitative relationship and the reference values of (i), (ii), (iii).

According to the present invention, there is further provided a method for producing a calculated SPS porosity value for coal bed, comprising:

(a) determining, from the data of test 1, an initial absolute permeability, $k_{a-1}$, at an initial SPS pressure, $p_1$, and a test 1 free gas composition;

(b) determining, from the data of test 2 comprising injecting an injection fluid selected from the group consisting of water and a WAG into the coal bed, an injection absolute permeability, $k_{a-2}$, at an injection SPS pressure, $p_2$, and a test 2 free gas composition;

(c) determining, from the data of test 3 comprising injecting a SAG into the coal bed, producing gas from the coal bed, a SAG production absolute permeability, $k_{a-3}$, at a SAG production SPS pressure, $p_3$, and a test 3 free gas composition;

(d) determining a sorbed gas composition corresponding to each of the free gas compositions for each test in parts (a), (b) and (c);

(e) producing values for total multicomponent volumetric sorption strain, $\epsilon_1$, $\epsilon_2$, and $\epsilon_3$, and total multicomponent volumetric sorption strain at atmospheric pressure, $\epsilon_{atm-1}$, $\epsilon_{atm-2}$, and $\epsilon_{atm}$-3, for each sorbed gas composition in part (d);

(f) solving Equations (1) and (2) for (i) a SPS porosity at atmospheric pressure, $\phi_{atm}$, (ii) an absolute permeability at atmospheric pressure, $k_{a-atm}$, and (iii) characteristic sorption strain parameters, for a reference pressure=atmospheric pressure, $p_{atm}$, at which pressure, there is a substantially negligible sorbed gas composition effect on $\phi_{atm}$, $k_{a-atm}$, and a characteristic sorption strain parameters, using SPS pressures $p_1$, $p_2$ and $p_3$, absolute permeability values $k_{a-1}$, $k_{a-2}$ and $k_{a-3}$ and total multicomponent volumetric sorption strain, $\epsilon_1$, $\epsilon_{atm-1}$, $\epsilon_2$, $\epsilon_{atm-2}$, $\epsilon_3$, and $\epsilon_{atm-3}$, from part (e):

$$\frac{\phi_c}{\phi_{atm}} = 1 + \frac{(p_c - p_{atm})}{\phi_{atm} M} + \frac{1}{\phi_{atm}}\left(1 - \frac{K}{M}\right)(\varepsilon_{atm-c} - \varepsilon_c) \quad (1)$$

$$\frac{k_{a-c}}{k_{a-atm}} = \left(\frac{\phi_c}{\phi_{atm}}\right)^3 \quad (2)$$

where $\phi_c$ SPS porosity SPS at pressure $p_c$, dimensionless $\phi_{atm}$ SPS porosity at atmospheric pressure, dimensionless $p_{atm}$ atmospheric pressure, psia $p_c$ SPS pressure, psia M constrained axial modulus, psi $\epsilon_c$ total multicomponent volumetric sorption strain at SPS pressure $p_c$, dimensionless $\epsilon_{atm-c}$ total multicomponent volumetric sorption strain at atmospheric pressure, dimensionless K bulk modulus, psi c test number 1, 2, 3, . . . c $k_{a-c}$ absolute permeability at pressure $p_c$, md $k_{a-atm}$ absolute permeability at atmospheric pressure, md (g) producing the calculated the SPS porosity value for a pre-selected SPS pressure and a pre-selected sorbed gas composition, using Equation (1) and $\phi_{atm}$, $k_{a-atm}$ and the characteristic sorption strain parameters determined in step (f).

According to the present invention, there is also provided a well-test procedure for producing a calculated SPS porosity value for for a coal bed, the coal bed having at least one injection means comprising a wellbore and at least one producing means that can communicate with at least a portion of the coal bed, comprising:

obtaining a $1^{st}$ data set (a) so that an initial absolute permeability, $k_{a-1}$, of a coal bed can be determined form an initial SPS pressure and an initial free gas composition;

(b) injecting a first injection fluid into the at least one injection means at a pressure greater than the initial SPS pressure and obtaining $2^{nd}$ data set so that an injection absolute permeability, $k_{k-2}$, can be determined for at an injection SPS pressure, $p_2$;

(c) shutting in the at least one injection means;

(d) injecting a second injection fluid having a different sorption capacity than the first injection fluid into the at least one injection means at a pressure greater than the initial SPS pressure;

(e) shutting in the at least one injection means;

(f) producing fluid from the coal bed through the at least one producing means and obtaining a $3^{rd}$ data set so that a production absolute permeability, $k_{a-3}$, can be determined for a production SPS pressure, $p_3$; and (g) obtaining a $4^{th}$ data set of production data for the fluid produced in part (f), wherein at least the first injection fluid and the second injection fluid recited in parts (b) and (d) are independently selected from the group consisting of the following first injection fluid/second injection fluid combinations:

(i) WAG/SAG, (ii) SAG/WAG, (iii) water/SAG, and (iv) SAG/water, wherein a WAG is a fluid comprising at least about 70% (by vol.) of a weaker adsorbing fluid and a SAG is a fluid comprising at least about 70% (by vol.) of a stronger adsorbing fluid, so that the $1^{st}$, $2^{nd}$, $3^{rd}$ and $4^{th}$ data sets can be correlated in a quantitative relationship to determine the coal bed's
   (i) reference SPS porosity,
   (ii) reference absolute permeability, and
   (iii) reference characteristic sorption strain parameters for at least $CH_4$ and SAG,
for a reference SPS pressure and a reference sorbed gas composition; and
thereby allowing a calculated SPS porosity value to be produced for a pre-selected SPS pressure and a pre-selected sorbed gas composition,
A use comprising:
   (i) obtaining the calculated SPS porosity value, and
   (ii) using the calculated SPS porosity value for determining at least one value selected from the group consisting of: absolute permeability, relative permeability, effective permeability, water saturation, injection pressure, injection rate, injected fluid composition, produced fluid composition, gas flow rate in the coal bed and water flow in the coal bed;
in the process selected from the group consisting of: p1 fluid production from the coal bed, fluid sequestration in the coal bed and combination thereof.

BRIEF DESCRIPTION OF THE DRAWINGS

The process of the present invention will be better understood by referring to the following detailed description of preferred embodiments and the drawings referenced therein, in which.

DETAILED DESCRIPTION OF THE PREFERRED EMBODIMENTS

Figure 1A:
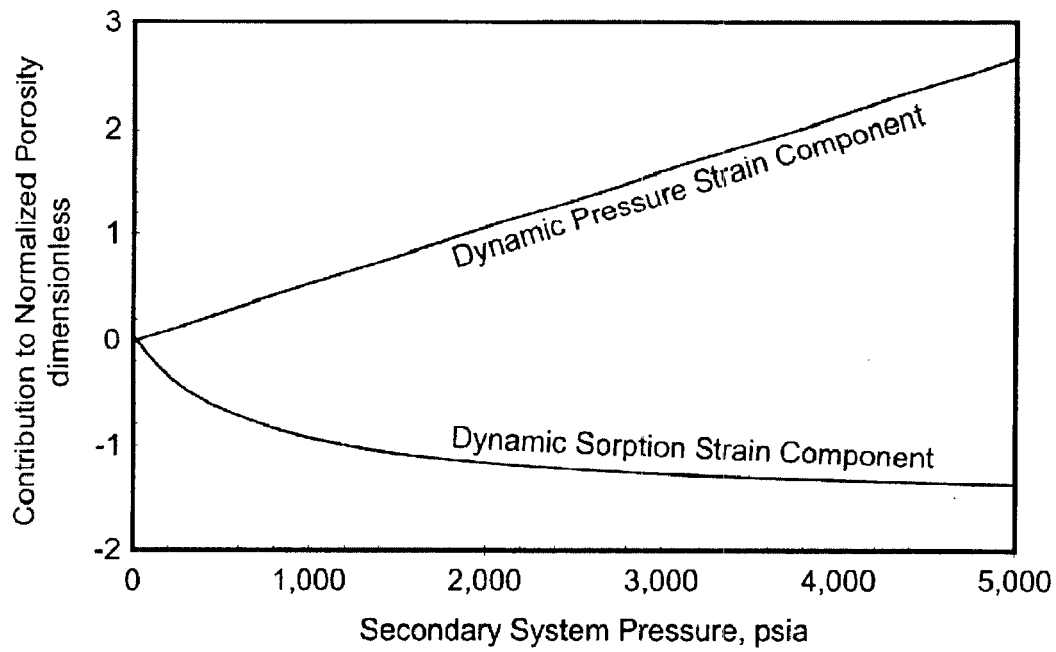
FIG. 1A is a graphical illustration of a hypothetical example illustrating the contribution of dynamic pressure strain and dynamic multicomponent sorption strain components of Equation (1) to normalized porosity resulting from injecting a sorbing gas.

For convenience, the nomenclature used in the Detailed Description and claims is summarized in Table 13 at the end of the Detailed Description.

Definitions

"Coal" is a combustible rock, containing more than about 50% by weight carbonaceous material, formed by compaction and induration of plant matter. Coal is classified by type (kinds of plant matter), rank (degree of metamorphism) and grade (degree of impurity). Coal also contains minerals, typically clay minerals, such as kaolinite and montmorillonite. Higher coal ranks tend to have greater amounts of associated $CH_4$. Accordingly, coal comprises, without limitation, carbon, hydrogen, nitrogen, oxygen, sulfur, phosphorus, silicon, calcium, magnesium and heavy metals.

A "coal bed" or "coal seam" is a stratum or layer of coal.

A "coal bed formation" refers to a body of strata containing coal beds and typically one or more other strata including, without limitation, clay, shale, carbonaceous shale, sandstone and other inorganic rock types. While a coal bed formation generally contains organic matter, at any one location the thickness of organic matter present can vary from almost none to nearly 100% of the formation thickness.

"Coalbed methane" (CBM), also known as "coal gas," is a natural gas consisting of $CH_4$, lesser amounts of ethane, propane and higher hydrocarbons, and inorganic gases, such as $CO_2$ and $N_2$. CBM may be present in a free state, sorbed state and/or in solution with water or liquid hydrocarbons. Free gas stored by compression (i.e., dictated by pressure and temperature conditions) may be present in both the primary and secondary porosity systems (defined below), though to a lesser degree than the sorbed gas. CBM solution gas dissolved in water that may be present, if any, will typically be a smaller percentage than sorbed CBM present in the coal bed.

"Free gas" is a gas whose volumetric properties can be estimated with an equation of state such as the Real Gas Law, pV=nzRT or the Peng-Robinson equation of state. Free gas is not sorbed gas in the coal bed's secondary porosity system, although the gas may have been or may become sorbed in the primary porosity system. The composition of the free gas (i.e., the relative amounts of each component in a free gas mixture) is dependent on its equilibrium with sorbed gas in the primary porosity system and, therefore, changes during injection and/or production. As used herein, a produced gas is assumed to be representative of the free gas composition.

"Sorbed Gas" is a gas contained within the micropores and mesopores of the primary porosity system. Due to the small size of the micropores and mesopores, there is a high surface area for attracting gas molecules to the organic and mineral matter within the primary porosity system. Due to the net attraction, the density of the sorbed gas is believed to be greater than that of free gas at the same temperature and pressure conditions. The volumetric properties of sorbed gas cannot be accurately predicted with the equations of state used for free gas. Gas contained within the primary porosity system is treated as sorbed gas herein, although it is recognized that there could be some free gas within the primary porosity system.

"Sorption" refers to the general physical process where gas molecules in close proximity to solid material molecules experience a net attraction to the solid molecules. The term "sorption" as used in this document also refers to "adsorption" and "desorption" where the volume of sorbed gas increases and decreases, respectively.

"Fluid" means a liquid, gas, finely divided solids and combinations thereof that change shape or direction uniformly in response to an external force imposed on it.

"Stronger adsorbing gases or fluids" (collectively referred to herein as "SAG") are fluids having an atmospheric pressure boiling point greater than that of $CH_4$, i.e., greater than $-164°$ C. Thus, as used herein, "weaker adsorbing gases or fluids" (collectively referred to herein as "WAG") are fluids having a boiling point less than that of $CH_4$, i.e., lower than $-164°$ C.

"Porosity" in general is the ratio of the pore volume ("$V_p$", also referred to as void volume) within a material to the bulk volume of the material. There are two major subtypes of coal porosity, namely a primary porosity system and a secondary porosity system, each having two principal porosity subtypes:

A "primary porosity system" is comprised of micropores and mesopores resulting from natural coal-forming processes. Micropores are pores having a diameter less than about 2 nanometers (nm) (i.e., $2 \times 10^{-9}$ m). Mesopore diameters are in the range of from about 2 nm to about 50 nm. Isolated macropores can also form part of the primary porosity system, but are not usually considered a principal subtype of the primary porosity system. Isolated macropores have diameters in the range of from about 50 nm to about 1 mm and are not connected to other macropores or natural fractures (i.e., not substantially contributing to Darcy flow). Fluid transfer in the primary porosity system is primarily by diffusion, which usually obeys Fick's Law.

A "secondary porosity system" (for brevity, "SPS") is comprised of interconnected macropores in the range of from about 50 nm to about 1 mm, and natural fractures that are generally less than about 1 mm in width. Natural fractures include cleats and joints, defined below. For purposes of the discussion herein, non-propped induced fractures can also form part of the SPS. Generally, the SPS provides the conduit for mass transfer to wells, by Darcy flow (i.e., fluid flow under a pressure gradient).

"Permeability" ("k") is a rock property that quantifies the ability of a porous rock to transmit fluids through the rock due to a pressure gradient, which is the change in pressure along a flow path divided by the length of the flow path. Permeability is typically determined from pressure data, for example using core samples, and calculated from Darcy's Law based on pressure gradients, fluid properties and flow geometry. Increased permeability results in greater flow rates for a given pressure gradient. There are three different terms used to describe permeability: absolute, effective and relative.

"Absolute permeability" ("$k_a$") is the permeability that is determined when only one fluid is present in the coal. Typical commercial CBM reservoirs have an absolute permeability in the range of from about 1 to 25 md, but some CBM reservoirs may have an absolute permeability as great as about 600 md. Absolute permeability can be determined by a method like that described in Chapter 5 of Gas Research Institute Report GRI-94/0397 (Mavor, M. and Saulsberry, J. L. "Testing Coalbed Methane Wells" in *A Guide to Coalbed Methane Reservoir Engineering* March 1996).

"Effective permeability" ("$k_e$") is the permeability of one fluid in the presence of one or more other fluids. If two different fluid phases are present, the vapor phase interferes with the liquid phase and vice versa. Two immiscible liquid phases (e.g., water and oil) can also interfere with each other. Accordingly, due to a fluid/fluid interference, the effective permeability is less than the absolute permeability. In coal, which has both gas and water present, the effective permeability is a function of gas and water saturation in the secondary porosity system. Effective permeability can be determined by a method like that described in Johnson et al. ("Calculation of Relative Permeability from Displacement Experiments" *Trans. AIME* 216:370–372; 1959).

"Relative permeability" ("$k_r$") is the effective permeability divided by the absolute permeability.

"Effective conductivity" is a measure of the ability of a fluid to flow through a porous rock of given thickness. Accordingly, the effective conductivity to gas is the multiplication product of the effective permeability of gas ("$k_{eg}$") and the thickness of the porous rock. Likewise, the effective conductivity to water is the multiplication product of the effective permeability of water ("$k_{ew}$") and the thickness of the porous rock.

"Water saturation," $S_w$, is the ratio between the water volume, $V_w$, and the pore volume, $V_p$ (also referred to as void volume), in the SPS. "Gas saturation" is the ratio between the gas volume and $V_p$ in the SPS.

"Impermeable" rock is a rock of such low permeability that it has little or no effect upon the fluid flow in adjacent permeable rock.

"Secondary porosity system compressibility" is the fractional change in SPS pore volume per unit pressure change in the SPS. For brevity, secondary porosity system compressibility will be referred to herein as "fracture compressibility," even though the SPS, as defined above, can also include interconnected macropores as well as fractures.

"Matrix compressibility" is the fractional change in coal matrix bulk volume per unit change in the pressure imposed on the coal matrix. The coal matrix includes, among other things, the primary porosity system, solid material and water, and is bounded by the SPS.

"Cleats" are natural fractures in coal. Types of cleats include, without limitation, face cleats, butt cleats, and tertiary cleats. Face and butt cleats are the most common fractures observed in CBM reservoirs. Face and butt cleats are generally orthogonal or substantially orthogonal to each other and are generally perpendicular to bedding surfaces. Shorter length butt cleats commonly terminate in longer length face cleats. Tertiary cleats commonly terminate in the face or butt cleats, indicating that they were formed later in time: Tertiary cleats provide increased connectivity between face and butt cleats and, thereby, increase the overall permeability of the cleat system.

"Joints" are larger scale fractures with inter-fracture spacing on the order of feet. Joints tend to have greater heights than cleats and can cut across lithotypes and coal/inorganic rock interbeds. Similar to tertiary cleats, joints can increase the overall fracture system connectivity and permeability, but on a much larger scale. Joints can also increase permeability in the vertical direction.

"Induced fractures" are fractures that are created by injecting or producing fluids into and/or from a coal bed. Induced fractures also include natural fractures whose length has been increased, with or without increasing the fracture's aperture.

"Fracture aperture" is the distance between the two coal matrix planes bounding a fracture, i.e., width.

"Reservoir pressure" ("$P_R$") means the average pressure of a well's drainage area at a specified depth. The reservoir pressure of the formation may change over time as fluids are injected into the formation and/or fluids are produced from the formation.

"Bottom-hole pressure" ("$P_W$") means the pressure at the same depth as the center point of the reservoir within the wellbore. Bottom-hole and reservoir pressure are usually specified at the same depth.

"Bottom-hole temperature" refers to the temperature at the same depth as the center point of the reservoir within the wellbore.

"Fracture extension pressure" ("$P_E$") is the pressure required to extend an existing induced fracture and/or cleat.

$P_E$ can change during an injection, for example, without limitation, due to coal heterogeneity and pressure losses in an induced fracture. Accordingly, $P_E$ is often indicated by a pressure range.

"Fracture pressure" ("$P_F$") is equal to the minimum horizontal in-situ stress and is often referred to as closure stress. $P_F$ is commonly interpreted to mean the pressure required to initiate the opening of an existing natural or induced fracture. $P_F$ is less than $P_E$. Two reasons that $P_E$ is greater than $P_F$ are, without limitation, (1) friction between fracture surfaces and injected fluids and (2) fracture tip toughness, i.e. the proclivity for a material to resist failure by fracture extension.

"Volumetric strain" ("$\epsilon$") is a measure of deformation presented as the change in volume divided by the original volume. Since the total bulk volume of the coal bed is substantially constant, a change in the SPS bulk volume (i.e., SPS void volume) is substantially equal in magnitude, but opposite in sign, to a change in the primary porosity system bulk volume (i.e., coal matrix volume). Accordingly, when the SPS bulk volume increases, the coal matrix volume decreases by substantially the same amount. And, when the coal matrix volume increases, the SPS bulk volume decreases by substantially the same amount.

As used herein, "characteristic sorption strain parameters" are the terms $\epsilon_{\infty i}$ and $p_{\epsilon i}$, which are substantially constant for a particular gas component in a specified coal bed. The term $\epsilon_{\infty i}$ is the characteristic volumetric sorption strain at infinite pressure for component i in a multicomponent gas (dimensionless). And the term $p_{\epsilon i}$ is the pressure at a sorption strain of 0.5 $\epsilon_{\infty i}$ for component i in a multicomponent gas (psia). The terms can be used, for example, in Equation (4) to determine the volumetric sorption strain for component i in a multicomponent gas, which in turn can be used, for example, in Equation (5) to determine the total multicomponent volumetric sorption strain.

General Description

Generally, the inventors have discovered a method for predicting the secondary porosity system ("SPS") porosity, $\phi$, and thereby permeability, of a coal bed. The method involves determining an initial condition in the coal bed, including an initial SPS pressure and an initial sorbed gas composition, determining a pressure strain effect due to increasing the SPS pressure to a value greater than the initial SPS pressure, and determining a sorption strain effect due to changes in the sorbed gas composition resulting from decreasing the $CH_4$ content and increasing the content of a stronger adsorbing fluid (SAG). The initial condition, pressure strain effect and sorption strain effect are correlated in a quantitative relationship to determine a reference SPS porosity, a reference absolute permeability and reference characteristic sorption strain parameters, at a reference SPS pressure and reference sorbed gas composition.

Preferably, the method correlates data from at least three test conditions including an initial condition, an injection condition using water and/or a weaker adsorbing fluid (WAG), and a production condition after injecting a stronger adsorbing fluid (SAG).

Preferably, the reference pressure is atmospheric pressure, at which pressure substantially no gas is sorbed to the coal matrix. Accordingly, at atmospheric pressure the SPS porosity, $\phi_{atm}$, absolute permeability, $k_{a-atm}$, and characteristic sorption strain parameters are essentially independent of gas composition. The values for $\phi_{atm}$ and $k_{a-atm}$, along with the characteristic sorption strain parameters, can then be used to produce a calibrated model for a particular coal bed. In turn, the calibrated model can be used to predict the coal bed's $\phi$ and permeability as a function of a pre-selected injection or production fluid's composition and/or SPS pressure condition. For example, the calibrated model can be used for a different injection and/or production fluid composition at a SPS pressure used in one of the test conditions. Alternatively, the calibrated model can be used for a test condition fluid composition at a different injection and/or production SPS pressure. Or the calibrated model can be used for predicting the coal bed's $\phi$ and permeability for an injection and/or production fluid composition or SPS pressure, different from the test condition fluid compositions and SPS pressures. Preferably, the pre-selected SPS pressure is less than fracture pressure.

Porosity Model

In general terms, the inventors' model for predicting the SPS porosity under fluid injection and/or production conditions is represented by the following relationship, where the SPS porosity is a function of a reference SPS porosity, such as $\phi_{atm}$:

$$\begin{bmatrix} SPS \\ Porosity \end{bmatrix} = \begin{bmatrix} Reference \\ SPS\ Porosity \end{bmatrix} + \begin{bmatrix} Dynamic \\ Pressure\ Strain \end{bmatrix} + \begin{bmatrix} Dynamic\ Multicomponent \\ Sorption\ Strain \end{bmatrix}$$

Up to this point, others in the field of coal bed reservoir modeling have neglected the effect on sorption strain due to changes in (1) multicomponent free gas composition during production or injection and (2) multicomponent sorbed gas composition in the primary porosity system. Thus, others in the field of coal bed reservoir modeling have neglected the interactive and competing effects on SPS porosity arising from (a) dynamic pressure strain, due substantially to pressure changes in the SPS, and (b) dynamic multicomponent sorption strain, due substantially to coal matrix swelling and shrinking, as fluids are being injected and/or produced. More specifically, if considered at all, those skilled in the art have assumed that the sorption strain component is only dependent on the SPS pressure, while neglecting the effect of the changing sorbed gas composition in the primary porosity system (i.e., dynamic multicomponent sorption strain). Accordingly, previous methods for predicting a coal bed's SPS porosity fail to provide SPS porosity and, hence, permeability estimates, consistent with actual field performance.

More specifically, one quantitative expression for predicting SPS porosity, in view of these interactive and competing effects, is represented by Equation (1), using atmospheric pressure as the reference SPS pressure:

$$\frac{\phi}{\phi_{atm}} = 1 + \frac{(p - p_{atm})}{\phi_{atm} M} + \frac{1}{\phi_{atm}}\left(1 - \frac{K}{M}\right)(\varepsilon_{atm} - \varepsilon) \tag{1}$$

where $\phi$ secondary porosity system porosity at pressure p, dimensionless $\phi_{atm}$ secondary porosity system porosity at atmospheric pressure, dimensionless $p_{atm}$ atmospheric pressure, psia p secondary porosity system pressure, psia M constrained axial modulus, psi $\epsilon$ total multicomponent volumetric sorption strain at pressure p, dimensionless $\epsilon_{atm}$ total multicomponent volumetric sorption strain at atmospheric pressure, dimensionless K bulk modulus, psi The inventors' model shares certain attributes with the P&M Model discussed above under Background of the Invention. However, there are several significant differences and attributes the inventors' model has over the P&M Model. Hence, as discussed more fully below, the inventors' proposed model provides significant advantages over the P&M Model as well as others.

A relationship between $k_a$ and $\phi$ was previously described by Palmer & Mansoori (ibid, discussed more fully above) and revised by the present inventors in view of Equation (1). The revised permeability/porosity relationship is presented in Equation (2), again using atmospheric pressure as the reference SPS pressure:

$$\frac{k_a}{k_{a-atm}} = \left(\frac{\phi}{\phi_{atm}}\right)^3 \quad (2)$$

where $k_a$ absolute permeability at secondary porosity system pressure, md $k_{a-atm}$ absolute permeability at atmospheric pressure, md As described mathematically in Equation (1), $\phi$ is affected by two basic mechanisms, which inevitably interact with each other to affect a fracture's aperture. One mechanism relates to changing the pressure in the coal bed's SPS, which affects pressure strain, while a second mechanism relates to the coal matrix's ability to swell or shrink with gas adsorption or desorption, respectively, which affects sorption strain. And, as described by the porosity/permeability relationship in Equation (2), $k_a$ is also affected by the same basic mechanisms.

For example, assuming a constant coal bed bulk volume, a net 1% change in the coal matrix volume, due to either pressure strain and/or sorption strain, can change $\phi$, by a factor of 2 or more, while the corresponding $k_a$ changes by a factor of 8 (i.e., $2^3$) or more, in view of the porosity/permeability relationship in Equation (2).

In Equation (1), the term $[(p-p_{atm})/\phi_{atm}M]$ represents $\phi$ changes due to pressure strain. Hereinafter, this term will be referred to as the "dynamic pressure strain component." As used herein, pressure strain is a measure of the change in SPS pore volume, relative to its volume at the reference pressure, in this case, atmospheric pressure, due to changes in pressure inside coal bed fractures. As the pressure in the SPS increases, the fracture aperture can be increased, while reductions in pressure result in reduced fracture aperture. The extent of fracture aperture change per unit pressure change in the SPS is substantially a function of the coal bed's fracture compressibility, which in turn depends on the inherent properties of the coal bed. In general, injecting gas balloons fractures and compresses the coal matrix. Accordingly, because the overall reservoir volume is constant, SPS pore volume increases and matrix volume decreases. Therefore, other factors aside, increased SPS pressure results in increased $\phi$ and increased $k_a$.

Meanwhile, the term $$\left[\frac{1}{\phi_{atm}}\left(1 - \frac{K}{M}\right)(\varepsilon_{atm} - \varepsilon)\right]$$

in Equation (1) represents $\phi$ changes due to sorption strain. Hereinafter, this term will be referred to as the "dynamic multicomponent sorption strain component." As used herein, sorption strain is a measure of the change in SPS pore volume, relative to its volume at the reference pressure (and, as appropriate, the reference gas composition), in this case atmospheric pressure, due to coal matrix shrinking or swelling resulting substantially from fluid (typically a gas) adsorption or desorption. Some fluids are more strongly adsorbed to coal than CBM, causing the coal matrix to swell more than it does when CBM is adsorbed to coal. Accordingly, $\phi$ and $k_a$ are decreased by SAG sorption due to a net gain in sorbed gas content with subsequent coal swelling. Meanwhile, other fluids are less strongly sorbed than CBM. For less strongly sorbed fluids, $\phi$ and $k_a$ are increased as CBM is desorbed, for example, either by displacing with WAG or by primary production.

Accordingly, in an injection and/or production process, dynamic pressure strain and dynamic multicomponent sorption strain are interactive in their effect on $\phi$ and permeability. For example, a fluid injected into a coal bed will balloon fractures and, depending on its chemical composition, will have a tendency to be adsorbed into the coal matrix. Of course, SAGs have a greater tendency to increase a coal matrix's swelling. But it is also believed that adsorbed SAGs, such as $CO_2$, can also weaken the coal matrix as more SAG is adsorbed into the matrix. This weakening makes the coal matrix more sensitive to pressure exerted on or around (i.e., outside) the matrix, such as, for example, during injection. The extent of aperture changes per unit pressure change in the region outside the coal matrix will substantially be a function of the coal bed's matrix compressibility, which depends on the inherent properties of the coal bed in response to the type and volume of SAG adsorbed in the coal matrix.

So, when injection is stopped, the pressure outside the coal matrix decreases, which allows the swelling coal matrix to reduce fracture apertures (i.e., the SPS becomes more constricted). But, during injection periods, the increased SPS pressure inside the fractures causes the fractures to balloon (i.e., the SPS expands). Typically, this ballooning tends to overcome coal matrix swelling by compressing portions of the matrix, so that the coal matrix volume is either restored substantially to its original volume or reduced below its original volume. Consequently, despite periodic swelling in the coal matrix, injection is still possible.

One way to view this interaction between dynamic pressure strain effects versus dynamic multicomponent'sorption strain effects on aperture size is by considering a ballooning expansion and constriction process. A fracture in the SPS, which can be envisioned as a "hot dog" type balloon with a high aspect ratio, is surrounded by a substantially resilient solid material (i.e., coal matrix). So, an increase in aperture size can be envisioned as blowing a gas, such as SAG, into a "hot dog" type balloon. As the pressure in the high aspect ratio balloon increases, the balloon expands first at one end and then progressively along the balloon's longitudinal axis (i.e., the fracture axis). This process can be envisioned as expanding the fracture's aperture. Meanwhile, the walls of the balloon apply a compression force on the surrounding coal matrix, while gas is blown into the balloon, thereby compressing the coal matrix and restricting the balloon's expansion to some degree.

Because the walls of the balloon are fluid permeable, when SAG is the injected gas, much of the SAG that permeates the balloon is adsorbed by the coal matrix, which has a tendency to swell the coal matrix depending upon the pressure inside the balloon. But, when gas is no longer blown into the balloon, the gas leaks out of the balloon, balloon pressure is reduced, and the compression force on the coal matrix is reduced accordingly. The coal matrix will swell, thereby constricting the balloon under lower pressure. As the matrix continues to swell, the balloon constricts accordingly. Finally, the balloon constricts to a volume smaller than its original volume (i.e., the SPS becomes more constricted) and the coal matrix's volume is larger due to swelling.

Figure 1B:
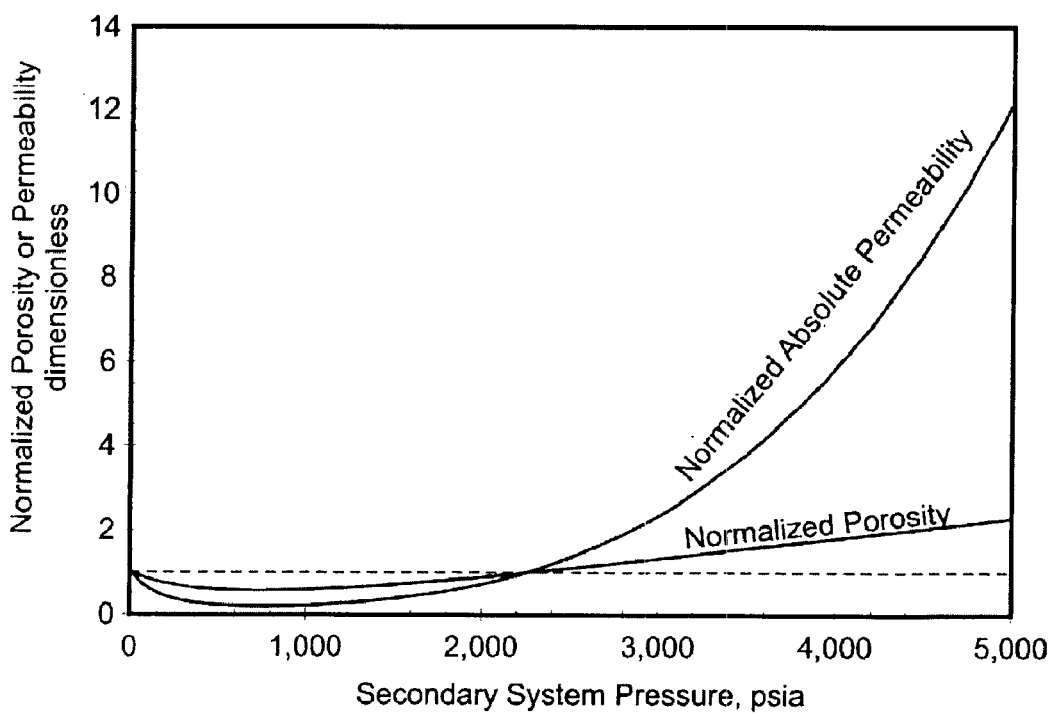
FIG. 1B is a graphical illustration of the FIG. 1A example illustrating the effect of secondary porosity system ("SPS") pressure on a normalized SPS porosity, $\phi$, computed with Equation (1) and a normalized absolute permeability, $k_a$, computed with Equation (2)

The effects of the dynamic pressure strain and dynamic multicomponent sorption strain components of Equation (1) are illustrated in a hypothetical example in FIGS. 1A and 1B. As shown in FIG. 1A, if the dynamic pressure strain component is considered alone when a fluid is injected into a coal bed, the volumetric strain appears to follow a linear dependence on pressure. The injected fluid balloons the fracture system at increased SPS pressure, thereby compressing the coal matrix. Accordingly, when a fluid is injected, volumetric strain due to dynamic pressure strain alone is always greater than 0 and increases linearly with pressure along the line labeled "Dynamic Pressure Strain Component" in FIG. 1A. When water is injected, the linear relationship between total strain and SPS pressure is expected to follow the line labeled "Dynamic Pressure Strain Component" with little, if any, contribution from sorption strain effects.

Although pressure strain also influences the total volumetric strain when sorbing fluids are injected, volumetric strain is further affected by dynamic multicomponent sorption strain. For example, $CH_4$ and SAGs, such as $CO_2$, are sorbed to the coal matrix. The sorption process causes the matrix to swell, so that the dynamic multicomponent sorption strain component in Equation (1) will always be less than or equal to zero for a SAG. Accordingly, when considering the dynamic multicomponent sorption strain component alone, volumetric strain decreases with increasing SPS pressure along the line labeled "Dynamic Sorption Strain Component" in FIG. 1A. The degree to which the dynamic multicomponent sorption strain component influences total volumetric strain is dependent, in part, on how strongly the gas is sorbed into the coal matrix.

When the dynamic pressure strain and dynamic multicomponent sorption strain components are added in Equation (1), the normalized SPS porosity, $\phi/\phi_{atm}$, (1+dynamic pressure strain+dynamic multicomponent sorption strain) for this hypothetical example changes with SPS pressure along the line labeled "Normalized Porosity" in FIG. 1B. The normalized permeability based upon Equation (2) changes with SPS pressure along the line labeled "Normalized Absolute Permeability" in FIG. 1B. As illustrated by the portion of each line below the value 1 (represented by a dashed line) in FIG. 1B, the dynamic multicomponent sorption strain component of Equation (1) is more dominant at lower pressures for adsorbing fluids. But, as the SPS pressure increases, in this case above about 2,250 psia, the dynamic pressure strain component of Equation (1) becomes more dominant than the dynamic multicomponent sorption strain component and the normalized SPS porosity of Equation (1), and hence the normalized absolute permeability of Equation (2), becomes greater than 1.

Thus, the normalized porosity model developed by the inventors correlates the effects of dynamic pressure strain and dynamic multicomponent sorption strain to calibrate a coal bed's properties to SPS pressure for better predicting $\phi$ and $k_a$ for pre-selected injection and/or production fluid compositions and pressures.

As discussed above, the P&M Model also accounts for changes in $\phi$ due to pressure strain and sorption strain. However, also as discussed above, the primary limitations of the P&M Model include: (1) assuming constant strain parameters, and therefore static gas composition, and assuming strain parameters and gas composition are the same as the original in-situ gas composition, and (2) accounting only for changes in $\phi$ and permeability during production. Because the gas composition in the P&M Model is constant, it is applicable only to production of original in-situ gas composition. Moreover, even if the P&M Model was applied to an injection case, the injected gas composition would have to be the same as the original in-situ gas composition, e.g., where the produced gas is reinjected into the reservoir. However, in ECBM recovery and fluid sequestration projects, the injected and produced gas compositions can be dramatically different from the original in-situ composition. Another secondary disadvantage of the P&M Model is that the initial reservoir properties are used as the reference point. However, as discussed below, initial reservoir properties are a function of the initial gas composition and the initial pressure. Therefore, in order to effectively use the P&M Model reference point, both a reference gas composition and reference pressure must be accounted for. However, Palmer and Mansoori failed to account for a reference gas composition.

In contrast, the inventors' model (1) accounts for changing gas composition and, therefore, strain parameters, and (2) can be applied to both injection and production. These two advantages of the inventors' model are discussed more fully below. As a further advantage over the P&M Model, the inventors' model preferably uses atmospheric properties as reference properties.

Reference Reservoir Properties

Preferably, the inventors' model uses SPS porosity at atmospheric pressure, $\phi_{atm}$, as the reference porosity because $\phi_{atm}$, pressure strain and sorption strain for a particular coal bed are essentially the same for all gas compositions at atmospheric pressure. Specifically, at atmospheric pressure, there is substantially no gas contained within the coal matrix. Therefore, gas composition does not substantially affect $\phi_{atm}$ and, hence, $k_{a-atm}$. Accordingly, by correlating $\phi_{atm}$ and $k_{a-atm}$ values for different test conditions, the model can be calibrated and then Equations (1) and (2) can be used to predict $\phi$ and permeability for a pre-selected injection and/or production pressure and fluid composition.

Conversely, the P&M Model uses porosity at initial reservoir pressure as a reference pressure. However, short term WAG and SAG injections have different effects on SPS porosity even though the reservoir pressure may not change appreciably. Therefore, the P&M Model SPS porosity at initial reservoir pressure may not be the same for all gas compositions.

Effects of Gas Composition

The sorption strain component of Equation (1) accounts for coal matrix swelling and shrinkage due to fluid sorption and composition. As discussed more fully above, the P&M Model assumes a constant produced gas composition, which is a valid assumption as long as changes in the produced gas composition are relatively minor. However, in ECBM recovery projects and sequestration projects where fluid is injected into the coal bed, the P&M Model assumption is no longer valid because the in-situ sorbed gas composition changes and porosity is affected by changes in the sorption strain due to changes in sorbed gas composition. Likewise, producing multi-component gases with different sorption characteristics reduces the net gas content, and changes the sorbed gas composition, thereby changing the sorption strain. Accordingly, as discussed more fully below, the claimed method accounts for sorption strain caused by different fluids, whether the in-situ sorbed gas composition changes by injecting a substantially constant gas composition or the injected or produced gas composition changes with time.

It is known that strain-pressure relationships for a single component gas can be fit with a Langmuir type equation as described in Equation (3). See, for example, Levine, J. R. (ibid).

$$\varepsilon_s = \varepsilon_{\infty s} \frac{p}{p + p_{\varepsilon s}} \quad (3)$$

where $\varepsilon_s$ single component volumetric sorption strain, dimensionless $\varepsilon_{\infty s}$ characteristic single component volumetric sorption strain at infinite pressure, dimensionless p SPS pressure, psia $p_{\varepsilon s}$ single component characteristic pressure at a sorption strain of $0.5\varepsilon_{\infty s}$, psia The volumetric sorption strain for each component in a multicomponent gas, caused by sorption at any composition and pressure, can be computed with a relationship described in Equation (4):

$$\varepsilon_i = \varepsilon_{\infty i} \frac{\frac{p x_i}{p_{\varepsilon i}}}{1 + p \sum_{j=1}^{n} \frac{x_j}{p_{\varepsilon j}}} \quad (4)$$

where $\varepsilon_i$ volumetric sorption strain for component i in a multicomponent gas, dimensionless $\varepsilon_{\infty i}$ characteristic volumetric sorption strain at infinite pressure for component i in a multicomponent gas, dimensionless $p_{\varepsilon i}$, $p_{\varepsilon j}$ characteristic pressures at a sorption strain of 0.5 $\varepsilon_{\infty i}$ for components i and j, respectively, in a multicomponent gas, psia $x_i$, $x_j$ mole fractions of components i and j, respectively, in the sorbed gas phase, dimensionless n number of components in multicomponent gas p SPS pressure, psia The total multicomponent volumetric sorption strain is determined by summing the volumetric sorption strain due to each gas species in Equation (4), according to Equation (5):

$$\varepsilon = \sum_{i=1}^{n} \varepsilon_i \quad (5)$$

where $\varepsilon$ total multicomponent volumetric sorption strain, dimensionless $\varepsilon_i$ volumetric sorption strain component i in a multicomponent gas, dimensionless n number of components in multicomponent gas The total multicomponent volumetric sorption strain calculated in Equation (5) is subsequently used in Equation (1). In this way, Equation (1) and the method described herein accounts for different volumetric sorption strains caused by the swelling and shrinkage effect of different fluids.

Adsorption

Different fluids shrink or swell the coal matrix relative to $CH_4$. Fluids that are more strongly adsorbed than $CH_4$ are referred to as stronger adsorbing fluids (SAG) and fluids that are less strongly adsorbed than $CH_4$ are referred to as weaker adsorbing fluids (WAG).

One method for determining whether a fluid would be a SAG or WAG is to compare the boiling point of the injection fluid relative to $CH_4$. The atmospheric pressure boiling point is believed to be a generally reliable indicator of the relative strength of fluid adsorption in a coal bed, i.e., the higher the boiling point, the greater the adsorption strength. For illustrative purposes, atmospheric pressure boiling points for a number of compounds of potential interest are listed in Table 1.

TABLE 1

| Component | Atmospheric Pressure Boiling Point (° C.) | Relative Strength |
|---|---|---|
| 1,1,2-trichloro-1,2,2-trifluoroethane ($CCl_2FCClF_2$) | 47.6 | |
| Sulfur Trioxide ($SO_3$) | 44.8 | |
| Trichlorofluoromethane ($CCl_3F$) | 23.7 | |
| Nitrogen Dioxide ($NO_2$) | 21.2 | |
| Dichloromonofluoromethane ($CHCl_2F$) | 8.9 | |
| Dichlorotetrafluoroethane ($CClF_2CClF_2$) | 3.6 | |
| Sulfur Dioxide ($SO_2$) | −10 | |
| Dichlorodifluoromethane ($CCl_2F_2$) | −29.8 | |
| Chloropentafluoroethane ($CClF_2CF_3$) | −37.7 | |
| Propane ($C_3H_8$) | −42.1 | |
| Hydrogen Sulfide ($H_2S$) | −60.7 | |
| Sulfur Hexafluoride ($SF_6$) | −63.8 | |
| Hexafluoroethane ($CF_3CH_3$) | −78.2 | |
| Carbon Dioxide ($CO_2$) | −78.5 | |
| Chlorotrifluoromethane ($CClF_3$) | −81.4 | |
| Fluoroform ($CHF_3$) | −84 | |
| Nitrous Oxide ($N_2O$) | −88.5 | |
| Ethane ($C_2H_6$) | −88.6 | ↑ |
| Xenon (Xe) | −107.1 | Stronger |
| Tetrafluoromethane ($CF_4$) | −128 | Adsorbing |
| Nitric Oxide (NO) | −151.8 | Fluids (SAG) |
| Methane ($CH_4$) | −164 | Methane |
| Oxygen ($O_2$) | −183.0 | Weaker |
| Argon (Ar) | −185.7 | Adsorbing |
| Carbon Monoxide (CO) | −191.5 | Fluids (WAG) |
| Nitrogen ($N_2$) | −195.8 | ↓ |
| Hydrogen ($H_2$) | −252.8 | |
| Helium (He) | −268.9 | |

As used herein, fluids with atmospheric boiling points less than that of $CH_4$, i.e. less than about −164° C., are believed to be weaker adsorbing fluids (WAGs), while those with atmospheric boiling points greater than that of $CH_4$, i.e. greater than about −164° C., are believed to be stronger adsorbing fluids (SAGs). For example, helium is considered substantially non-adsorbing in coal and it has the lowest boiling point of the compounds listed in Table 1.

In general, the sorption capacity of coal increases with pressure, depth and coal rank. For example, for a given depth and a similar reservoir pressure, anthracite generally has a greater sorption capacity than low-volatile bituminous coal, which, in turn, has a greater sorption capacity than medium-volatile bituminous coal and high-volatile bituminous coal.

$CO_2$ reduces the absolute permeability of a coal bed by swelling the coal matrix. Based on the relative adsorption strength in Table 1, the inventors expect that other SAGs, for example $H_2S$, having a higher atmospheric pressure boiling point and, therefore, a stronger adsorption strength, will swell the coal matrix to a greater degree than is caused by adsorption of an equal volume of $CO_2$. Therefore, the absolute permeability reduction caused by injecting $H_2S$ is expected to be greater than that caused by injecting an equal volume of $CO_2$.

It will be understood however, that the relative sorption capacity of compounds listed in Table 1 is provided for qualitative purposes only. For example, some compounds, such as $O_2$, may chemically react with coal so that adsorption and/or desorption can be affected by hysteresis effects.

Also, it will be understood that some fluids can be injected as liquids, for example liquid $CO_2$ and $H_2S$, but may vaporize under wellbore and/or formation conditions. Other fluids will stay in the same phase after injection. For example, $H_2S$ injected in a liquid state does not necessarily vaporize in the coal bed.

During injection for ECBM or sequestration projects, injected gases may be mixtures of SAGs and may include one or more WAGs. Also, injected gas compositions may change over time. For instance, for ECBM, since WAGs are known to increase produced $CH_4$ volumes more rapidly than SAGs, a greater WAG concentration may be used early in the life of an ECBM project. Later, WAGs breakthrough to production wells and the injected WAG concentration may be reduced to reduce WAG concentration in the produced gas. For both sequestration and ECBM, WAG injection pressure is greater than for SAG, thereby increasing compression requirements and cost. As a result, the WAG content in the injected fluid may have to be adjusted to an economically acceptable level at an appropriate time, to balance treatment and compression costs.

Sources of $CO_2$ include flue gas effluent from, for example, without limitation, power plants or internal combustion engines. Flue gases typically contain from about 13 to about 20% $CO_2$ and may require treatment to increase the $CO_2$ concentration to optimum levels as discussed above.

An example of a $H_2S$ source is a gas-treating plant that removes $H_2S$ from natural gas prior to sale. Such an effluent is often a mixture of $H_2S$ and $CO_2$ containing from about 5% to about 95% $H_2S$.

Assumptions

Equation (1) makes the following assumptions:
1. The theory of linear elasticity for strain changes is applicable to coal. Specifically, the inventors' model assumes that deformations in coal are proportional to stress and are not permanent. This is a very common assumption for developing rock mechanics models for many rock types.
2. Reservoir strain is uniaxial. A uniaxial strain condition is a condition where one principal stress dominates. In the case of coal beds, the principal stress is normally in the vertical direction due to overburden weight.
3. The overburden weight and resulting overburden stress is constant.
4. The total bulk volume of the reservoir (including primary and secondary porosity systems) is constant.
5. Fluid compressibility in the SPS is high, which is a reasonable assumption during gas injection and production since gas compressibility is high relative to that of water and rock.
6. Reservoir temperature remains constant. This is generally the case, although there may be some relatively small temperature changes near the wellbore if injected fluid temperatures are dramatically different than the surrounding rock temperature.
7. Coal bed SPS porosity is less than about 0.05.
8. Rock mechanical properties, such as Poisson's ratio and Young's modulus, are constant with changing pressure in accordance with the analysis done by Zheng et al. ("Static and Dynamic Testing of Coal Specimens" Paper 9120, 1991 Society of Core Analysts, 5$^{th}$ Annual Technical Conference, August 1991).

However, the inventors' model may be adjusted if it is desirable to account for effects of changing one or more properties, rather than assuming the property remains constant. For example, it may be desirable to account for changes in overburden stress due to, for example, differences in stress conditions in coal seams at different depths. Also, it may be desirable to add a temperature strain component to the inventors' model if the reservoir temperature changes significantly. In addition, a coal at significantly different overburden stress and/or temperature conditions may have different coal rank and/or rock mechanical properties that would cause differences in the pressure strain component.

As indicated above, the inventors' model assumes a substantially constant overburden stress. If desired, the inventors' model may also be adjusted to account for the influence of "effective" stress on rock mechanical properties caused by changes in overburden stress. Effective stress is the difference between the total stress (vertical and horizontal) and the SPS pressure as shown by Equation (6) (Gidley, et al. Recent Advances in Hydraulic Fracturing, SPE Monograph 12 (1989) p. 58).

$$\sigma_e = \sigma - bp \qquad (6)$$

where $\sigma_e$ effective stress, psia $\sigma$ total stress, psia b poroelastic constant, dimensionless p SPS pressure, psia For many coal seams, the total stress in Equation (6) is primarily due to the vertical stress caused by the overburden weight. Accordingly, the vertical stress is dependent on the vertical stress gradient, which is typically in the range from about 1 to about 1.1 psi/ft. The vertical stress gradient can be calculated, for example, by integrating density log data from the surface to the depth of interest with Equation (7) as shown by Gidley, et al. (ibid)

$$\sigma'_v = \int_0^z \frac{\rho_r}{144} dz \qquad (7)$$

where $\sigma'_v$ vertical stress gradient, psi/ft $\rho_r$ overburden rock density as a function of depth, lbm/ft$^3$ dz infinitesimal change in depth, feet z depth of interest, feet When considering coal seams at different depths, the differences in effective stress between seams caused by differences in overburden weight or reservoir pressure may not be negligible. For example, a deeper coal seam or deeper parts of the same coal seam may be at a greater effective stress than the coal located at shallower depths and $\phi$ and $k_a$ could be lower in the deeper coals. As a result, $\phi_{atm}$ and $k_{a-atm}$ values for coals located at different depths could be different. It is also possible that coal seams at different depths could have different reservoir pressures that may cause the initial effective stress condition to be different.

For brevity, the model calibration method discussed more fully below assumes that the overburden stress is constant for the coal seam from which the calibration data were obtained. However, as discussed above, in some cases, it may be desirable to relate the calibrated model to effective stress so that the model can be used at other effective stress conditions caused by differences in depth that cause changes in overburden stress. Equation (8) can be used to convert the calibrated model to be dependent on effective stress. The value for the poroelastic constant, b, is normally assumed to be one unless available data suggest otherwise.

$$\sigma_e = \sigma'_v \, z - bp \qquad (8)$$

Because Equation (8) correlates SPS pressure and effective stress, the calibrated model and porosity/permeability relationship can be used for other effective stress conditions and other $\phi_{atm}$ and $k_{a\text{-}atm}$ values.

Coal seams at different depths may require separate testing to calibrate the inventors' model for each depth range. It would also be more accurate to measure rock properties and gas storage capacity parameters for each seam in this situation. The need to measure reservoir data for coal seams at different depths is common in the CBM production industry and is not unique to the inventors' model.

It is also possible that the sorption strain component may be affected by differences in temperature between seams, resulting in different relationships between sorption strain and SPS pressure. For example, increased temperature would cause the primary porosity system to expand causing a contraction of the SPS and a reduction in permeability. Conversely, decreased temperature would cause the primary porosity system to contract allowing expansion of the SPS and increased permeability.

Differences in temperature may also affect the relationship between gas storage capacity and pressure as greater temperature generally results in lower storage capacity, all other factors being equal. Accordingly, at higher temperatures, storage capacity is reduced and gas is released thereby reducing sorption strain. In contrast, reduced temperatures could increase storage capacity causing gas to be sorbed thereby increasing sorption strain.

Generally, the constant reservoir temperature assumption is appropriate since (1) conductive and convective heat transfer while gas is traveling down the well will either cool off hot gases or warm up cold gases resulting in gas temperature similar to reservoir temperature upon reaching the reservoir, and (2) even if the injected gas does not reach reservoir temperature in the wellbore, it will do so within several feet of the wellbore upon entering the reservoir and should not affect the accuracy of the inventors' model. However, in cases where reservoir temperature is affected more significantly, it may be desirable to account for the effects by adding a temperature strain component to Equation (1).

One example of a temperature strain component, described in Palmer & Mansoori (ibid), is presented below in Equation (9):

$$-d\phi = -\frac{1}{M} dP + \left[\frac{K}{M} + f - 1\right]\gamma dP - \left[\frac{K}{M} - 1\right]\alpha dT_R \qquad (9)$$

where $d\phi$ infinitesimal change in SPS porosity, dimensionless
M constrained axial modulus, psi
dP infinitesimal change in SPS pressure, psia
K bulk modulus, psi
f undefined fraction in Palmer & Mansoori between 0 and 1, ibid
$\gamma$ grain compressibility, psi$^{-1}$
$\alpha$ grain thermal expansivity, ° F.$^{-1}$
$dT_R$ infinitesimal change in reservoir temperature, ° F.

However, it should be noted that the Palmer and Mansoori equation does not account for effects of temperature on sorption strain. Specifically, as discussed above, gas storage capacity and the amount of gas sorbed into coal is a function of temperature. Accordingly, for improved accuracy, it is preferable to account for changes in gas storage capacity as a function of temperature for each gas of interest, for example, using test procedures known to those skilled in the art.

There are few measured data relating coal bulk volume to temperature changes. Accordingly, coal bulk volume data are preferably measured in a laboratory for more accurate representation of the thermal strain component.

If added to the inventors' model, the thermal strain component is preferably calibrated with field test data. For example, an injection test that purposely alters the reservoir temperature sufficiently could provide $k_a$ estimates for another temperature condition. In this case, either a very hot fluid, such as steam, or a very cold fluid, such as liquid $N_2$, is injected, possibly at high injection rates, so that wellbore heat transfer effects are reduced to allow the different temperature fluid to enter the coal seam and penetrate the coal seam a sufficient distance from the injection well.

Calibrating the Model

The claimed process has three principal components, including:

| | |
|---|---|
| Component 1 | determining an initial condition in the coal bed, including an initial SPS pressure and an initial sorbed gas composition having an initial $CH_4$ content |
| Component 2 | calibrating a pressure strain effect on the coal bed due to increasing the SPS pressure to a value greater than the initial SPS pressure |
| Component 3 | calibrating a sorption strain effect on the coal bed due to changes in the sorbed gas composition resulting from decreasing the $CH_4$ content and increasing the content of a SAG relative to the initial sorbed gas composition |

As discussed above, one quantitative model for correlating each of the three principal components is presented in Equation (1). In that model, the dynamic pressure strain component is a function of rock mechanical properties, specifically the constrained axial modulus, M, which is a function of Young's modulus, E, and Poisson's ratio, v, (see Equation (12) below). Accordingly, as demonstrated by Equation (1) as one example of a suitable model, it is possible that rock mechanical properties may be estimated from laboratory tests on coal samples or from literature data. In that case, two field tests for initial-condition data and SAG production data can be used for the claimed method. However, the accuracy of the method and the model is improved by conducting an injection test. Accordingly, preferably, data for each of the three principal components is determined from at least three field tests.

In a more preferred embodiment, the pressure strain component is calibrated from a water injection test and the characteristic sorption strain parameters for $CH_4$ and SAG are calibrated from an initial condition test and a SAG production test. In this preferred embodiment there are 3 tests, including 2 tests for calibrating characteristic sorption strain parameters for two components, n, of a fluid composition, specifically, $CH_4$ and a SAG. Most preferably, (n+1) test conditions are used for calibrating the model, where n is the number of major components of a pre-selected fluid composition. Each test condition may not require injection. For example, if a WAG injection test is used for calibrating the pressure strain component, a WAG production test can be used for calibrating sorption strain parameters for WAG by providing additional sorbed gas composition data.

As discussed more fully below, each principal component test produces, among other parameters, an $k_a$ value for a SPS pressure and a specified fluid composition (hereinafter, "test condition"). Accordingly, preferably, at least three $k_a$ values are determined for three different test conditions, differing in fluid composition and/or SPS pressure. Also, accuracy of the model can be even further enhanced by adding other test conditions, as discussed more fully below.

The SPS pressure values used in Equation (1) for principal components 1 and 3 are substantially equal to the initial SPS pressure. However, as discussed more fully below, principal component 2 preferably involves an injection test using either water or WAG. In this case, the SPS pressure for the injection test is the average pressure within the SPS in the region of the reservoir that has been affected by the injected fluid. Accordingly, the SPS pressure for principal component 2 may be lower than the bottom-hole pressure. While it is possible to calculate the average pressure within the affected region, as well as the extent of the affected region, for simplicity, the bottom-hole pressure at the end of the injection period may be used as a first order approximation of the SPS pressure in the affected region. This approximation can be refined later with more accurate methods, for example by reservoir simulation, if desired.

Initial estimated values for $\phi$ and $\epsilon$, are selected for each of the at least three test conditions in a manner discussed more fully below. Then for each of the at least three test conditions, Equations (1) and (2) are solved for $\phi_{atm}$ and $k_{a-atm}$. If the $\phi_{atm}$ and $k_{a-atm}$ values for each test condition are not independently substantially equal, the initial estimated $\phi$ and $\epsilon$ values are adjusted, as discussed more fully below. Revised values for $\phi_{atm}$ and $k_{a-atm}$ are then calculated according to Equations (1) and (2). Again, the $\phi_{atm}$ and $k_{a-atm}$ values for each test condition are independently compared. The computation continues until the $\phi_{atm}$ and $k_{a-atm}$ values for each test condition are independently substantially equal. The calibrated model can then be used for predicting $\phi$ and permeability for a pre-selected injection and/or production pressure and fluid composition.

Determining Initial Absolute Permeability

As stated above, one principal component of the claimed method is determining $k_{a-i}$. A method for determining $k_{a-i}$ from production data is described below under "Determining Permeability Values from Production Data." Alternatively, $k_{a-i}$ may be determined from a gas or water injection test, discussed more fully below under "Calibrating Dynamic Pressure Strain Component." A gas or water injection test is particularly useful when primary production is too low to accurately determine the initial effective conductivities to gas and water. However, the gas or water injection test does not yield produced fluid composition data. Accordingly, unless produced fluid composition data are available from a prior production process, produced fluid composition data will not be available for assisting in calibrating the sorption strain component. In this situation, gas composition estimates can be obtained by desorption of coal samples. Preferably, $k_{a-i}$ is determined with primary production data by:

(1) determining the initial effective conductivity to gas and the initial effective conductivity to water;
(2) determining the coal thickness;
(3) calculating the initial effective permeability to gas, $k_{eg-i}$, and the initial effective permeability to water, $k_{ew-i}$, by dividing the respective initial effective conductivity from step (1) by the coal thickness from step (2);
(4) calculating the initial effective gas-water permeability ratio, $k_{e-i}$ ratio=$k_{eg-i}/k_{ew-i}$ using the values calculated in step (3);
(5) calculating the initial relative gas-water permeability ratio, $k_{r-i}$ ratio (=$k_{rg-i}k_{rw-i}$), which is equal to the $k_{e-i}$ ratio calculated in step (4) because $k_{a-i}$ is the same for both gas and water at a specific test condition;
(6) determining the corresponding initial water saturation, $S_{w-i}$, initial relative permeability to gas, $k_{rg-i}$, and the initial relative permeability to water, $k_{rw-i}$, for the $k_{r-i}$ ratio calculated in step (5); and
(7) calculating $k_{a-i}=k_{eg-i}/k_{rg-i}$ The effective conductivity to gas and the effective conductivity to water in step (1) may be determined from, for example, without limitation, a pressure build-up test, an interference test, a production test, a production test combined with a water injection-falloff test, or a production test combined with a water slug test. These tests are generally known to those skilled in that art. But, for convenience, each test is briefly described under the heading "Effective Conductivity Tests." Preferably, the effective conductivities are determined from a production test followed by a pressure build-up test or an interference test. Most preferably, the effective conductivities are determined from a production test followed by a pressure build-up test.

A production test preferably provides data including, without limitation, surface pressure, surface temperature, bottom-hole pressure, bottom-hole temperature, gas and water production rates and produced fluid composition. The produced fluid composition is used as the initial in-situ free gas composition for determining the initial sorbed gas composition used in calibrating the sorption strain component, as discussed more fully below. During a production test, the bottom-hole pressure and temperature are monitored directly in a manner known to those skilled in the art or estimated from surface temperature and pressure in a manner known to those skilled in the art. Preferably, bottom-hole pressure and temperature are monitored directly.

Effective conductivity testing and analysis procedures are known to those skilled in the art of well testing. See for example GRI-94/0397 (Mavor, M. and Saulsberry, J., ibid).

The coal thickness in step (2) is generally determined by methods known to those skilled in the art, for example, from log data. Log data types include, for example, without limitation, static measurements performed without producing the well and dynamic measurements performed during production.

The most common log used to estimate coal thickness is a density log that presents density as a function of depth. Coal density is significantly less than surrounding inorganic rock density. Accordingly, by analyzing the density data, the coal thickness can be determined by setting a maximum density limit of about 1.75 g/cm$^3$, for example.

Other logs that can be used to estimate coal thickness include, without limitation, gamma ray, neutron porosity, and resistivity logs. In some cases, coal thickness is estimated from the penetration rate while drilling, since coal is drilled more rapidly than inorganic rocks. However, thickness estimates from gamma ray, neutron porosity, resistivity logs and penetration data are less accurate than from density log data because the vertical resolution of these data is less than that for a density log.

Production logs measure the relative flow rate of gas and water as a function of depth. Production logs are more direct indicators of the thickness of the coal seams through which gas and water is entering the well. However, because of cost and the risk of losing production logging tools in the well, operators rarely measure these data.

With respect to step (6), the $k_{r-i}$ ratio calculated in step (5) is used to determine the corresponding $S_{w-i}$, $k_{rg-i}$ and $k_{rw-i}$.

The correlation with the $k_{r-i}$ ratio can be determined with relative permeability tables based on, for example, without limitation, laboratory measurements performed on samples from the coal bed of interest, analysis of production behavior during the life of the reservoir, or literature data.

Preferably, relative permeability data are measured on representative samples from the coal bed of interest. An advantage of using laboratory measurements is that the data are from the specific reservoir of interest and should be more accurate than estimates from other sources. Even when measured, however, the data may differ from the actual in-situ relative permeability since (a) the samples may not be representative of the average in-situ conditions due to reservoir heterogeneity and (b) intact samples are generally from lower permeability portions of the reservoir. Therefore, operators usually do not measure these data because, even if they do so, the data may not be representative, the measurements are expensive and time consuming and few commercial laboratories can measure these data accurately.

Accordingly, reliable published data are often more cost effective. However, because the coal samples used to produce the published data are not likely representative of the coal bed of interest, there will be some error introduced into the calibration. But this error can be minimized if the same set of relative permeability relationships is used consistently in all engineering analyses including, without limitation, well test analysis and reservoir simulation forecasts of production and pressure behavior.

Figure 4:
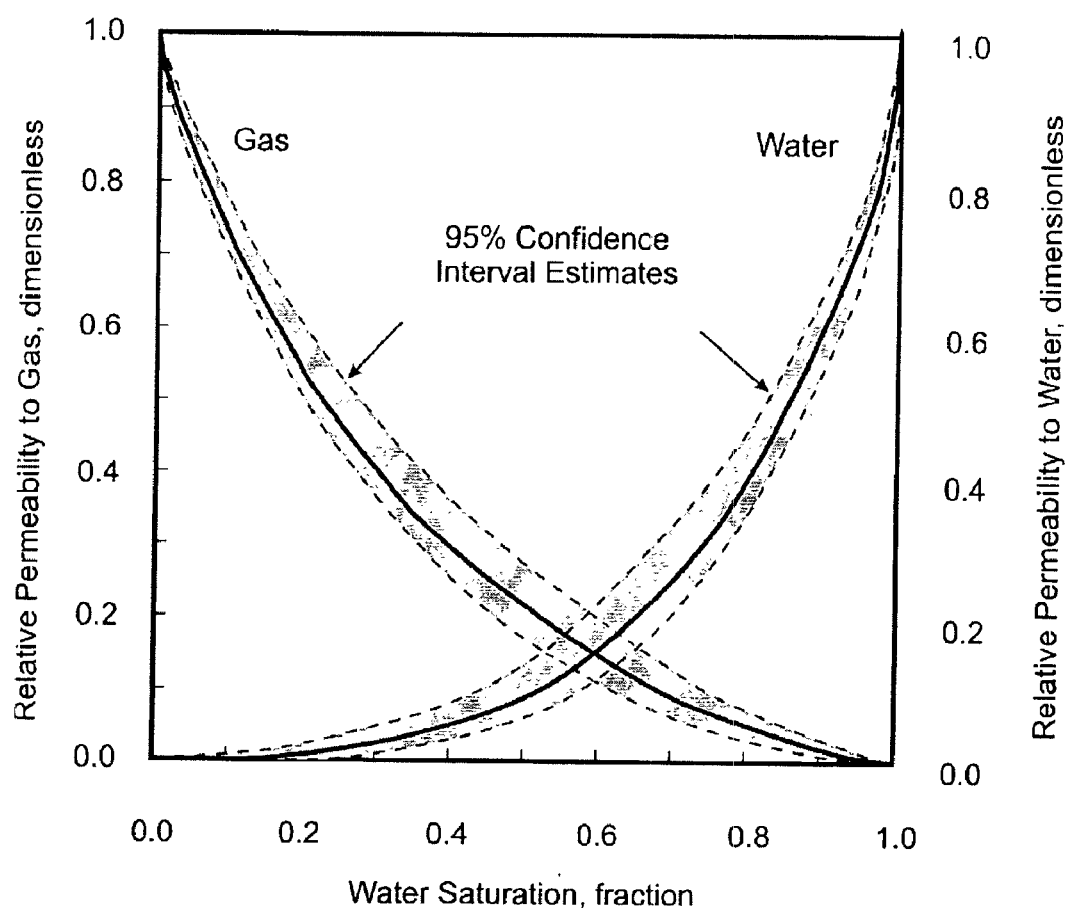
FIG. 4 is redrawn from Gash et al. ("The Effects of Cleat Orientation and Confining Measurement on Cleat Porosity, Permeability and Relative Permeability in Coal," Paper 9321, *Proceedings of the* 1993 *International Coalbed Methane Symposium* The University of Alabama/Tuscaloosa; May 17–21; 1993) illustrating the relationship between $k_{rg}$, $k_{rw}$, and $S_w$.

An example of suitable published data is found in Gash et al. (ibid). Gash et al. produced gas-water relative permeability curves as a function of gas saturation for a number of core samples. Gash et al.'s graph was redrawn by the inventors in FIG. 4 to show the Gash et al. relationship in terms of relative permeability as a function of water saturation. The curves were then digitized by the present inventors and the results are presented in Table 2 below.

TABLE 2

| $S_w$ | $K_{rw}$ | $K_{rg}$ | $K_{rg}/K_{rw}$ |
|---|---|---|---|
| 0.000 | 0.000 | 1.000 | ∞ |
| 0.050 | 0.000 | 0.835 | ∞ |
| 0.100 | 0.000 | 0.720 | ∞ |
| 0.150 | 0.002 | 0.627 | 313.5 |
| 0.200 | 0.007 | 0.537 | 76.71 |
| 0.250 | 0.015 | 0.465 | 31.00 |
| 0.300 | 0.024 | 0.401 | 16.71 |
| 0.350 | 0.035 | 0.342 | 9.771 |
| 0.400 | 0.049 | 0.295 | 6.020 |
| 0.450 | 0.067 | 0.253 | 3.776 |
| 0.500 | 0.088 | 0.216 | 2.455 |
| 0.550 | 0.116 | 0.180 | 1.552 |
| 0.600 | 0.154 | 0.147 | 0.955 |
| 0.650 | 0.200 | 0.118 | 0.590 |
| 0.700 | 0.251 | 0.090 | 0.359 |
| 0.750 | 0.312 | 0.070 | 0.224 |
| 0.800 | 0.392 | 0.051 | 0.130 |
| 0.850 | 0.490 | 0.033 | 0.067 |
| 0.900 | 0.601 | 0.018 | 0.030 |
| 0.950 | 0.731 | 0.007 | 0.010 |
| 0.975 | 0.814 | 0.000 | 0.000 |
| 1.000 | 1.000 | 0.000 | 0.000 |

Table 2 can therefore be used to obtain $S_{w-i}$, $k_{rw-i}$ and $k_{rg-i}$ estimates for the $k_{r-i}$ ratio calculated in step (5). Thereafter, $k_{a-i}$ can be calculated by dividing $k_{eg-i}$ calculated in step (3) by $k_{rg-i}$ estimated using the data in Table 2.

Alternatively, $k_{rg-i}$ may be determined from production data, as discussed below under "Determining Permeability Values from Production Data."

Parameters determined from the data gathered during the test for the first principal component may include, without limitation:

| Parameter | Symbol |
|---|---|
| Effective permeability to gas at initial reservoir pressure and composition | $k_{eg-i}$ |
| Effective permeability to water at initial reservoir pressure and composition | $k_{ew-i}$ |
| Absolute permeability at initial reservoir pressure and composition | $k_{a-i}$ |
| Porosity at initial reservoir pressure and composition | $\phi_i$ |
| Water saturation at initial reservoir pressure | $S_{w-i}$ |
| Initial reservoir pressure | $p_i$ |
| Initial free and sorbed gas composition | |

As discussed above, an estimate for $\phi_i$ may be used for calibrating the inventors' model. And, as discussed more fully below, $\phi_i$ may be determined from water production rates using, reservoir simulation or water material balance techniques. However, there are some situations (e.g., when water production is low), when accurate porosity estimates cannot be obtained from the first principal component. In these situations, as discussed more fully below, a "best-guess" estimate for $\phi$ for at least one test condition may be used as an initial estimate and thereafter adjusted during the calibration process.

The value for $k_{a-i}$ is subsequently used for calibrating the model in the claimed process. Specifically, $k_{a-i}$ is used in Equation (2) to determine $k_{a-atm}$. Also, as discussed more fully below, $k_{a-i}$ may be used to correlate one $\phi$ estimate for estimating initial $\phi$ values for other test conditions. Then, the values for $\phi_{atm}$ and $k_{a-atm}$ calculated for the initial test condition are independently compared to $\phi_{atm}$ and $k_{a-atm}$ values calculated for other test conditions. Also, the initial free and sorbed gas composition data are used for calibrating the sorption strain component of the model, as discussed more fully below.

Also, as discussed more fully below, if the $\phi_{atm}$ and $k_{a-atm}$ values for each test condition are not independently equal, the initial estimates for $\phi$, and/or the characteristic sorption strain parameters for each fluid component are adjusted and $\phi_{atm}$ and $k_{a-atm}$ values are re-calculated for each test condition. The value for $k_{a-i}$ calculated above, however, remains fixed for the iterative computation, which continues until the $\phi_{atm}$ and $k_{a-atm}$ values for each test condition are independently substantially equal.

Once the $\phi_{atm}$ and $k_{a-atm}$ values are determined, $S_{w-atm}$ can be computed by multiplying $S_{w-i}$ by the normalized porosity $\phi/\phi_{atm}$, in Equation (31), presented and discussed more fully below under "Using the Calibrated Model." Then $\phi_{atm}$, $k_{a-atm}$, and $S_{w-atm}$ can be used in Equations (1), (2) and (30) to predict porosity and permeability for a pre-selected injection and/or production pressure and fluid composition.

Calibrating Dynamic Pressure Strain Component

A second principal component of the process claimed herein is calibrating the dynamic pressure strain component, $[(p-p_{atm})/\phi_{atm}M]$, of Equation (1) at a SPS pressure greater than the initial SPS pressure. As discussed above, the dynamic pressure strain component is a function of rock mechanical properties, specifically M, which is a function of E and v, as illustrated in Equation (12). It is possible that an estimated value for M may be estimated from laboratory tests on coal samples or from literature data. However, M is preferably determined from a field injection test, as discussed more fully below. Although discussed independently, it will be appreciated that the pressure strain and sorption strain components of Equation (1) are not solved independently. The process claimed herein results in values for $\phi_{atm}$ and $k_{a-atm}$ by solving Equations (1) and (2) as a whole.

Nonetheless, as discussed above, the dynamic pressure strain component is a measure of the effect of changes in pressure inside the SPS. Accordingly, in order to isolate the effect of pressure strain from the effect of sorption strain on porosity and permeability, an injection fluid is preferably injected into the coal bed at a pressure greater than the initial SPS pressure. Preferably, the injection fluid is water or a WAG. More preferably, the injection fluid is water. Most preferably, the dynamic pressure strain component is calibrated in two steps by first injecting water, then by injecting a WAG.

As stated earlier, when water is injected into a coal bed, the SPS balloons with increased pressure. However, water has substantially no effect on sorption strain. Accordingly, the effect on the dynamic pressure strain component can be substantially isolated from sorption strain effects. Therefore, the dynamic pressure strain component is more preferably calibrated by injecting water.

The SPS also balloons with increased pressure when a WAG is injected. However, there may be some sorption strain effect caused by stripping $CH_4$ with a WAG, resulting in a change in sorbed gas composition. Nonetheless, although coal may have a higher sorption capacity for some WAGs, for example $N_2$, than it does for water or helium, the pressure strain component will still be more dominant than the sorption strain component for $N_2$. However, an advantage of using a WAG is that WAG injection/production data also provide additional information, for example, WAG sweep efficiency, which may be useful for other aspects of an operation. Also, fluid composition data collected from a WAG injection test provide additional calibration data for predicting $\phi$ and permeability for a wider range of fluid compositions. So, although WAG may be used for calibrating the dynamic pressure strain component alone, in a most preferred embodiment WAG injection is conducted after a first injection test with water.

Injection data include, without limitation, injection rates, surface pressure, surface temperature, bottom-hole pressure and bottom-hole temperature. Bottom-hole pressure and temperature may be determined by monitoring directly in a manner known to those skilled in the art or by estimating from surface temperature and pressure in a manner known to those skilled in the art. Preferably, bottom-hole pressure and temperature are monitored directly. Injection fluid composition data may also be collected during the injection test, particularly in the case of WAG injection.

Calibrating the dynamic pressure strain component preferably includes determining an absolute permeability from the data collected. If water is injected, the absolute permeability is approximated by $k_{ew-H2O-inj}$ from the injection portion of the test and $k_{ew-i}$ from the falloff (shut-in) portion of the test. If WAG is injected for calibrating the pressure strain component, a WAG injection absolute permeability, $k_{a-WAG-inj}$, is determined from effective conductivity data in a manner discussed more fully below.

If water injection is used, alone or in combination with WAG injection, water is injected at a pressure greater than $P_R$. A water injection test is preferably conducted for a period in a range from about 2 hours to about 24 hours. More preferably, the water injection test period is in a range from about 4 hours to about 8 hours. Although water may be injected in a liquid and/or vapor phase, water is preferably injected in a liquid phase. Preferably, any change in the reservoir temperature caused by the injected fluid is less than about 10° C. so that temperature effects upon strain parameters can be assumed negligible. More preferably, any change in the reservoir temperature caused by injecting fluid is less than about 5° C.

The effective conductivity to water is determined in a manner discussed below under "Effective Conductivity Tests." The resulting effective conductivity to water obtained from a water injection test approximates the absolute conductivity since gas can be effectively displaced by water during injection. Accordingly, there is a lesser requirement for determining relative permeability to water when a water injection test has been used. Based upon the inventors' experience, water injection can reduce the near-well gas saturation to residual levels between 0 and 10%. When possible, the residual gas saturation is selected to obtain absolute permeability estimates that are consistent with those obtained from production tests before and/or after injection.

If determined from a water injection test, the effective conductivity and effective permeability to water, $k_{ew-H2O-inj}$, are determined at the elevated water injection pressure. And because gas is displaced by water, $k_{ew-H2O-inj}$ is either equal to or less than the absolute permeability at water injection pressure, $k_{a-H2O-inj}$, depending upon the magnitude of the residual gas saturation. Water injection pressures depend upon the absolute permeability of a coal seam and can range from tens of psi above $P_R$ to thousands of psi above $P_R$.

If a fall-off test is performed after water injection, the effective permeability to water approximates $k_{a-i}$, since the pressure rapidly approaches the original reservoir pressure. As discussed above, $k_{a-i}$ is also determined in the first principal component, albeit in a different manner. The $k_{a-i}$ estimates obtained from these different tests should be substantially equal. $k_{a-i}$ estimates that are not substantially equal signal that the residual gas saturation should be adjusted or the relative permeability relationships used in determining the first principal component should be adjusted. As discussed more fully above, relative permeability data are normally obtained from published data. Accordingly, an advantage of using two methods for determining $k_{a-i}$ is that the relative permeability data can be substantiated or adjusted for other absolute permeability determinations discussed below.

If a WAG is injected, alone or in combination with water injection, the WAG is injected at a pressure greater than $P_R$. The WAG can be injected in a single injection period, a longer continuous injection period, or multiple injection periods. Preferably, the WAG is injected for a time in a range from about 6 hours to about 30 days. For example, a single truckload of $N_2$ typically contains about 7,200 gallons (27 m$^3$) $N_2$, which when vaporized is 670,000 scf. This volume can be injected into a well for a period ranging from about 1 hour to about 8 hours. Preferably, any change in the reservoir temperature caused by the injected fluid is less than about 10° C. so that temperature effects upon strain parameters can be assumed negligible. More preferably, any change in the reservoir temperature caused by injecting fluid is less than about 5° C. At greater temperature changes, any reduction in storage capacity and any thermal stress effects, as discussed above in the section entitled "Assumptions," should preferably be taken into account.

The overall WAG injection duration depends upon the volume of WAG that must be injected into the well. The injection duration can be determined by techniques known to those skilled in the art.

The preferred injection time and volume is selected so that the WAG is sorbed into a region extending at least about 30 feet from the well to the average edge of the injection front. More preferably, the WAG-sorbed region is from about 50 feet to about 150 feet from the well. The volume of WAG required to produce the desired WAG-sorbed region is preferably estimated from the WAG storage capacity of the coal seam of interest. The area of the WAG-sorbed region can be estimated with Equation (10). Meanwhile, the distance into the reservoir that the WAG penetrates can be estimated by assuming a shape for the WAG-sorbed region. For example, if the WAG-sorbed region is distributed in a generally circular pattern centered around the well, the distance to the outer edge of the sorbed region can be calculated with Equation (11). The WAG storage capacity in Equation (10) is, in turn, determined by sorption isotherm measurements and extended Langmuir isotherm calculations for estimated in-situ fluid compositions, for example, in the manner discussed more fully below under "Determining Free & Sorbed Gas Composition." In the design stage, the in-situ gas composition can be assumed based upon experience. Fluid composition data measured later will be used for the calibration process.

$$A_{inj} = \frac{32.0368 V_{inj}}{h \bar{p}_c G_s} \quad (10)$$

$$r_{inj} = \sqrt{\frac{A_{inj}}{\pi}} \quad (11)$$

where $A_{inj}$ area of gas sorbed region, ft$^2$ $V_{inj}$ volume of injected gas, scf h coal thickness, feet $\bar{p}_c$ average coal seam density, g/cm$^3$ $G_s$ total gas storage capacity, scf/ton $r_{inj}$ gas penetration distance from the wellbore for circular injection area, feet The WAG injection volume in Equation (10) excludes the volume of WAG required to fill up the wellbore. The total injection volume, which includes the wellbore volume and the volume that enters the coal seam, is preferably significantly greater than the volume of the wellbore and meets or exceeds the required penetration distance. Preferably, the total WAG injection volume is at least twice the volume of the wellbore. More preferably, the total WAG injection volume is from about 5 times to 20 times the wellbore volume. Generally, the wellbore volume criterion is not an operational constraint since a single truck load of $N_2$ often contains 10 or more times the wellbore volume depending upon the diameter and depth of the well.

The fluid used for WAG injection preferably contains at least about 70% (vol.) WAG. More preferably, the injected WAG contains at least about 85% (vol.) WAG. Most preferably, the injected WAG contains substantially no SAG. Suitable WAGs are listed in Table 1. The injected WAG may contain one or more WAGs. Preferably, however, only one type of WAG is used in the test procedure.

During the WAG injection period, the gas injection rates and composition, surface and bottom-hole pressures and temperatures, are measured. Bottom-hole pressure and temperature may be monitored directly in a manner known to those skilled in the art or estimated from surface temperature and pressure in a manner known to those skilled in the art. Preferably, bottom-hole pressure and temperature are monitored directly.

Following WAG injection, the well is then shut-in for a soak period sufficient to equilibrate the in-situ fluid composition. During the soak period, surface and bottom-hole pressures and temperatures are determined. Bottom-hole pressure and temperature may be monitored directly in a manner known to those skilled in the art or estimated from surface temperature and pressure in a manner known to those skilled in the art. Preferably, bottom-hole pressure and temperature are monitored directly.

The length of the shut-in period depends upon coal diffusivity, which is typically determined by measurement of the gas volume released from freshly cut coal samples as a function of time. Diffusivity is inversely proportional to sorption time, $t_s$, which is defined as the time required to release 63% of the gas from a coal sample maintained at constant temperature. Accordingly, the higher the diffusivity, the shorter the sorption time. Gas Institute Report GRI-97/0263 (Mavor et al. "Coalbed Reservoir Gas-In-Place Analysis" pg. 3.1–3.20; 1997) describes diffusivity estimate techniques. Factors affecting diffusivity include coal composition, temperature, and water content. As an alternative, the method described in Mavor, M. J. et al. "Measurement and Evaluation of Coal Sorption Isotherm Data," (SPE 20728, 65th Annual Technical Conference of the Society of Petroleum Engineers, New Orleans, La., Sep. 23–26, 1990) can be used to determine the sorption time for WAG at reservoir temperature.

Diffusivity tests do not distinguish between gases but the inventors believe that different gases would provide different diffusivity values. Accordingly, as used herein, $t_{s\text{-}CBM}$ is the sorption time determined from original in-situ CBM at reservoir temperature. Typically $t_{s\text{-}CBM}$ is in a range from about 3 to about 500 hours, more typically in a range from about 5 hours to about 48 hours, when measured at reservoir temperature.

Preferably, the WAG shut-in period is conducted for at least about 0.5 $t_{s\text{-}CBM}$. More preferably, the shut-in period is in a range from about 0.5 $t_{s\text{-}CBM}$ to about 4 $t_{s\text{-}CBM}$. Most preferably, the shut-in period is in a range from about $t_{s\text{-}CBM}$ to about 2 $t_{s\text{-}CBM}$. Although some sorption times might suggest a shut-in period of about 1.5 hours, practically, the shortest time for a WAG shut-in is about 24 hours. Expressed in units of time, preferably the WAG shut-in period is at least about 24 hours. More preferably, the shut-in period is in a range from about 24 hours to about 80 days. Most preferably, the shut-in period is in a range from about 24 hours to about 40 days. As another general guide, the WAG shut-in time is greater than about 1.5 times the WAG injection time to have sufficient falloff data for estimating permeability.

A production period following WAG shut-in is used to determine produced fluid composition and in-situ $S_w$. The length of the production period is preferably in a range from about 2 days to about 7 days. More specific tests times for permeability estimates based upon the radius of investigation of the test can be determined in a manner known to those skilled in the art. Data collected during the production period include, without limitation, surface and bottom-hole pressures and temperatures, gas and water production rates, and produced fluid composition. Again, bottom-hole pressure and temperature may be determined by monitoring directly in a manner known to those skilled in the art or by estimating from surface temperature and pressure in a manner known to those skilled in the art. Preferably, bottom-hole pressure and temperature are monitored directly.

Optionally, a second shut-in period following production may be conducted to determine any changes in $k_{eg}$ and $k_{ew}$ caused by sorption strain effects due to changes in sorbed gas composition following WAG injection. If a second shut-in period is performed, data collected include, without limitation, surface and bottom-hole pressures and temperatures. Again, bottom-hole pressure and temperature may be determined by monitoring directly in a manner known to those skilled in the art or by estimating from surface temperature and pressure in a manner known to those skilled in the art. Preferably, bottom-hole pressure and temperature are monitored directly.

Preferably, $k_{a\text{-}WAG\text{-}inj}$ is determined by:
(1) determining the effective conductivity to gas during WAG injection;
(2) determining the coal thickness (previously determined for calculating $k_{a\text{-}i}$);
(3) calculating the WAG injection effective permeability to gas, $k_{eg\text{-}WAG\text{-}inj}$, by dividing the WAG injection effective conductivity to gas from step (1) by the coal thickness from step (2). As discussed below under "Effects of Relative Permeability," the effective permeability to water does not change significantly with pressure. Accordingly, the effective permeability to water during WAG injection can be assumed to be the same as the effective permeability to water determined from the first principal component, i.e., when calculating $k_{a\text{-}i}$;
(4) calculating the WAG injection effective gas-water permeability ratio, $k_{e\text{-}WAG\text{-}inj}$ ratio=$k_{eg\text{-}WAG\text{-}inj}/k_{ew\text{-}WAG\text{-}inj}$ using the values calculated in step (3);
(5) calculating the WAG injection relative gas-water permeability ratio, $k_{r\text{-}WAG\text{-}inj}$ ratio (=$k_{rg\text{-}WAG\text{-}inj}/k_{rw\text{-}WAG\text{-}inj}$), which is equal to the $k_{e\text{-}WAG\text{-}inj}$ ratio calculated in step (4) because $k_{a\text{-}WAG\text{-}inj}$ is the same for both gas and water at a specific test condition;
(6) determining the corresponding WAG injection water saturation, $S_{w\text{-}WAG\text{-}inj}$, WAG injection relative permeability to gas, $k_{rg\text{-}WAG\text{-}inj}$, and the WAG injection relative permeability to water, $k_{rw\text{-}WAG\text{-}inj}$, for the $k_{r\text{-}WAG\text{-}inj}$ ratio calculated in step (5); and
(7) calculating $k_{a\text{-}WAG\text{-}inj}=k_{eg\text{-}WAG\text{-}inj}/k_{rg\text{-}WAG\text{-}inj}$.

The steps outlined above may be conducted in the same manner as discussed above for determining $k_{a\text{-}i}$.

The constrained axial modulus, M, used in the dynamic pressure strain component of Equation (1) is a function of rock mechanical properties E (Young's modulus) and $\nu$ (Poisson's ratio) as defined in Equation (12):

$$M = E\frac{1-\nu}{(1+\nu)(1-2\nu)} \qquad (12)$$

where
M constrained axial modulus, psi
E Young's modulus, psi
$\nu$ Poisson's ratio, dimensionless As illustrated in Example 3 below, the values for E and $\nu$ have an effect on the accuracy of the calibration. Accordingly, even though E and $\nu$ values can be found in literature data, E and $\nu$ are preferably determined from test condition data or by laboratory measurements on representative samples from the coal bed of interest. Typically, coal is weaker than rocks such as sandstone and has a smaller E and a larger $\nu$. See, for example, Gidley et al., p. 225 (ibid). Techniques for measuring E and $\nu$ from coal samples are described in, for example, Zheng et al. (ibid).

Alternatively, published data may be used for providing initial estimates for E and $\nu$. See, for example, Mavor et al., SPE 39105, (ibid). Preferably, the published data used for estimating E and $\nu$ were determined for coal of a similar rank and from the same basin. However, if used, the initial estimates for E and $\nu$ should be revised during the calibration.

One method for determining M from test condition data is based on using the relationship between porosity and permeability in Equation (2). Specifically, M becomes a function of the relationship between absolute permeability values between two test conditions. Preferably, the two test conditions used for determining M are water injection and production. Data from a WAG injection test may be used. However, since there is some influence on sorbed gas composition, and therefore sorption strain, the pressure strain effect will not be isolated and the value for M may not be accurate. In contrast, in a water injection test, there is substantially no change in the sorption strain as water does not change the sorbed gas content. Accordingly, the SPS porosity for the water injection test can be related to the initial-condition SPS porosity with Equation (13).

$$\phi_i - \phi_{H2O\text{-}inj} = \frac{p_i - p_{H2O\text{-}inj}}{M} \qquad (13)$$

Since, the SPS porosity values are related to the absolute permeability from each test in the manner of Equation (2), it is possible to combine Equations (14) and (15) to solve for M.

$$\phi_{H2O\text{-}inj} = \phi_i\left(\frac{k_{a\text{-}H2O\text{-}inj}}{k_{a\text{-}i}}\right)^{\frac{1}{3}} \qquad (14)$$

$$M = \frac{p_{H2O\text{-}inj} - p_i}{\phi_i\left[\left(\frac{k_{a\text{-}H2O\text{-}inj}}{k_{a\text{-}i}}\right)^{\frac{1}{3}} - 1\right]} \qquad (15)$$

Once determined, the value of M estimated with Equation (15) is the value used in the model for determining $\phi_{atm}$ and $k_{a\text{-}atm}$. As stated above under "Calibrating the Model", the bottom-hole pressure after injection is higher than the SPS pressure. Accordingly, the estimated value for M may be higher than actual. Therefore, in order to improve the accuracy, the value for $P_{H2o\text{-}inj}$ is preferably an average pressure within the region affected by water injection, which typically occurs relatively close to the wellbore, i.e., within 10 to 20 feet. As a first approximation, this average pressure is similar to the average of the bottom-hole pressure at the end of injection and the average reservoir pressure. An even more accurate estimate for $P_{H2o\text{-}inj}$ could be determined mathematically by integrating the near-well pressure distribution. The near-well pressure distribution can be computed, for example, with a reservoir simulator.

Parameters determined by the second principal component, if using water injection, include, without limitation:

| Parameter | Symbol |
| --- | --- |
| Effective permeability to water at water injection SPS pressure | $k_{ew\text{-}H2O\text{-}inj}$ |
| Effective permeability to water at initial SPS pressure | $k_{ew\text{-}i}$ |
| Absolute permeability at water injection SPS pressure | $k_{a\text{-}H2O\text{-}inj}$ |
| Absolute permeability at initial SPS pressure | $k_{a\text{-}i}$ |
| Water injection SPS pressure | $P_{H2O\text{-}inj}$ |
| Initial SPS pressure | $P_i$ |
| Constrained axial modulus | M |

Parameters determined by the second principal component, if using WAG injection, include, without limitation:

| Parameter | Symbol |
|---|---|
| Effective permeability to gas at WAG injection SPS pressure and composition | $k_{eg\text{-}WAG\text{-}inj}$ |
| Effective permeability to water at WAG injection SPS pressure and composition | $k_{ew\text{-}WAG\text{-}inj}$ |
| Absolute permeability at WAG injection SPS pressure and composition | $k_{a\text{-}WAG\text{-}inj}$ |
| Water saturation at WAG injection SPS pressure | $S_{w\text{-}WAG\text{-}inj}$ |
| Free and sorbed gas composition during WAG injection | |
| WAG injection SPS pressure | $p_{WAG\text{-}inj}$ |

As discussed above, an estimate for $\phi_{H2O\text{-}inj}$ or $\phi_{WAG\text{-}inj}$ is used for calibrating the inventors' model. Techniques for determining an initial estimate for $\phi_{H2O\text{-}inj}$ or $\phi_{WAG\text{-}inj}$ are discussed more fully below.

The values for $k_{a\text{-}H2O\text{-}inj}$ or $k_{a\text{-}WAG\text{-}inj}$, $k_{a\text{-}i}$ and M are subsequently used for calibrating the model in the claimed process. Specifically, $k_{a\text{-}H2O\text{-}inj}$ or $k_{a\text{-}WAG\text{-}inj}$, and $k_{a\text{-}i}$ are used in Equation (2) to determine $k_{a\text{-}atm}$ values for each test condition. Also, as discussed more fully below, $k_{a\text{-}H2O\text{-}inj}$ or $k_{a\text{-}WAG\text{-}inj}$, and $k_{a\text{-}i}$ may be used to correlate one $\phi$ estimate for initial $\phi$ values for other test conditions. Then the values for $\phi_{atm}$ and $k_{a\text{-}atm}$ calculated for water and/or WAG test conditions are independently compared to $\phi_{atm}$ and $k_{a\text{-}atm}$ values calculated for other test conditions. Also, if WAG was injected, the free and sorbed gas composition data are used for calibrating the sorption strain component of the model, as discussed more fully below. Reference to gas composition data during WAG injection will be understood to mean the first produced gas composition during a production period following WAG injection and a soak period. If water injection is used for calibrating the second principal component, the free and sorbed gas compositions are assumed to be same as the initial free and sorbed gas compositions.

As discussed more fully below, if the $\phi_{atm}$ and $k_{a\text{-}atm}$ values for each test condition are not independently equal, the initial estimates for $\epsilon$ and $\phi$ values are adjusted and $\phi_{atm}$ and $k_{a\text{-}atm}$ values are re-calculated for each test condition. The values for $k_{a\text{-}H2O\text{-}inj}$ or $k_{a\text{-}WAG\text{-}inj}$ and $k_{a\text{-}i}$ and M calculated above, however, remain fixed for the iterative computation, which continues until the $\phi_{atm}$ and $k_{a\text{-}atm}$ values for each test condition are independently substantially equal.

Calibrating Dynamic Multicomponent Sorption Strain Component

A third principal component of the process claimed herein is calibrating the dynamic multicomponent sorption component, $$\left[\frac{1}{\phi_{atm}}\left(1 - \frac{K}{M}\right)(\varepsilon_{atm} - \varepsilon)\right],$$

of Equation (1) using a SAG. It will be appreciated that the pressure strain and sorption strain components of Equation (1) are not solved independently. The process claimed herein results in values for $\phi_{atm}$ and $k_{a\text{-}atm}$ by solving Equations (1) and (2) as a whole.

Nonetheless, as discussed above, the dynamic multicomponent sorption strain component is a measure of the effect of coal matrix shrinkage or swelling due to adsorption or desorption of fluids and fluid composition. Although there is an interaction between pressure strain effects versus sorption strain effects on porosity and permeability, the sorption strain effect is more dominant when a SAG is injected. Accordingly, in order to determine the effect of sorption strain, a SAG is injected into the coal bed at a pressure greater than $P_R$.

SAG can be injected in a single injection period, a longer continuous injection period, or multiple injection periods. Preferably, SAG is injected for a time in a range from about 6 hours to about 30 days. For example, a single truckload of $CO_2$ typically contains about 16.5 tons of $CO_2$ (274 Mscf vapor equivalent). This volume can be injected into a well for a period ranging from about 1 hour to about 8 hours. Preferably, any change in the reservoir temperature caused by the injected fluid is less than about 10° C. so that temperature effects upon strain parameters can be assumed negligible. More preferably, any change in the reservoir temperature caused by injecting fluid is less than about 5° C. At greater temperature changes, any reduction in storage capacity and any thermal stress effects, as discussed above in the section entitled "Assumptions," should preferably be taken into account.

The overall SAG injection duration depends upon the volume of SAG that must be injected into the well. The preferred injection time and volume is selected so that the SAG is sorbed into a region extending at least about 30 feet from the well to the average edge of the injection front. More preferably, SAG-sorbed region is from about 50 feet to about 150 feet from the well. The volume of SAG required to produce the desired SAG-sorbed region is preferably estimated from the SAG storage capacity of the coal seam of interest. The area of the SAG-sorbed region can be estimated with Equation (10) above. Again, the distance into the reservoir that the SAG penetrates can be estimated by assuming a shape for the SAG-sorbed region. For example, if the SAG-sorbed region is distributed in a generally circular pattern centered around the well, the distance to the outer edge of the sorbed region can be calculated with Equation (11). The SAG storage capacity in Equation (10) is, in turn, determined by sorption isotherm data and extended Langmuir isotherm calculations for estimated in-situ fluid compositions, for example, in the manner discussed more fully below under "Determining Free & Sorbed Gas Composition." In the design stage, the in-situ gas composition can be assumed based upon experience. Fluid composition data measured later will be used for the calibration process.

Again, the SAG injection volume in Equation (10) excludes the volume of SAG required to fill up the wellbore. The total injection volume, which includes the wellbore volume and the volume that enters the coal seam is preferably significantly greater than the volume of the wellbore and meets or exceeds the required penetration distance. Preferably, the total SAG injection volume is at least twice the volume of the wellbore. More preferably, the total SAG injection volume is from about 5 times to 20 times the wellbore volume. Generally, the wellbore volume criterion is not an operational constraint since a single truck load of $CO_2$ generally contains 4 or more times the wellbore volume depending upon the diameter and depth of the well.

The fluid used for SAG injection preferably contains at least about 70% (vol.) SAG. More preferably, the injected SAG contains at least about 85% (vol.) SAG. Most preferably, the injected SAG contains substantially no WAG. Suitable SAGs are listed in Table 1. The injected SAG may contain one or more SAGs. Preferably, however, only one type of SAG is used in the test procedure.

During the injection period, the gas injection rates and composition, surface and bottom-hole pressures and temperatures, are measured. Bottom-hole pressure and temperature may be monitored directly in a manner known to those skilled in the art, or estimated from surface temperature and pressure in a manner known to those skilled in the art. Preferably, bottom-hole pressure and temperature are monitored directly.

Following SAG injection, the well is shut-in for a soak period sufficient to equilibrate the in-situ gas composition. During the soak period, surface and bottom-hole pressures and temperatures are determined. Bottom-hole pressure and temperature may be monitored directly in a manner known to those skilled in the art or estimated from surface temperature and pressure in a manner known to those skilled in the art. Preferably, bottom-hole pressure and temperature are monitored directly.

As discussed above under "Calibrating Dynamic Pressure Strain Component," the length of the shut-in period depends upon coal diffusivity, which is typically determined by measurement of the gas volume released from freshly cut coal samples as a function of time as in GRI-97/0263, Mavor et al. (ibid). As an alternative, the method described in SPE 20728 (Mavor, M. J. et al., ibid) can be used to determine the sorption time for SAG at reservoir temperature, $t_{S\text{-}SAG}$, from the decline rate in pressure during sorption isotherm measurements. But, nonetheless, $t_{S\text{-}CBM}$ may be used as a first order approximation of $t_{S\text{-}SAG}$ for developing a preliminary estimate of soak time, when time and/or resources for determining $t_{S\text{-}SAG}$ are not immediately available.

Typical coal bed sorption times for CBM are in a range from about 3 to about 500 hours when measured at reservoir temperature.

Preferably, the shut-in period is conducted for at least $0.5t_{S\text{-}SAG}$. More preferably, the shut-in period is in a range from about $0.5t_{S\text{-}SAG}$ to about $4t_{S\text{-}SAG}$. Most preferably, the shut-in period is in a range from about $t_{S\text{-}SAG}$ to about $2t_{S\text{-}SAG}$. Although some sorption times might suggest a shut-in period of about 1.5 hours, practically, the shortest time for a SAG shut-in is about 24 hours. Expressed in units of time for $t_{S\text{-}SAG}=t_{S\text{-}CBM}$, preferably the SAG shut-in period is at least about 24 hours. More preferably, the shut-in period is in a range from about 24 hours to about 80 days. Most preferably, the shut-in period is in a range from about 24 hours to about 40 days. As another general guide, the SAG shut-in time is greater than about 1.5 times the SAG injection time to have sufficient falloff data for estimating permeability.

Following the soak period, the well is produced, while collecting data including, without limitation, produced gas composition, surface pressure, surface temperature, bottom-hole pressure, bottom-hole temperature and gas and water production rates. The length of the production period is preferably in a range from about 2 days to about 7 days. More specific tests times for permeability estimates based upon the radius of investigation of the test can be determined in a manner known to those skilled in the art. Generally, after a soak period, the, SPS pressure will be substantially the same as in the initial SPS pressure, so sorption strain can be evaluated substantially independently from pressure strain using production data.

Optionally, a second shut-in period following production may be conducted to determine the changes in $k_{eg}$ and $k_{ew}$ caused by the SAG. If performed, data collected include, without limitation, surface and bottom-hole pressures and temperatures. Again, bottom-hole pressure and temperature may be determined by monitoring directly in a manner known to those skilled in the art or by estimating from surface temperature and pressure in a manner known to those skilled in the art. Preferably, bottom-hole pressure and temperature are monitored directly.

Calibrating the dynamic multicomponent sorption strain component includes determining a SAG production absolute permeability, $k_{a\text{-}SAG\text{-}p}$, from the data collected. Preferably, $k_{a\text{-}SAG\text{-}p}$ is determined by:

(1) determining the effective conductivity to gas and the effective conductivity to water during SAG production;

(2) determining the coal thickness (previously determined for calculating $k_{a\text{-}i}$);

(3) calculating the SAG production effective permeability to gas, $k_{eg\text{-}SAG\text{-}p}$, and the SAG production effective permeability to water, $k_{ew\text{-}SAG\text{-}p}$, by dividing the respective SAG production effective conductivity from step (1) by the coal thickness from step (2);

(4) calculating the SAG production effective gas-water permeability ratio, $k_{e\text{-}SAG\text{-}p}$ ratio=$k_{eg\text{-}SAG\text{-}p}/k_{ew\text{-}SAG\text{-}p}$ using the values calculated in step (3);

(5) calculating the SAG production relative gas-water permeability ratio, $k_{r\text{-}SAG\text{-}p}$ ratio(=$k_{rg\text{-}SAG\text{-}p}/k_{rw\text{-}SAG\text{-}p}$), which is equal to the $k_{e\text{-}SAG\text{-}p}$ ratio calculated in step (4) because $k_{a\text{-}SAG\text{-}p}$ is the same for both gas and water at a specific test condition;

(6) determining the corresponding SAG production water saturation, $S_{w\text{-}SAG\text{-}p}$, SAG production relative permeability to gas, $k_{rg\text{-}SAG\text{-}p}$, and the SAG production relative permeability to water, $k_{rw\text{-}SAG\text{-}p}$, for the $k_{r\text{-}SAG\text{-}p}$ ratio calculated in step (5); and (7) calculating $k_{a\text{-}SAG\text{-}p}=k_{eg\text{-}SAG\text{-}p}/k_{rg\text{-}SAG\text{-}p}$.

The steps outlined above may be conducted in the same manner as discussed above for determining $k_{a\text{-}i}$. As another alternative, $k_{a\text{-}SAG\text{-}p}$, may be determined from production data, as discussed below under "Determining Permeability Values from Production Data."

The dynamic multicomponent sorption strain component includes the constrained axial modulus, M, as discussed above. The bulk modulus, K, is defined by Equation (16):

$$K = \frac{M}{3}\left(\frac{1+v}{1-v}\right) \quad (16)$$

where
M constrained axial modulus, psi
K bulk modulus, psi
v Poisson's ratio, dimensionless The value for M determined for the second principal component can be used for calibrating the dynamic multicomponent sorption strain component. However, some SAGs may affect the rock properties. For example, the inventors recognize that weakening the coal by SAG sorption may reduce M by changes in E and/or v, depending on the SAG injected. But, for brevity, changes in the M value due to gas sorption have not been expressly addressed quantitatively in Equation (1) because changes are accounted for to some degree by the sorption strain parameters. However, for greater accuracy, it is preferable to conduct a second water injection test after the SAG production test, in order to determine the effect on rock properties and, therefore the values for M and K used in the model.

Alternatively, if data are available relating E and v (and thus M and K) to sorbed gas composition, the inventors' method can include these changes explicitly by specifying that relationship. The calibration would continue to adjust values for $\epsilon$ and $\phi$ until $\phi_{atm}$ and $k_{a\text{-}atm}$ values are substantially the same for each test condition.

Parameters determined by the third principal component include, without limitation:

| Parameter | Symbol |
|---|---|
| Effective permeability to gas at post-SAG injection gas composition and SPS pressure | $k_{eg\text{-}SAG\text{-}p}$ |
| Effective permeability to water at post-SAG injection gas composition and SPS pressure | $k_{ew\text{-}SAG\text{-}p}$ |
| Absolute permeability at post-SAG injection gas composition and SPS pressure | $k_{a\text{-}SAG\text{-}p}$ |
| Water saturation at SPS pressure after SAG-injection | $S_{w\text{-}SAG\text{-}p}$ |
| Free and sorbed gas composition following SAG injection | |
| Post-SAG injection SPS pressure | $p_{SAG\text{-}p}$ |

As discussed above, an estimate for $\phi_{SAG\text{-}p}$ is used for calibrating the inventors' model. Techniques for determining an initial estimate for $\phi_{SAG\text{-}p}$ are discussed more fully below.

The values for $k_{a\text{-}SAG\text{-}p}$, M and K are subsequently used for calibrating the model in the claimed process. Specifically, $k_{a\text{-}SAG\text{-}p}$ is used in Equation (2) to determine $k_{a\text{-}atm}$. Also, as discussed more fully below, $k_{a\text{-}SAG\text{-}p}$ may be used to correlate one $\phi$ estimate for initial $\phi$ values for other test conditions. Then the values for $\phi_{atm}$ and $k_{a\text{-}atm}$ calculated for the SAG test condition are independently compared to $\phi_{atm}$ and $k_{a\text{-}atm}$ values calculated for other test conditions. Also, the free and sorbed gas composition data are further used for calibrating the dynamic multicomponent sorption strain component of the model.

As discussed more fully below, if the $\phi_{atm}$ and $k_{a\text{-}atm}$ values for each test condition are not independently equal, the initial estimates for $\epsilon$ and $\phi$ values are adjusted and $\phi_{atm}$ and $k_{a\text{-}atm}$ values are re-calculated for each test condition. The values for $k_{a\text{-}SAG\text{-}p}$, M and K calculated above, however, remain fixed for the iterative computation, which continues until the $\phi_{atm}$ and $k_{a\text{-}atm}$ values for each test condition are independently substantially equal.

Determining Free & Sorbed Gas Composition

The free gas composition for each test condition is determined by analyzing the produced gas composition using techniques known to those skilled in the art. Suitable techniques for measuring free gas composition include, without limitation, collecting gas samples on location in pressurized sample bottles that are subsequently sent to laboratories for analysis or measuring gas composition on location with portable gas chromatographic equipment. Gas samples in sample bottles sent off-site are typically also analyzed by gas chromatography.

The gas storage capacity of each individual species of significant concentration, for example greater than 5 mol. % in the sorbed gas composition, is calculated according to Equation (17), using the free gas composition for each respective test condition:

$$G_{si} = G_{sLi}[1-(w_a+w_{we})]\frac{\frac{py_i}{p_{Li}}}{1+\sum_{j=1}^{n}\frac{y_j}{p_{Lj}}} \quad (17)$$

where $G_{si}$ storage capacity of component i in a multicomponent gas, in-situ basis, scf/ton $G_{sLi}$ Langmuir storage capacity of component i in a multicomponent gas, dry, ash-free basis, scf/ton $w_a$ ash content, weight fraction $w_{we}$ equilibrium moisture content, weight fraction $p_{Li}$, $p_{Lj}$ Langmuir pressures for component i and j, respectively, in a multicomponent gas, psia $y_i$, $y_j$ mole fractions of component i and j, respectively, in the free gas phase, dimensionless n number of components in multicomponent gas p SPS pressure, psia The total gas storage capacity, $G_s$, for the mixture is the sum of the gas storage capacity for each component, as presented in Equation (18):

$$G_s = \sum_{i=1}^{n} G_{si} \quad (18)$$

The concentration of each component in the sorbed gas phase is computed as the ratio of the component storage capacity to the total storage capacity as presented in Equation (19).

$$x_i = \frac{G_{si}}{G_s} \quad (19)$$

where $x_i$ mole fraction of component i in the sorbed gas phase, dimensionless

The dry, ash-free Langmuir storage capacity for each gas ($G_{sLi}$) is determined from core sample analysis or literature data. Preferably, $G_{sLi}$ is determined by analysis of core samples from the coal bed of interest. Techniques for determining $G_{sLi}$ are known to those skilled in the art and are typically conducted on samples equilibrated to equilibrium moisture content ($w_{we}$). For example, see SPE 20728 Mavor, M. J. et al. ibid.

The Langmuir pressure, $p_L$, for each component is the pressure at which the gas storage capacity for that component is equal to half the storage capacity at infinite pressure. This parameter is determined along with $G_{sL}$ during laboratory measurements of pure component gas storage capacity.

The ash content specified in Equation (17) is the in-situ ash content that corresponds to the average of the coal seam of interest using techniques known to those skilled in the art. See GRI-97/0263 (Mavor ibid). Therefore, Equation (17) results in estimates of the in-situ storage capacity of each gas species.

The sorbed gas composition data are used for determining volumetric sorption strain, $\epsilon$, values, as discussed more fully below. It is preferable to use $\epsilon_i$ values for each component of each sorbed gas composition if sorption isotherm data for each component are available. However, in many cases, operators do not measure sorption isotherm data for components that are present in the sorbed gas in an amount of at less than about 5 mol. %. In this situation, however, components of the sorbed gas composition without isotherm data are preferably at least partially accounted for by adding the concentration value to the appropriate main SAG or WAG component. For example, in the illustrative Example 1 below, the inventors added the concentration values for ethane and propane to the concentration value for $CO_2$, because the higher hydrocarbons were also SAGs.

Selecting Sorption Strain & SPS Porosity Values

The process claimed herein involves estimating initial values for volumetric sorption strain, $\epsilon$, and SPS porosity, $\phi$, for each specified test condition. When using atmospheric pressure as the reference pressure in Equation (1), the value for $\epsilon_{atm}$ approaches zero, since substantially no gas is present in the coal at atmospheric pressure.

Initial values for $\epsilon$ and $\phi$ can be determined in a number of ways. For example, best-guess estimates may be used for $\phi$ for each test condition. And, in order to determine $\epsilon$ and $\epsilon_{atm}$ values for Equation (1), best-guess estimates may be used for each characteristic sorption strain parameter, $\epsilon_{\infty i}$ and $p_{\epsilon i}$, for at least each major component in the sorbed gas composition. As another example, a best-guess estimate for each $\epsilon_{\infty i}$ and $p_{\epsilon i}$ may be used with reservoir simulation software known to those skilled in the art to first produce a $\phi$ estimate for one or more test conditions. Each of the $\epsilon_{\infty i}$, $p_{\epsilon i}$ and $\phi$ estimates can then be used for calibrating the model. The best-guess estimates may be adjusted during model calibration.

However, the number of variables may be reduced by introducing constraints based on the permeability/porosity relationship in Equation (2). For example, for two different tests 1 and 2, where the $k_a$ at the test SPS pressure is known for each test, the ratio of $k_a$ for the two tests constrains the ratio of the respective $\phi$ values as demonstrated in Equation (20).

$$\frac{k_{a1}}{k_{a2}} \left(\frac{\phi_1}{\phi_2}\right)^3 \tag{20}$$

where:

$k_{a1}$ absolute permeability for a $1^{st}$ test condition, md $k_{a2}$ absolute permeability for a $2^{nd}$ test condition, md $\phi_1$ SPS porosity for a $1^{st}$ test condition, dimensionless $\phi_2$ SPS porosity for a $2^{nd}$ test condition, dimensionless Accordingly, if one $\phi$ value is known, the other $\phi$ value can be estimated from Equation (20). Alternatively, by estimating one $\phi$ value, the $\phi$ values for the other two test conditions can be correlated through $k_a$ obtained through test data. The constrained relationship in Equation (20) assists in reducing the number of variables requiring adjusting when solving Equations (1) and (2) for $\phi_{atm}$ and $k_{a-atm}$.

Generally, an initial estimated value for $\phi$ is in the range from about 0.0001 to about 0.01. Selecting an initial estimate for $\phi$ is based upon the change in permeability and porosity for a specific test condition. For instance, if permeability changes are high after injecting SAG, the initial estimate for $\phi_{SAG-p}$ should be lower than the initial estimate for $\phi_i$.

As further guidance, $\phi$ estimates for the first principal component, and other production and/or shut-in test combinations, are preferably consistent with the water production volume. Coal seams that produce larger water volumes generally have greater $\phi$ than those that produce smaller water volumes, other factors being equal. The porosity at SPS pressure is commonly determined with reservoir simulation models or by material balance analysis. For example, the value of $\phi$ at the SPS pressure input to a simulation model is adjusted until the water production volume is matched. When determined in this matter, the estimate of $\phi$ for the first principal component or other production and/or shut-in test combinations is fixed in the inventors' iterative calibration process. Moreover, the correlation in Equation (20) between $k_a$ data and for $\phi$ allows for $\phi$ better estimates for $\phi$ at other test conditions, reducing the number of variables requiring adjustment during calibration. The reservoir simulation derived estimates of $\phi$ are generally more accurate than those determined by material balance, which depends upon assumed water saturation changes and drainage area. The simulation methods do not require these assumptions.

As a further advantage, the $\phi$ estimates determined in Equation (20) can be used to constrain the total multicomponent volumetric sorption strain difference between two test conditions. For example, Equation (21) may be used to correlate $\epsilon$ and $\phi$ values for different test conditions.

$$\varepsilon_1 - \varepsilon_2 = \frac{\phi_2 - \phi_1 + \frac{p_1 - p_2}{M}}{1 - \frac{K}{M}} \tag{21}$$

where:

$\epsilon_1$ total multicomponent volumetric sorption strain for a $1^{st}$ test condition, dimensionless $\epsilon_2$ total multicomponent volumetric sorption strain for a $2^{nd}$ test condition, dimensionless $\phi_1$ SPS porosity for a $1^{st}$ test condition, dimensionless $\phi_2$ SPS porosity for a $2^{nd}$ test condition, dimensionless $p_1$ SPS pressure for a $1^{st}$ test condition, psia $p_2$ SPS pressure for a $2^{nd}$ test condition, psia K bulk modulus, psi M constrained axial modulus, psi As shown by Equation (5), the total multicomponent volumetric sorption strain for any test condition is the sum of the volumetric sorption strain caused by each gas component, each of which is calculated according to Equation (4), using characteristic sorption strain parameters $\epsilon_{\infty i}$ and $p_{\epsilon i}$ for each gas component. Preferably, at least three major gas components, namely, $CH_4$, WAG and SAG, will be involved in calibrating the model. Hence, with three gas components, there will be six sorption strain terms since there are $\epsilon_{\infty i}$ and $p_{\epsilon i}$ terms for each gas component. Therefore, the number of unknown strain terms can be reduced to four, by using Equation (21) and fluid composition data, to calculate two of the $\epsilon_{\infty i}$ values.

For example, consider three tests with test 1 being the initial-condition test, test 2 being a WAG injection test, and test 3 being the SAG production test. Equation (22) can be used to constrain the $\epsilon_{\infty-WAG}$ value using the sorption strain difference between tests 1 and 2. It will be apparent to those skilled in the art how to expand Equation (22) for more than three gas components.

$$\varepsilon_{\infty-WAG} = \frac{(\varepsilon_1 - \varepsilon_2) + (a_{CH_4-2} - a_{CH_4-1})\varepsilon_{\infty-CH_4} + (a_{SAG-2} - a_{SAG-1})\varepsilon_{\infty-SAG}}{a_{WAG-1} - a_{WAG-2}} \tag{22}$$

where:

$a_{i-c}$ pressure component of sorption strain (i.e., strain contribution factor) for component i under test condition c $$a_{CH_4-1} = \frac{\frac{p_1 x_{CH_4-1}}{p_{\varepsilon-CH_4}}}{1 + p_1 \left(\frac{x_{CH_4-1}}{p_{\varepsilon-CH_4}} + \frac{x_{SAG-1}}{p_{\varepsilon-SAG}} + \frac{x_{WAG-1}}{p_{\varepsilon-WAG}}\right)}$$

-continued $$a_{CH_4\text{-}2} = \frac{\dfrac{p_2 x_{CH_4\text{-}2}}{p_{\varepsilon\text{-}CH_4}}}{1 + p_2\left(\dfrac{x_{CH_4\text{-}2}}{p_{\varepsilon\text{-}CH_4}} + \dfrac{x_{SAG\text{-}2}}{p_{\varepsilon\text{-}SAG}} + \dfrac{x_{WAG\text{-}2}}{p_{\varepsilon\text{-}WAG}}\right)}$$

$$a_{SAG\text{-}1} = \frac{\dfrac{p_1 x_{SAG\text{-}1}}{p_{\varepsilon\text{-}SAG}}}{1 + p_1\left(\dfrac{x_{CH_4\text{-}1}}{p_{\varepsilon\text{-}CH_4}} + \dfrac{x_{SAG\text{-}1}}{p_{\varepsilon\text{-}SAG}} + \dfrac{x_{WAG\text{-}1}}{p_{\varepsilon\text{-}WAG}}\right)}$$

$$a_{SAG\text{-}2} = \frac{\dfrac{p_2 x_{SAG\text{-}2}}{p_{\varepsilon\text{-}SAG}}}{1 + p_2\left(\dfrac{x_{CH_4\text{-}2}}{p_{\varepsilon\text{-}CH_4}} + \dfrac{x_{SAG\text{-}2}}{p_{\varepsilon\text{-}SAG}} + \dfrac{x_{WAG\text{-}2}}{p_{\varepsilon\text{-}WAG}}\right)}$$

$$a_{WAG\text{-}1} = \frac{\dfrac{p_1 x_{WAG\text{-}1}}{p_{\varepsilon\text{-}WAG}}}{1 + p_1\left(\dfrac{x_{CH_4\text{-}1}}{p_{\varepsilon\text{-}CH_4}} + \dfrac{x_{SAG\text{-}1}}{p_{\varepsilon\text{-}SAG}} + \dfrac{x_{WAG\text{-}1}}{p_{\varepsilon\text{-}WAG}}\right)}$$

$$a_{WAG\text{-}2} = \frac{\dfrac{p_2 x_{WAG\text{-}2}}{p_{\varepsilon\text{-}WAG}}}{1 + p_2\left(\dfrac{x_{CH_4\text{-}2}}{p_{\varepsilon\text{-}CH_4}} + \dfrac{x_{SAG\text{-}2}}{p_{\varepsilon\text{-}SAG}} + \dfrac{x_{WAG\text{-}2}}{p_{\varepsilon\text{-}WAG}}\right)}$$

Similarly, the $\varepsilon_{\infty\text{-}SAG}$ value can be constrained by the sorption strain difference between tests 1 and 3 as shown by Equation (23). It will be apparent to those skilled in the art how to expand Equation (23) for more than three gas components.

$$\varepsilon_{\infty\text{-}SAG} = \frac{(\varepsilon_1 - \varepsilon_3) + (a_{CH_4\text{-}3} - a_{CH_4\text{-}1})\varepsilon_{\infty\text{-}CH_4} + (a_{WAG\text{-}3} - a_{WAG\text{-}1})\varepsilon_{\infty\text{-}WAG}}{a_{SAG\text{-}1} - a_{SAG\text{-}3}} \quad (23)$$

$$a_{CH_4\text{-}3} = \frac{\dfrac{p_3 x_{CH_4\text{-}3}}{p_{\varepsilon\text{-}CH_4}}}{1 + p_3\left(\dfrac{x_{CH_4\text{-}3}}{p_{\varepsilon\text{-}CH_4}} + \dfrac{x_{SAG\text{-}3}}{p_{\varepsilon\text{-}SAG}} + \dfrac{x_{WAG\text{-}3}}{p_{\varepsilon\text{-}WAG}}\right)}$$

$$a_{SAG\text{-}3} = \frac{\dfrac{p_3 x_{SAG\text{-}3}}{p_{\varepsilon\text{-}SAG}}}{1 + p_3\left(\dfrac{x_{CH_4\text{-}3}}{p_{\varepsilon\text{-}CH_4}} + \dfrac{x_{SAG\text{-}3}}{p_{\varepsilon\text{-}SAG}} + \dfrac{x_{WAG\text{-}3}}{p_{\varepsilon\text{-}WAG}}\right)}$$

$$a_{WAG\text{-}3} = \frac{\dfrac{p_3 x_{WAG\text{-}3}}{p_{\varepsilon\text{-}WAG}}}{1 + p_3\left(\dfrac{x_{CH_4\text{-}3}}{p_{\varepsilon\text{-}CH_4}} + \dfrac{x_{SAG\text{-}3}}{p_{\varepsilon\text{-}SAG}} + \dfrac{x_{WAG\text{-}3}}{p_{\varepsilon\text{-}WAG}}\right)}$$

The sorbed gas composition and SPS pressure data for each test condition are used for calculating each strain contribution factor value in Equations (22) and (23). However, there are two equations and four unknowns. Accordingly, in order to reduce the non-uniqueness of the estimated values for $\varepsilon_{\infty\text{-}CH_4}$, $p_{\varepsilon\text{-}CH_4}$, $p_{\varepsilon\text{-}SAG}$ and $p_{\varepsilon\text{-}WAG}$, a relative magnitude constraint is preferably used. Preferably, $\varepsilon_{\infty\text{-}CH_4}$ is constrained by forcing the $\varepsilon_{\infty i}$ values to increase according to relative storage capacity, i.e., $\varepsilon_{\infty\text{-}WAG} < \varepsilon_{\infty\text{-}CH_4} < \varepsilon_{\infty\text{-}SAG}$. Likewise, the relative magnitude of the $p_{\varepsilon 1}$ values preferably corresponds to the variation observed for sorption isotherm measurements, i.e., $p_{\varepsilon\text{-}WAG} > p_{\varepsilon\text{-}CH_4} > p_{\varepsilon\text{-}SAG}$.

Solution of this system of equations with Equations (1) and (2) generally requires iterative methods. Iteration continues until the values for $\phi_{atm}$ and $k_{a\text{-}atm}$ are each independently substantially equal, for example, within 5% for each test condition.

As an alternative to using Equations (21)–(23), best-guess estimates may be used to estimate initial values for $\varepsilon_{\infty i}$ and $p_{\varepsilon 1}$ for each component for each test condition. Because swelling and shrinkage, which affect $\varepsilon_{\infty}$, are related to gas storage capacity, published sorption isotherm data can be used to guide the initial selection for $\varepsilon_{\infty i}$ values. For $CH_4$ and $CO_2$ data, for example, the relationships published by Levine (ibid) can be used as a starting point, with modification. Specifically, the Levine value for each $\varepsilon_{\infty i}$ value should be multiplied by the ratio of the component storage capacity, $G_{sLi}$, for the reservoir of interest to the Levine storage capacity. Mavor et al. (SPE 39105 ibid) list values for Levine's $G_{sL}$ for $CH_4$ and $CO_2$. As a general rule, $\varepsilon_{\infty\text{-}SAG}$ is typically about 0.02.

For other gases, values for $\varepsilon_{\infty i}$ are increased or decreased relative to their gas storage capacity in coal, as estimated in Table 1. As a general rule, $$\varepsilon_{\infty\text{-}WAG} < \varepsilon_{\infty\text{-}CH_4} < \varepsilon_{\infty\text{-}SAG}.$$

Initial $\varepsilon_{\infty i}$ values should therefore be increased or decreased accordingly in the direction of the relative sorptive capacity.

The Levine $p_{\varepsilon i}$ values can be used, for example, without modification for a first pass estimate. A moderate value of $p_{\varepsilon i}$, such as 500 psia, can also be used as an initial estimate.

During iteration, if $\phi_{atm}$ or $k_{a\text{-}atm}$ for any test condition is too high compared with $\phi_{atm}$ and $k_{a\text{-}atm}$ for other test conditions, the $\varepsilon_{\infty i}$ value for the most sorptive gas component should be reduced. Conversely, if $\phi_{atm}$ or $k_{a\text{-}atm}$ for any test condition is too low, the $\varepsilon_{\infty i}$ and/or the $p_{\varepsilon i}$ value for the most sorptive gas component should be increased.

Determining Permeability Values from Production Data

Although it is preferable to obtain $k_a$ estimates for each test condition from conductivity test data as discussed above, values for $k_a$, $k_e$ and $k_r$ can also be obtained from production data. Specifically, the gas-water production rate ratio is related to the effective and relative gas-water permeability ratios by Equation (24).

$$\frac{k_{eg}}{k_{ew}} = \frac{k_{rg}}{k_{rw}} = \frac{1000 q_g}{5.615 q_w} \frac{\mu_g B_g}{\mu_w B_w} \quad (24)$$

where:

$k_{eg}$ effective permeability to gas, md $k_{ew}$ effective permeability to water, md $k_{rg}$ relative permeability to gas, dimensionless $k_{rw}$ relative permeability to water, dimensionless $q_g$ gas production rate, Mscf/D $q_w$ water production rate STB/D (stock tank barrels per day)

$\mu_g$ gas viscosity, cp $B_g$ gas formation volume factor, in-situ gas volume/ surface gas volume $\mu_w$ water viscosity, cp $B_w$ water formation volume factor, in-situ water volume/ surface water volume The gas and water viscosity and formation volume factor values are usually obtained from correlations based upon gas and water composition with methods well known to those skilled in the art. For example, $\mu_g$ and $B_g$ can be determined with Huber, M. L. (*NIST Thermophysical Properties of Hydrocarbon Mixtures*, NIST Standard Reference Database 4, Standard Reference Data, National Institute of Standards and Technology, Gaithersburg, Md.; 1999). The Huber computer program calculates properties of hydrocarbon gases, $N_2$ and $CO_2$ with the Peng-Robinson equation of state. An example of a suitable reference for determining $\mu_w$ and $B_w$ Brill, J. P. et al. ("Multiphase Flow in Wells" Monograph 17, Society of Petroleum Engineers; 1999).

The relative gas-water permeability ratio can then be used to determine the corresponding $S_w$, $k_{rg}$ and $k_{rw}$, for example, using correlation data in Table 2.

The effective conductivity to gas, $k_{eg}h$, can be determined from the gas production rate and the bottom-hole pressure with Equation (25):

$$k_{eg}h = \frac{q_g p_{sc} T_R \left[\ln\left(\frac{r_d}{r_w}\right) + s\right]}{1.987(10^{-5}) T_{sc} [m(P_R) - m(P_w)]} \quad (25)$$

where $q_g$ gas rate at standard conditions, Mscf/D
$k_{eg}$ effective permeability to gas, dimensionless
h coal thickness, feet
$T_{sc}$ temperature at standard conditions, 519.67° R (60° F.)
m(p) real gas potential, psia$^2$/cp
$P_R$ reservoir pressure, psia
$P_w$ bottom-hole pressure, psia
$p_{sc}$ pressure at standard conditions, 14.69 psia
$T_R$ reservoir temperature, ° R
$r_d$ equivalent steady-state drainage radius, feet
$r_w$ wellbore radius, feet
s skin factor, dimensionless The skin factor, s, is a measure of the near-well resistance to flow caused by alteration of the near-well absolute or effective permeability to gas, water, or both. The skin factor is defined by Equation (26).

$$s = \left(\frac{k}{k_m} - 1\right) \ln\left(\frac{r_m}{r_w}\right) \quad (26)$$

where:

k original permeability, md
$k_m$ modified permeability, md
$r_m$ modified region radius, feet
$r_w$ wellbore radius, feet If there is no modification to the near-well permeability, s is zero. If the near-well permeability is reduced, s is greater than one. If the well is stimulated, s is less than one.

There are general rules of thumb for the effect of s on production rates. For example, when s is about −5, a well will produce at rates that are approximately 3 to 4 times greater than when s is zero. And when s is about 7, production rates are roughly half the rates that could be achieved if s was zero.

Accordingly, it is possible for those skilled in the art to estimate reasonable values for s for a CBM reservoir based upon experience and completion type. For instance, s is expected to be zero for an open-hole well drilled with water or water and air. An open-hole well drilled with mud would be expected to have a s value ranging from about 7 to about 10. But, an open-hole cavity completion in which an open-hole well is repeatedly allowed to produce at maximum rates during the completion is expected to result in a s value of about −3. Finally, hydraulic fracture stimulation theoretically can cause s values ranging from about −6 to about −4, with an average value of about −5.

When test data are unavailable, a bottom-hole pressure estimate for Equation (25) can be estimated from surface pressure and temperature data in a manner known to those skilled in the art. The average pressure can be estimated with material balance methods.

The geometrical term, $$\ln\left(\frac{r_d}{r_w}\right),$$

in Equation (25) is defined in Equation (27).

$$\ln\left(\frac{r_d}{r_w}\right) = \frac{1}{2} \ln\left(\frac{2.2458 A}{C_A r_w^2}\right) \quad (27)$$

where

A drainage area, ft$^2$
$C_A$ shape factor, dimensionless

The shape factor, $C_A$, in Equation (27) depends upon the shape of the drainage area. Values for $C_A$ are available, for example, in *Advances in Well Test Analysis* (Earlougher, R. C., Society of Petroleum Engineers of AIME; New York, p. 203–204; 1977). For example, if the well is draining a square drainage area from a central location within the square, the shape factor is 30.88.

The real gas potential in Equation (25) accounts for variation in gas properties with pressure, according to Equation (28).

$$m(p) = 2 \int_{P_b}^{P} \frac{p \, dp}{\mu_g z_g} \quad (28)$$

where p SPS pressure, psia
$\mu_g$ gas viscosity, cp
$z_g$ real gas deviation factor, dimensionless Methods for calculating $\mu_g$ and $z_g$ factors in Equation (28) can be found in literature including, for example, Whitson et al. ("Phase Behavior," Monograph Volume 20, Henry L. Doherty Series, Society of Petroleum Engineers; Chapter 3, 2000). Values can also be calculated with software, such as Huber (ibid).

Once values for $k_{eg}$ and $k_{rg}$ are determined, an estimate for $k_a$ for a particular test condition can then be calculated by dividing the corresponding $k_{eg}$ by $k_{rg}$.

Using the Calibrated Model

Calibrating the inventors' model by solving Equations (1) and (2) results in values for $\phi_{atm}$, $k_{a-atm}$, $\epsilon_{\infty i}$ and $p_{ei}$. Once calibrated, Equations (1) and (2) are used to compute $\phi$ and $k_a$ for a new reservoir condition at SPS pressures above atmospheric pressure as functions of SPS pressure and fluid composition. The $\phi$ and $k_a$ values can ultimately be used for determining the effective permeabilities to gas and water, for $k_{eg}$ and $k_{ew}$, respectively, which control movement of gas and water through the SPS. Accordingly, gas and water injectivity and production rates can be predicted.

Preferably, $k_{eg}$ and $k_{ew}$ are determined by also considering the effects on relative permeability, $k_r$. Specifically, SPS porosity changes cause changes in water and gas saturations within the SPS, which in turn lead to changes $k_r$ and $k_e$. So, although $k_e$ is the multiplication product of $k_r$ and $k_a$, the change in $k_e$ cannot necessarily be predicted by a change in $k_a$, without considering the effect on $k_r$.

For example, when a fluid is injected into a coal bed, the dynamic pressure strain component in Equation (1) increases. Specifically, the fracture aperture increases, resulting in an increased pore volume, $V_p$, in the SPS. But gas does not effectively displace water upon injection because, for example, without limitation, gas is much less viscous than water and gas is less dense than water. Therefore, the water volume, $V_w$, in the SPS remains relatively constant while $V_p$ increases. As a result, the water saturation, $S_w$, which is the ratio $V_w/V_p$, is reduced when $\phi$ increases.

Figure 2:
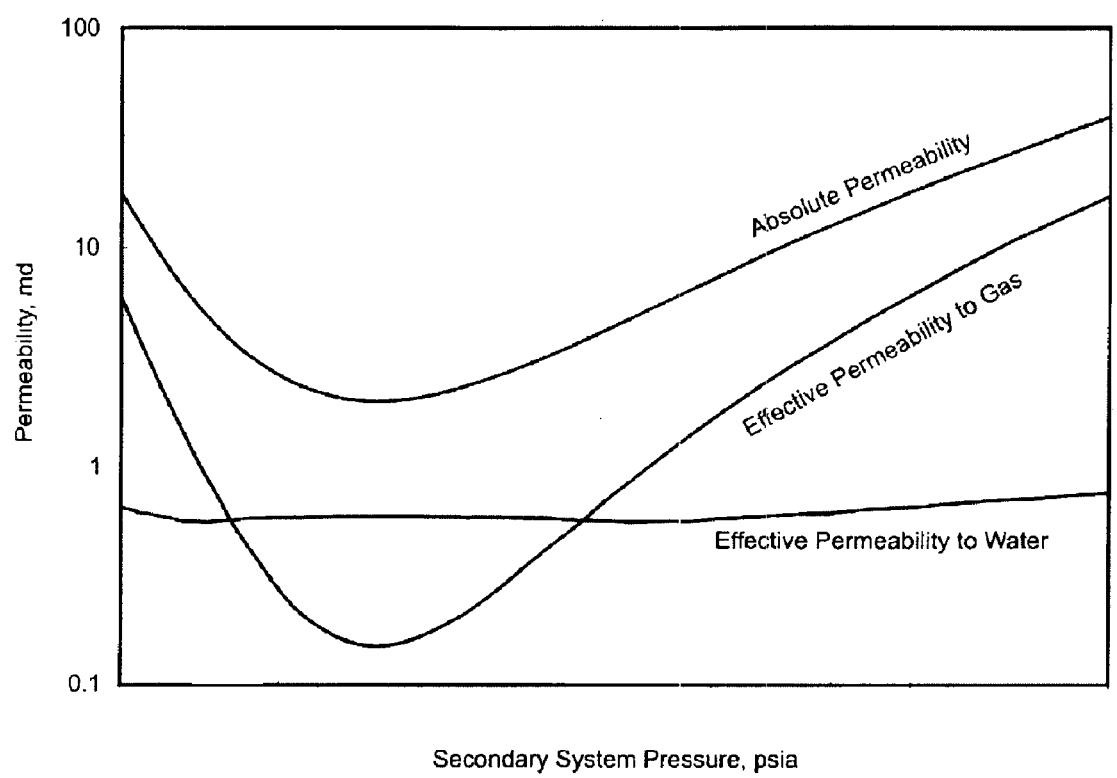
FIG. 2 is a graphical illustration of one example of the relationship between $k_a$, effective permeability to gas, $k_{eg}$, effective permeability to water, $k_{ew}$, and SPS pressure.
Figure 3:
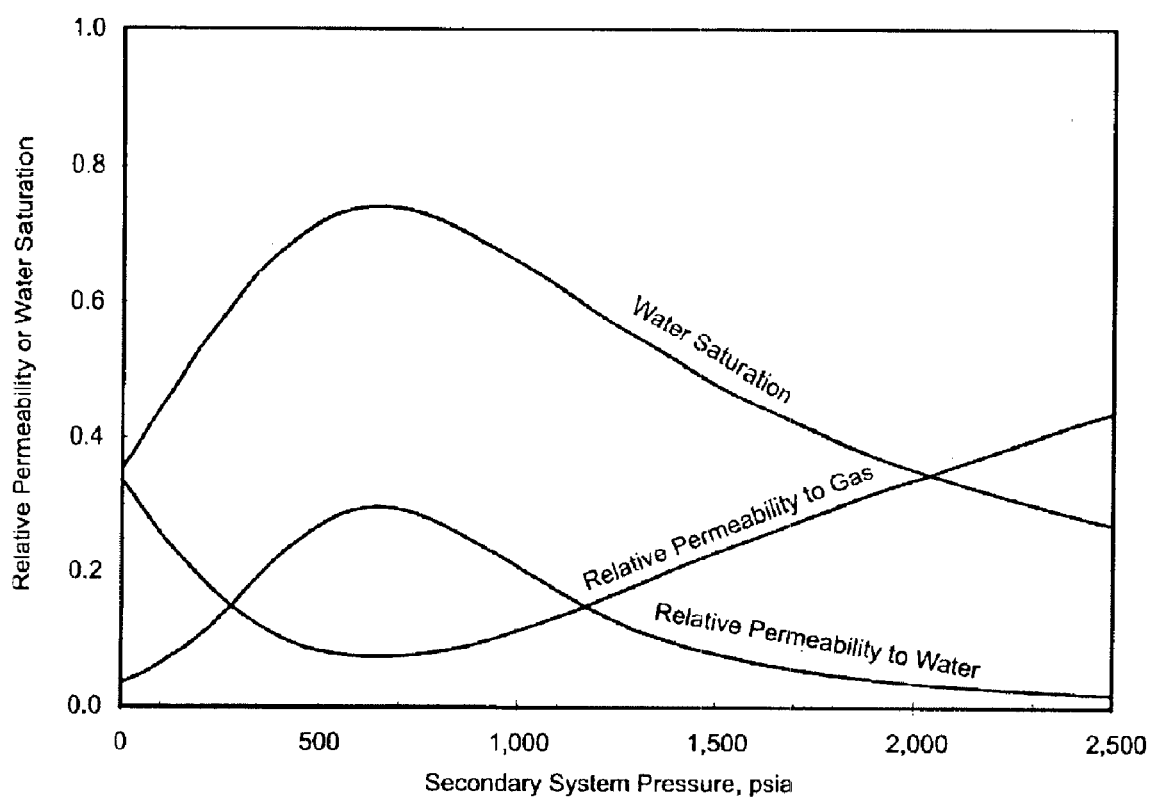
FIG. 3 is a graphical illustration of the relationship between water saturation, $S_w$, relative permeability to gas, $k_{rg}$, relative permeability to water, $k_{rw}$, and SPS pressure for the same example illustrated in FIG. 2.

FIGS. 2 and 3 illustrate the relationship of various properties to SPS pressure for a coal seam containing an example gas composed of 94.42% $CH_4$, 2.12% $CO_2$, and 3.46% $N_2$ on a mole % basis. Specifically, FIG. 2 graphically illustrates the relationship between $k_a$, $k_{ew}$, $k_{eg}$ and SPS pressure, while FIG. 3 graphically illustrates the relationship between $S_w$, relative permeability to water, $k_{rw}$, relative permeability to gas, $k_{rg}$, and SPS pressure.

Consider filling the coal by injecting a gas of the above composition. Initially, sorption strain dominates as $CH_4$ and $CO_2$ cause the coal matrix to swell, which reduces the absolute permeability from $k_{a-i}$=16.2 md to $k_a$=2.0 md at about 640 psia, as shown in FIG. 2. At greater pressures, the pressure strain increases $k_a$ to about 39.8 md at 2,500 psia.

At the same time, as shown in FIG. 3, $S_w$ increases from 0.37 to 0.74 at 640 psia as $V_p$ is initially reduced due to matrix swelling. But, as the fracture aperture increases (i.e., $V_p$ increases), $S_w$ is reduced from 0.74 at about 640 psia to 0.27 at 2,500 psia. The decrease in $S_w$, reduces $k_{rw}$, and increases $k_{rg}$.

The curve for $k_{rw}$ in FIG. 3 follows the same general trend as the curve for $S_w$ increasing from 0.040 at atmospheric pressure to 0.30 at about 640 psia. Thereafter, $k_{rw}$ decreases to 0.019 at 2,500 psia. Conversely, $k_{rg}$ decreases initially from 0.32 at atmospheric pressure to 0.075 at about 640 psia and, thereafter, increases to 0.44 at 2,500 psia. So, the trends for changes $k_{rw}$ and $k_{rg}$ were generally similar but opposite to each other. However, the changes in $k_{ew}$ were surprisingly relatively small since decreases in $S_w$ and, therefore $k_{rw}$, are almost equally offset by the increase in $k_a$ due to ballooning. As shown in FIGS. 2 and 3, changes in $k_{eg}$ parallel the $k_a$ changes as the decrease in $S_w$ increases the $k_{rg}$ at the same time that $k_a$ is increased by ballooning.

Specifically, as illustrated in the example in FIG. 2, $k_{ew}$ is relatively constant, ranging from 0.649 md to 0.581 md, in the pressure range from atmospheric to 1,500 psia, thereafter increasing gradually and slightly to 0.76 md at 2,500 psia. Accordingly, gas injection has little effect on $k_{ew}$. However, gas injection has a significant effect on $k_{eg}$. While $k_{eg}$ follows the same general trend vs. SPS pressure as does $k_a$, the magnitude of the changes in $k_{eg}$ are not as large since the presence of water causes $k_{eg}$ to be less than $k_a$. Specifically, $k_{eg}$ initially decreases from 5.25 md at atmospheric pressure to 0.15 md at about 640 psia. Thereafter, $k_{eg}$ increases to 17.4 md at 2,500 psia. FIGS. 2 and 3 therefore illustrate that gas and water flow in a coal bed cannot be determined from $k_a$ alone.

Accordingly, $k_{eg}$ and $k_{ew}$ are preferably determined by considering effects on $k_r$, first, by determining the water saturation at atmospheric pressure, $S_{w-atm}$, and then determining $S_w$ for a pre-selected SPS pressure/fluid composition condition. $S_{w-atm}$ can be estimated from the water saturation at a test condition pressure. For instance, $S_{w-atm}$ for the initial condition is determined with Equation (29):

$$S_{w-atm} = S_{w-i} \frac{\phi_i}{\phi_{atm}} \quad (29)$$

where $S_{w-atm}$ water saturation at atmospheric pressure, dimensionless $S_{w-i}$ water saturation at initial SPS pressure, dimensionless Once $S_{w-atm}$ is known, the water saturation, $S_w$, can be determined for a pre-selected SPS pressure/fluid composition condition by dividing $S_{w-atm}$ by a normalized SPS porosity determined for the pre-selected condition using Equation (1), as shown by Equation (30).

$$S_w = \frac{S_{w-atm}}{\frac{\phi}{\phi_{atm}}} \quad (30)$$

where $S_w$ water saturation, dimensionless

The $S_w$ value can then be used to determine $k_{rg}$ and $k_{rw}$ for ultimately determining $k_{eg}$ and $k_{ew}$. As shown by Equations (31) and (32), the effective permeability is the product of the absolute permeability and the relative permeability.

$$k_{eg} = k_{rg} k_a \quad (31)$$

$$k_{ew} = k_{rw} k_a \quad (32)$$

where $k_{eg}$ effective permeability to gas, md $k_{rg}$ relative permeability to gas, dimensionless $k_a$ absolute permeability, md $k_{ew}$ effective permeability to water, md $k_{rw}$ relative permeability to water, dimensionless Values for $k_{rg}$ and $k_{rw}$ are estimated as a function of $S_w$ using relative permeability data, such as the data presented in Table 2 above. The relative permeability data are obtained by either measurement on core samples, by analysis of production behavior during the life of the reservoir, or from literature data.

Thus, the inventors' calibrated model can be used to predict permeability for conditions other than for those used to calibrate the model. In this way, the model can therefore be used to predict gas and water flow through the reservoir or to predict injection pressures or rates. Moreover, the model can be used to predict permeability for different injected and/or produced fluid compositions. This is particularly useful for ECBM and sequestration processes.

For example, once $k_{eg}$ is calculated with Equation (31), the injection rate for different gas compositions can be predicted with Equation (33), a form of Darcy's Law.

$$q_g = \frac{1.987(10^{-5}) k_{eg} h T_{sc} [m(P_R) - m(P_w)]}{p_{sc} T_R \left[ \ln\left(\frac{r_d}{r_w}\right) + s \right]} \quad (33)$$

where $q_g$ gas production rate at standard conditions, Mscf/D $k_{eg}$ effective permeability to gas, dimensionless h thickness, feet
$T_{sc}$ temperature at standard conditions, 519.67° R (60° F.)
m(p) real gas potential; psia²/cp
$P_R$ reservoir pressure, psia
$P_w$ bottom-hole pressure, psia
$p_{sc}$ pressure at standard conditions, 14.69 psia
$T_R$ reservoir temperature, ° R
$r_d$ equivalent steady-state drainage radius, feet
$r_w$ wellbore radius, feet
s skin factor, dimensionless
The geometrical term, $$\ln\left(\frac{r_d}{r_w}\right),$$

in Equation (33) is defined in Equation (27), above, while m(p) is defined in Equation (28) and s is defined in Equation (26).

Use of Equation (33) for predicting the injection rate for a 50/50 mixture of $CO_2$ and $N_2$ is illustrated in Example 2 below.

For fluid compositions containing a different SAG or WAG not considered in the tests, it may be possible to estimate the characteristic sorption strain parameters for the different component using the tested SAG or WAG characteristic sorption strain parameters determined by solving Equations (1) and (2). As another alternative, sorption strain parameters may be determined by interpolating the results for WAG-$CH_4$-SAG. It may also be possible to determine a multiplier for adjusting the characteristic sorption strain parameters for a known SAG or WAG by correlating sorption strain capacity or some other relevant parameter. However, for greater accuracy, it is preferable to conduct another test for the different SAG or WAG component. Preferably, there is at least one test for each major fluid component in a pre-selected fluid composition.

Effective Conductivity Tests

As discussed above, the effective conductivity to gas and the effective conductivity to water used for determining absolute permeability may be determined from, for example, without limitation, a shut-in test, an interference test, a production test, a production test combined with a water injection/fall-off test, a production test combined with a gas injection/fall-off test, or a production test combined with a water slug test. These tests are generally known to those skilled in the art. However, for convenience, a brief description of each test is provided below.

In a production test, a well is placed on production at a substantially constant total (gas and water) production rate from a static reservoir pressure condition. The production period is preferably in a range from about 1 week to several months. During production, the bottom-hole pressure decreases proportionally to the logarithm of time. The rate of pressure decrease is proportional to the inverse of the total mobility. Total mobility, $\lambda_T$, is defined in Equation (34):

$$\lambda_T = k_a\left(\frac{k_{rg}}{\mu_g} + \frac{k_{rw}}{\mu_w}\right) \quad (34)$$

When a shut-in test (also referred to as a pressure, build-up test) is used in conjunction with a production test, the well is shut-in following production. The shut-in time is preferably in a range from about 1 to about 2 times the production period duration. As a result of shut-in, the bottom-hole pressure increases proportionally to the logarithm of time. The rate of pressure increase is proportional to the inverse of the total mobility.

A combined production/shut-in test is usually successful in moderate (5 to 20 md) to high permeability (>20 md) CBM reservoirs.

In low permeability CBM reservoirs (≦5 md), production rates may be too low or wellbore storage effects may preclude accurate analysis of the shut-in test data. As a result, gas or water injection/fall-off tests are preferably used in low permeability reservoirs and should be carefully conducted to avoid altering the original absolute permeability. Water injection rates should be relatively low for example, from about 1 gallon/minute to about 10 gallons/minute. Even with a low water injection rate, the absolute permeability may be altered during the injection portion of the test. During the fall-off portion of the test, the wellbore pressure declines back to the pre-injection reservoir pressure. Accordingly, more accurate estimates of the original absolute permeability are obtained from effective conductivity data determined during the fall-off portion of the test.

Interference tests involve multiple wells. Generally one well is an active well and is placed on production at a relatively constant total rate. The second well is an observation well that is not produced but in which bottom-hole pressure is measured with sensitive pressure transducers as a function of time. The rate of pressure change in the observation well is proportional to the logarithm of time and inversely proportional to the total mobility. More than one observation well can be used and results in estimates of effective conductivity distributions rather than just a single value.

If used, an interference test is preferably conducted prior to SAG injection. If an interference test is used after SAG injection starts, the test should be conducted before the injected SAG has reached the observation well. More specifically, the interference test should be conducted before the injected SAG front is less than approximately half the distance between the injection well and the observation well.

Water injection tests are commonly performed in coal seams. This test involves injecting water at a low constant rate (i.e. gallons per minute) for a period of time. Injection is usually performed with low volume, high-pressure pumps commonly available in the industry. The pressure data behave similarly to a production test except bottom-hole pressure increases rather than decreases during the test. A water injection test can be followed by a falloff test during which injection is halted. The fall-off test pressure data behave similarly to a shut-in test except that bottom-hole pressure decreases rather than increases.

Slug tests are variations on water injection tests and are performed in reservoirs that have an average pressure that is less that the hydrostatic head of water to surface. In this test, a "slug" of water is rapidly poured into the well. The water level in the well slowly decreases until the hydrostatic head of the water is equal to the reservoir pressure.

Gas injection tests are less common than water injection tests due to higher costs. These tests usually involve injecting $N_2$ using hydraulic fracture stimulation equipment. As in the case of a water injection test, bottom-hole pressure increases during injection and decreases when injection ceases. During gas injection, the gas rates should be relatively low, for example, from about 500 to about 1,000 scf/minute. The rate may alter $k_a$ and, therefore, the gas fall-off portion of the test should provide a more accurate estimate of the original $k_a$. Gas injection tests can be conducted when the SPS is completely filled with water.

Injection increases the near-well SPS pressure that in turn decreases the near-well gas saturation allowing sufficient effective permeability to gas for injection.

Various combinations of these tests are possible. The selected variation depends upon the production type (i.e. gas and/or water productive), and the reservoir pressure, among other parameters.

Test Procedures

The claimed process may be applied to a single well or to multiple wells. In a single well test, the injection and production test conditions are conducted at the same well. When two or more wells are used, the injection test may be performed in one or more wells and the production test may be performed in one or more other different wells. Alternatively, injection and production tests may be conducted at each well. Preferably, the claimed process is used with two or more wells in the same coal seam. More preferably, the injection and production tests are conducted in the same well. Most preferably, both the injection and production tests are performed in each of two or more different wells, since coal seams are heterogeneous. When two or more wells are used, the wells are preferably in close proximity to each other. For example, typical production inter-well spacing ranges, from about 0.25 to about 0.7 miles. In some special cases involving interference tests, wells could be within about 100 to about 200 feet of each other.

The test procedures may be applied to new wells or to existing injection or production wells. In the event that an existing well is used, fluid composition data is mostly likely available from earlier production. The existing well is then shut-in to provide the estimates for effective and absolute permeability, $S_w$, and the average SPS pressure. The properties determined at for the existing well after shut-in are the values that are used for the initial test conditions described above under "Determining Initial Absolute Permeability." As a further advantage, the shut-in also allows pressures and fluid compositions to equilibrate prior to injecting a test fluid.

As discussed above, the dynamic pressure strain component is calibrated by injecting a fluid at a pressure greater than $P_R$. The injection fluid is preferably water or WAG. More preferably, the injection fluid is water. Most preferably, the dynamic pressure strain component is calibrated by first injecting water, and then injecting a WAG.

Because coal seams exhibit heterogeneities, the porosity and permeability may be different for different wells. Where differences exist and multiple wells are used, average values for $\phi_{atm}$ and $k_{a-atm}$ should be used in subsequent porosity and permeability predictions for portions of the coal bed further away from the test wells.

Preferred procedures for conducting single well and multiple well tests, using tests and analyses described more fully above, are now outlined, for an example of using water and WAG as injection fluids in the injection tests and a SAG production test. When each well in a multiple well test is used for both SAG and WAG injection, then the single well test procedure should be used for each well.

Single Well Test Procedure

In a single well test, WAG injection may be followed by SAG injection or SAG injection may be followed by WAG injection. However, because SAG causes coal to swell, water and/or WAG is preferably injected prior to SAG.

1. For a shut-in well, measure the initial $P_R$ and reservoir temperature, $T_R$, before production or injection begins. $P_R$ and $T_R$ are typically measured by running a pressure/temperature transducer on wireline to the depth of the completed reservoir of interest. If the well is on production, shut-in the well and determine initial (average) pressure and temperature during Step 2 below.

2. Conduct tests to estimate $k_{a-i}$ at the original in-situ gas composition without altering $P_R$ and $T_R$. As discussed more fully above, under "Determining Initial Absolute Permeability," $k_{a-i}$ is preferably estimated by determining the effective conductivity to gas, the effective conductivity to water and the coal thickness.

3. If, in Step 2, a combined production/shut-in test was used to determine effective conductivity, the well is preferably reconfigured with an injection string (a packer set downhole on tubing which is landed in the wellhead) and a wellhead is installed. However, the wellbore configuration can remain the same as for the production/shut-in test. If a water injection test was used to determine effective conductivity, the same wellbore configuration used for the water injection test can be used for Step 4.

4. Inject water into the wellbore and follow it with a falloff (shut-in) period. Preferably, the injection pressure is less than the fracture extension pressure, $P_E$. More preferably, water is injected at a pressure less than the fracture pressure, $P_F$. The injection and falloff periods should be performed for sufficient time and volume to account for wellbore storage effects.

5. Inject a WAG into the wellbore. Preferably, the injection pressure is less than the fracture extension pressure, $P_E$. More preferably, WAG is injected at a pressure less than the fracture pressure, $P_F$. The injection period should be performed for sufficient time and volume to account for wellbore storage effects and to obtain the desired WAG sorption area.

6. Shut in the wellbore for the soak period. Preferably, the length of the soak period is based upon sorption times as previously discussed under "Calibrating Pressure Strain Component." More preferably, the soak period is at least about 1.5 times the length of the injection period so that estimates of the average pressure, effective conductivity to gas and water, and water saturation after injection can be obtained. The well may be shut-in downhole or at the wellhead. Preferably, the well is shut-in downhole to reduce wellbore storage effects. For example, the well may be shut-in by setting a plug on wireline into a nipple located above the pressure transducer monitoring position.

7. Unseat the packer and remove the injected fluid from the wellbore. Injected fluid is removed from the wellbore so that the composition of the gases produced in Step 10 is representative of the stabilized composition in the SPS. Preferably, the injected fluid is removed by circulating completion fluid in such a way that the bottom-hole pressure during circulation is just slightly greater than $P_R$. Suitable completion fluids include, without limitation, water for normal-pressured or under-pressured reservoirs, and sodium chloride, potassium chloride, or calcium chloride brines for over-pressured reservoirs. If the reservoir is under-pressured, (i.e., $P_R$ is less than the hydrostatic head of water to surface) water will be lost to the reservoir during and after circulation. Water lost to the reservoir will not compromise the test procedure.

8. Install downhole production equipment. Preferably, downhole production equipment is installed without allowing the well to produce. However, small amounts of production can be tolerated during this step. In over-pressured reservoirs, this step may not be necessary and the injection packer can remain in the seated position or be unseated allowing production up either the tubing, tubing-casing annulus, or both. In normal- or under-pressured reservoirs, the completion fluid will usually prevent the well from flowing. The injection string is removed from the wellbore and a production string, including tubing, and a downhole pump, is installed in the wellbore. Preferably, a pressure transducer is also installed so that the bottom-hole pressure can be monitored directly. Alternatively, bottom-hole pressure during production can be estimated from surface pressure and the height of water or completion fluid remaining in the wellbore with methods known to those skilled in the art.

9. Conduct a soak period to allow the near-well free gas composition to reach equilibrium with the sorbed gas composition. The duration of this soak period is discussed above under "Calibrating Pressure Strain Component."

10. Return the well to production. During the production period, bottom-hole pressure and temperature, surface pressure and temperature, surface gas and water production rates, and gas and water composition are determined as a function of time. The duration of the production time is discussed above under "Calibrating Pressure Strain Component."

11. Optionally, shut-in the well for sufficient time to obtain data required for post-WAG injection permeability estimates.

12. Reconfigure the well for injection if necessary. For an over-pressured reservoir, this step may not be required if the injection packer was not unseated. If the packer was unseated, it will have to be reseated. Reseating will often require that completion fluid is circulated to increase the wellbore pressure to a pressure greater than $P_R$ so that the wellhead can be safely removed. For a normal- or under-pressured reservoirs, the well will often have to be circulated with completion fluid (i.e., water) so that the wellhead and production equipment can be safely removed. The injection string including the packer and pressure transducer will be rerun into the well. The packer will be seated and the wellhead reinstalled.

13. Inject a SAG into the wellbore. Preferably, the injection pressure is less than the fracture extension pressure, $P_E$. More preferably, SAG is injected at a pressure less than the fracture pressure, $P_F$. The injection period should be performed for sufficient time and volume to account for wellbore storage effects and to obtain the desired SAG sorption area 14. Repeat Step 6.

15. Repeat Step 7.

16. Repeat Step 8.

17. Conduct a soak period to allow the near-well free gas composition to reach equilibrium with the sorbed gas composition. The duration of this soak period is discussed above under "Calibrating Sorption Strain Component."

18. Return the well to production. During the production period, bottom-hole pressure and temperature, surface pressure and temperature, surface gas and water production rates, and gas and water composition are determined as a function of time. The duration of the production time is discussed above under "Calibrating Sorption Strain Component."

19. Optionally, shut-in the well for sufficient time to obtain data required for post-SAG injection permeability estimates.

20. Optionally, conduct a final water injection/fall-off test in the manner described above under "Effective Conductivity Tests."

Multiple Well Test Procedure

The use of multiple wells can reduce the time required for collecting data because WAG and SAG injection tests can be performed concurrently. However, $k_{a-i}$ is preferably determined independently for each well, due to heterogeneity in the coal seam. As stated above, if multiple wells are used, but SAG and WAG are injected into each well, then the procedure under "Single Well Test Procedure" should be used for each well. The procedure outlined below is used when WAG is injected in one or more wells and SAG in injected in one or more different wells.

WAG Well Test Procedure

See Steps 1–11 under "Single Well Test Procedure." Optionally, additionally, conduct a final water injection/fall-off test in the manner described above under "Effective Conductivity Tests."

SAG Well Test Procedure

See Steps 1–11 under "Single Well Test Procedure" with the exception that SAG is injected rather than WAG in Step 5. In Steps 6 and 9, use sorption times discussed under "Calibrating Sorption Strain Component." Optionally, additionally, conduct a final water injection/fall-off test in the manner described above under "Effective Conductivity Tests."

The following non-limiting examples of embodiments of the present invention that may used as claimed herein are provided for illustrative purposes only.

EXAMPLE 1

Example 1 illustrates how the inventors' model described in Equation (1) can be calibrated. However, it should be noted that the data were collected before the inventors' model and method were developed. Accordingly, this example is not the most preferred method for calibrating the inventors' model. But, even though the data was not collected by the preferred method, Example 1 illustrates how even less than preferred information can be used successfully to predict permeability and porosity changes.

Well test data was collected from two wells located near the town of Big Valley, Alberta, Canada. Both wells in this example were completed in an Upper Medicine River Coal seam located in the Mannville Formation at depths between 4,117 ft. and 4,130 ft. below the surface. The first well was used to calibrate the dynamic multicomponent sorption strain component of the model. The second well was used to calibrate the dynamic pressure strain component of the model.

First Well (FBV 4A)

The first well was the FBV 4A-23-36-20 W4M (FBV 4A) well located 3 km (1.9 mi) north of Big Valley. An initial combined production/shut-in test was conducted to obtain estimates of $P_R$, initial effective conductivities, and initial gas composition. Following these test procedures, $CO_2$ was injected into the formation through the FBV 4A well. The well was returned to production after a soak period. $P_R$, post-SAG effective conductivities and post-SAG gas composition estimates were determined with a second combined production/shut-in test.

The initial production/shut-in test data were evaluated using the method described above under "Determining Initial Absolute Permeability." This analysis resulted in estimates for the initial pressure, $P_R$ (1,146 psia), the effective conductivity to gas, $k_{eg-i}h$ (6.93 md-ft), and the effective conductivity to water, $k_{ew-i}h$ (7.51 md-ft). Analysis of density log data determined that the coal thickness (h) was 13.1 ft. Accordingly, dividing the respective initial effective conductivity estimates by the coal thickness resulted in $k_{eg-i}$ (0.529 md) and $k_{ew-i}$ (0.573 md) estimates. The initial effective gas-water permeability ratio, $k_{eg-i}/k_{ew-i}$, was therefore 0.923 (0.529/0.573). Because $k_{a-i}$ is the same for both gas and water, the initial relative permeability ratio, $k_{rg-i}/k_{rw-i}$, was equal to $k_{eg-i}/k_{ew-i}$, 0.923. Using $k_{rg-i}/k_{rw-i}$ and interpolating the data in Table 2 above, $S_{w-i}$, $k_{rg-i}$ and $k_{rw-i}$ were determined to be 0.60, 0.145, and 0.158, respectively. The initial absolute permeability $k_{a-i}$ was determined by dividing $k_{eg-i}$, 0.529 md, by $k_{rg-i}$, 0.145, to obtain a value of 3.66 md.

During the production portion of the initial production/shut-in test, the initial produced gas composition was analyzed by gas chromatography and determined to be 92 mol. % $CH_4$, 1.5 mol. % $CO_2$, 5 mol. % $N_2$, and 1.5 mol. % ethane ($C_2H_6$) plus propane ($C_3H_6$). Although this initial gas composition could have been used for calibrating the inventors' model, it was more accurate to use the initial gas composition from the second well because the composition produced from the FBV 4A well had been contaminated by $CO_2$ injection during hydraulic fracturing and two $N_2$ injections early in the well life. Nonetheless, the inventors expect that the contaminated gas composition data could have been used with little effect upon the permeability estimates or the strain parameters.

A total of 3.290 MMscf of $CO_2$ (SAG) were injected into the well in 12 separate injection periods over 22 days. Of this total, 3.23 MMscf entered the coal seam and 0.06 MMscf remained in the wellbore. The injected $CO_2$ was contained within an area of 0.384 acres. If the $CO_2$ swept area was a circle, the edge of the $CO_2$ front would have been 73 feet from the well. The FBV 4A was then shut-in for a 40-day soak period to allow the in-situ post-SAG gas composition to stabilize.

The FBV 4A well was returned to production to perform a combined production/shut-in test. The well was produced for 59 days. The post-SAG produced gas composition was determined by gas chromatography. At the beginning of production, the post-SAG produced gas composition was 30.5 mol. % $CH_4$, 68.2 mol. % $CO_2$, 0.9 mol. % $N_2$, and 0.3 mol. % $C_2H_6+C_3H_8$. $CO_2$ concentration decreased with continued production while $CH_4$, $C_2H_6+C_3H_8$, and $N_2$ concentration increased. At the end of the production period, the post-SAG produced gas composition was 62.3 mol. % $CH_4$, 34.0 mol. % $CO_2$, 2.5 mol. % $N_2$, and 1.2 mol. % $C_2H_6+C_3H_8$. The post-SAG produced gas composition from the end of the production period was used as the post-SAG free gas composition for purposes of estimating the corresponding sorbed gas composition and sorption isotherm parameters using Equations (17), (18), and (19). The post-SAG free gas and sorbed gas compositions are presented below in Table 5.

The FBV 4A well was then shut-in and the shut-in pressure data were evaluated in a similar manner as for the test conducted before $CO_2$ injection. $P_R$ was unchanged by injection and remained at 1,146 psia. Estimates of the effective conductivity to gas after SAG injection, $k_{eg-SAG-p}h$, and the effective conductivity to water after SAG injection, $k_{ew-SAG-p}h$, were 2.23 and 1.57 md-ft, respectively. The effective permeability to gas and water were determined by dividing by the coal thickness of 13.1 ft, resulting in $k_{eg-SAG-p}$ equal to 0.17 md and $k_{ew-SAG-p}$ equal to 0.12 md. The corresponding effective gas to water permeability ratio, $k_{eg-SAG-p}/k_{ew-SAG-p}$, was 1.42 (0.17/0.12). Because $k_{a-SAG-p}$ is the same for both gas and water, $k_{rg-SAG-p}/k_{rw-SAG-p}$ was also equal to 1.42. Using $k_{rg-SAG-p}/k_{rw-SAG-p}$ and interpolating the data in Table 2 above, $S_{w-SAG-pi}$, $k_{rg-SAG-p}$, and $k_{rw-SAG-p}$ were determined to be 0.56, 0.173, and 0.124, respectively. The absolute permeability after SAG injection, $k_{a-SAG-p}$ was determined by dividing $k_{eg-SAG-p}$, 0.17 md, by $k_{rg-SAG-p}$, 0.173, to obtain a value of 0.98 md.

Second Well (FBV 5)

The second well was the FBV 5–23-36-20 W4M (FBV 5) located 493 m (1,617 ft) north of the FBV 4A well. Core samples, density log data and a primary production test were used to obtain Langmuir isotherm data, coal thickness, $P_R$, effective conductivities and initial gas composition data. The well was then shut-in and then $N_2$ (WAG) was injected. The well was shut-in and then returned to production.

The FBV 5 well was cored while drilling to obtain fresh samples for coal property measurements. In particular, measurements of sorption isotherm data were obtained to predict sorbed gas composition and storage capacity. The core samples were analyzed by TerraTek, Inc., Salt Lake City, Utah, U.S.A., using the procedures described in Mavor et al. (SPE 20728, ibid). The Langmuir parameters from these measurements are summarized in Table 3.

TABLE 3

| Parameter | Units | $CH_4$ | $CO_2$ | $N_2$ |
|---|---|---|---|---|
| In-Situ Langmuir Storage Capacity ($G_{si}$) | scf/ton | 376.8 | 772.1 | 373.6 |
| Langmuir Pressure ($p_{Li}$) | psia | 680 | 276 | 3,951 |

After drilling through the coal seams, the FBV 5 well was logged. Interpretation of the density log data indicated that the coal seam thickness was very similar to that penetrated by the FBV 4A well, 4.0 m (13.0 ft).

The FBV 5 well was placed on production for 28 days. Surface and bottom-hole temperature and pressure data, gas and water production rate data, as well as initial gas composition, were determined. The initial produced gas contained 94.42 mol. % $CH_4$, 0.26 mol. % $CO_2$, 3.46 mol. % $N_2$, 1.53 mol. % $C_2H_6$, and 0.33 mol. % $C_3H_8$ and heavier hydrocarbon fractions. This initial gas composition was believed to be more reliable than the FBV 4A initial gas composition data since no gases had been injected into the FBV 5 well before this composition was determined. As shown in Table 5, the FBV 5 initial produced gas was used as the initial free gas composition for both the FBV 4A and FBV 5 tests.

Gas and water production rates were 4 Mscf/D and 8 STB/D, respectively. In this case, the $k_{rg-i}/k_{rw-i}$ ratio was determined from production data, as discussed above under the section entitled "Determining Permeability Values from Production Data," using Equation (24). Values for $\mu_g$ and $B_g$ were computed using the Huber (ibid) computer program, resulting in values of 0.0136 cp and 0.0131, respectively. The corresponding water values, determined from Brill et al. (ibid), were 0.614 cp ($\mu_w$) and 1.0 ($B_w$), respectively. Using these values in Equation (24), $k_{rg-i}/k_{rw-i}$ was calculated to be 0.0258. Interpolation of Table 2 above resulted in estimates of $S_{w-i}$, $k_{rg-i}$, and $k_{rw-i}$ of 0.910, 0.016, and 0.628, respectively. These data were used in combination with later data to obtain absolute permeability estimates.

Following production, the FBV 5 well was shut-in to obtain data suitable for permeability and pressure estimates.

However, because the well was shut-in at the surface and the coal seam was a low permeability coal (see "Effective Conductivity Tests" above), wellbore effects dominated the pressure behavior and the data were not suitable for analysis. As a result, a water injection-falloff test was performed to estimate the absolute permeability at the initial reservoir pressure. From the water injection-falloff test, $k_{ew}$ was determined from the falloff data to be 0.735 md. This estimate was obtained as $P_R$ returned to the initial pressure and, therefore, was believed to be a reliable indicator of the effective permeability to water, $k_{ew-i}$, during the preceding production period. The water injection-falloff test was also used to determine a value for M, as discussed more fully below.

In some cases, water can effectively displace gas, but in this test the inventors assumed that water did not displace gas, since the gas saturation before water injection was only 0.09. At such a low gas saturation, it was possible that injected water did not enter the relatively small portion of the SPS occupied by gas. As a result, rather than using water permeability values, the inventors estimated the absolute permeability at the initial pressure, $k_{a-i}$, by dividing the effective permeability to water $k_{ew-i}$ (0.735 md), by the relative permeability to water determined from the production rates, $k_{rw-i}$, (0.628), to obtain an estimate of 1.2 md for $k_{a-i}$ for the FBV 5 well. The corresponding $k_{eg-i}$ was 0.019 md, calculated by the product of $k_{rg-i}$ (0.016) and $k_{a-i}$ (1.2 md).

The injection portion of the water injection test was used to obtain estimates of the constrained axial modulus, M. The pressure at the end of the injection period was 1,925 psia. Analysis of the injection data resulted in an estimate of the effective permeability to water, $k_{ew-H2O-inj}$, equal to 5.45 md. As the gas saturation was low, the inventors assumed that water did not enter the pore spaces where gas was present and displace gas. However, while the gas volume may have been constant, the porosity was increased resulting in a smaller gas saturation and greater effective permeability to water. The gas saturation during injection can be estimated with Equation (35).

$$S_{g-2} = S_{g-1}\frac{\phi_1}{\phi_2} = S_{g-1}\left(\frac{k_{a-1}}{k_{a-2}}\right)^{\frac{1}{3}} \quad (35)$$

where $S_{g-1}$ gas saturation before injection, fraction of SPS volume $S_{g-2}$ gas saturation during injection, fraction of SPS volume $k_{a-1}$ absolute permeability before injection, md $k_{a-2}$ absolute permeability during injection, md Equation (35) can be solved iteratively for $k_{a-2}$ and $S_w$ during injection. For example, if $k_{rw}$ during injection was initially assumed to be one, $k_{a-2}$ becomes 5.45 with $k_{a-1}$ of 1.2 md. Therefore the gas saturation during injection, $S_{g-2}$, was 0.0543. At this gas saturation, $k_{rw}$ was 0.7198 based upon Table 2. Therefore, $k_{a-2}$ became 7.57 md and $S_{g-2}$ became 0.04878. Iteration for this example continued until $S_{g-2}$ became 0.0493, $k_{rw}$ became 0.733 and $k_{a-2}$ became 7.43 md. The final porosity ratio ($\phi_2/\phi_1$) was 1.836 indicating that the porosity during water injection was 0.0022.

As discussed earlier, the absolute permeability during an injection test occurs at an average of the pressure within a region affected by the injection test. It would be possible to estimate precisely this pressure by integrating pressure distributions surrounding the injection well that are calculated, for example, with a reservoir simulator. For brevity in this example, the inventors chose to approximate the average pressure within the affected region by the average of the bottom-hole pressure at the end of injection and the reservoir pressure. For this example, with a final bottom-hole injection pressure of 1,943 psia and a reservoir pressure of 1,146 psia, the pressure corresponding to 7.43 md is 1,545 psia.

Combining the absolute permeability estimates obtained during and after water injection (7.43 and 1.2 md, respectively) at an average pressure, $\bar{p}_{inj}$, of 1,545 psia and the porosity estimate obtained from the water production data (0.0012 as discussed later) allowed M to be estimated with Equation (15). The resulting estimate was 397,600 psi. If a value for v is assumed (such as 0.21 published by Mavor and Vaughn (ibid)), a value for E can be estimated. For this example, E was 353,210 psi based upon a v of 0.21.

A $N_2$ injection test of the FBV 5 well was conducted to determine a value for $k_{a-WAG-inj}$. $N_2$ stimulation equipment was rigged up on the wellhead. A total of 293 Mscf $N_2$ was pumped into the well over 7.1 hours. Of this total 245 Mscf entered the coal seam and 48 Mscf remained in the wellbore. The injection pressure at the end of the test was 2,262 psia. The $N_2$ was contained within an areal extent of 0.217 acres. If the area was circular, the outer edge of the swept region was 54.9 feet from the well. The FBV 5 well was shut-in to conduct a falloff test and remained shut-in for nine days.

The injection data were evaluated to determine estimates of the effective permeability to gas at the WAG injection pressure, $k_{eg-WAG-inj}$, which was 3.9 md. As previously discussed, gas injection has little effect upon the effective permeability to water. As a result, the effective permeability to water at the WAG injection pressure, $k_{ew-WAG-inj}$ was the same as obtained from the preceding water falloff test ($k_{ew-i}$=0.73 md). The resulting $k_{eg-WAG-inj}/k_{ew-WAG-inj}$ ratio was therefore 5.3. Interpolation of Table 2 above resulted in estimates of the WAG injection water saturation, $S_{w-WAG-inj}$, the relative permeability to gas at the WAG injection pressure, $k_{rg-WAG-inj}$, and the relative permeability to water at the WAG injection pressure, $k_{rw-WAG-inj}$, equal to 0.415, 0.282, and 0.054, respectively. Dividing $k_{eg-WAG-inj}$ by $k_{rg-WAG-inj}$ resulted in an estimated $k_{a-WAG-inj}$ equal to 13.8 md.

The FBV 5 well was returned to production for nine days. Gas and water rates at the end of the production period were 4.1 Mscf/D and 7.9 STB/D, respectively, which were very similar to the production rates before $N_2$ injection, indicating that $N_2$ injection did not significantly change $P_R$, effective permeability to gas and water, or $S_w$ around the wellbore. The FBV 5 post-WAG injection produced gas composition at the beginning of the production period contained 30 mol. % $CH_4$ and 70 mol. % $N_2$. This composition was assumed to be the same as that for the in-situ gas at the end of the injection, the time of the injection pressure measurement.

Calibrating the Model

The FBV 4A-SAG and the FBV 5-WAG tests resulted in sufficient data to calibrate the inventors' model. Table 4 summarizes the parameter estimates discussed above. These values were maintained constant during the calibration procedure. As discussed below, porosity estimates were independently obtained for FBV 4A and FBV 5 before injection with reservoir simulation methods and were not changed during the calibration procedure. The SPS porosity estimate after $CO_2$ injection was determined using the FBV 4A absolute permeability ratio before and after $CO_2$ injection in Equation (20). And the SPS porosity estimate during $N_2$ injection was determined using the FBV 5 absolute permeability ratio before and during $N_2$ injection in Equation (20). These SPS porosity estimates were maintained constant during calibration.

reservoir. The FBV 4A and FBV 5 $\phi_i$ estimates were used for calibrating the inventors' model in Equation (1).

As discussed earlier, the water injection test conducted in FBV 5A was used to calibrate the constrained axial modulus,

TABLE 4

| Parameter | Units | FBV 4A: Before $CO_2$ Injection | FBV 4A: After $CO_2$ Injection | FBV 5: Before $N_2$ Injection | FBV 5: During $H_2O$ Injection | FBV 5: During $N_2$ Injection |
|---|---|---|---|---|---|---|
| $P_R$ | psia | 1,146 | 1,146 | 1,146 | 1,146 | 1,146 |
| $\bar{p}_{inj}$ | psia | — | — | — | 1,943 | 2,262 |
| $p_{inj}$ | psia | — | — | — | 1,545 | 1,704 |
| $\phi$ | — | 0.002 | 0.00129 | 0.0012 | 0.0022 | 0.0027 |
| $k_a$ | md | 3.66 | 0.98 | 1.204 | 7.43 | 13.8 |
| $k_{eg}$ | md | 0.529 | 0.17 | 0.019 | 0.074 | 3.9 |
| $k_{ew}$ | md | 0.573 | 0.12 | 0.73 | 5.45 | 0.730 |
| $S_w$ | — | 0.6043 | 0.5613 | 0.9101 | 0.9511 | 0.4151 |
| $k_{rg}$ | — | 0.1445 | 0.1725 | 0.0158 | 0.01 | 0.2823 |
| $k_{rw}$ | — | 0.1580 | 0.1246 | 0.628 | 0.733 | 0.0544 |

The other known data include the free gas composition for each test condition. These data were used to estimate the sorbed gas composition for each test condition based upon the sorption isotherm parameters and were performed with extended Langmuir isotherm theory using Equations (17), (18), and (19). For simplicity, the gas composition was limited to three components, $CH_4$, $N_2$, and $CO_2$. The heavier hydrocarbons were accounted for by adding to the $CO_2$ value. This simplification had little effect upon the calculations because the hydrocarbons are also SAGs and were present in only small concentrations. Table 5 summarizes the free and sorbed gas compositions.

TABLE 5

| Parameter | FBV 4A Before $CO_2$ Injection | FBV 4A After $CO_2$ Injection | FBV 5 Before $N_2$ Injection | FBV 5 During $N_2$ Injection |
|---|---|---|---|---|
| Free Gas Composition (mole frac.) | | | | |
| $CH_4$ Concentration | 0.9442 | 0.6230 | 0.9442 | 0.3000 |
| $CO_2$ Concentration | 0.0212 | 0.3520 | 0.0212 | 0.0000 |
| $N_2$ Concentration | 0.0346 | 0.0250 | 0.0346 | 0.7000 |
| Sorbed Gas Composition (mole frac.) | | | | |
| $CH_4$ Concentration | 0.8932 | 0.2591 | 0.8932 | 0.7152 |
| $CO_2$ Concentration | 0.1012 | 0.7391 | 0.1012 | 0.0000 |
| $N_2$ Concentration | 0.0056 | 0.0018 | 0.0056 | 0.2848 |

An estimate of the SPS porosity at initial pressure, $\phi_i$, for the coal surrounding the FBV 4A well was obtained by reservoir simulation using the GEM™ (Version 2002.10) CBM software available from Computer Modeling Group, Calgary, Alberta, Canada. A simulation model was constructed that honored all well test analysis results, sorption isotherm data, and gas composition data. The SPS porosity included in the simulation model was adjusted to obtain a match with water production rates. The SPS porosity and absolute permeability were constant over the short duration of the simulated production period. The resulting estimate for the FBV 4A $\phi_i$ was 0.002, i.e., 0.2% of the bulk volume of the reservoir.

Likewise, GEM™ was used to determine an estimate for $\phi_i$ for the coal surrounding the FBV 5 well. The SPS porosity included in the model was revised to obtain a match with water production rates. The resulting estimate for the FBV 5 $\phi_i$ was 0.0012, i.e., 0.12% of the bulk volume of the M, value used in the model to 397,600 psi. The sorption strain calibration is affected by the value of Poisson's Ratio, $\nu$, as will be shown in Example 3. Independent estimates of Young's Modulus, E, and Poisson's Ratio, $\nu$, for Upper Medicine River coal samples are unavailable to the inventors' knowledge. As a result, the inventors used a $\nu$ value measured on San Juan Basin coal samples from SPE 39105 (Mavor et al., ibid) of 0.21, resulting in an estimate for E equal to 353,210 psi. The bulk modulus, K, calculated using Equation (16) was 202,994 psi. The rock mechanical properties, the porosity estimates and the test SPS pressures at either the reservoir pressure or the average pressure of the injection zone were used in Equation (21), resulting in a total multicomponent volumetric sorption strain difference of −0.001448 between the FBV 4A tests after and before $CO_2$ injection and 0.000211 between the FBV 5 tests during and before the $N_2$ injection.

The parameters that were expected to be changed while calibrating the model were the characteristic volumetric sorption strain at infinite pressure, $\epsilon_{\infty\text{-}CH4}$, for $CH_4$, and the pressures at 50% $\epsilon_{\infty i}$, $p_{\epsilon i}$, for each gas component. An initial value of $\epsilon_{\infty\text{-}CH4}$=0.01 was selected for the $CH_4$ characteristic sorption strain parameter, similar to that published by Levine (ibid).

An average of the $p_{\epsilon i}$ values for $CH_4$ (705 psia) and $CO_2$ (386 psia) published by Levine (ibid) were used as initial estimates. In general $p_{\epsilon i}$ values for $N_2$ are expected to be greater than for $CH_4$ based upon sorption isotherm data. Accordingly, $P_{\epsilon\text{-}N2}$ was assumed to be 1,200 psia. Once the $p_{\epsilon i}$ values were specified, the characteristic volumetric sorption strain parameter for $CO_2$, $\epsilon_{\infty\text{-}CO_2}$=0.01117, was computed with Equation (22) and the characteristic sorption strain parameter for $N_2$, $\epsilon_{28\text{-}N_2}$=0.00592 was computed with Equation (23).

The values in Tables 4 and 5, and the estimated values for E, $\nu$, $\epsilon_{\infty}$, $p_{\epsilon}$, and $\phi$ were used in Equation (1) to produce values for $\phi_{atm}$ for initial, WAG injection and SAG production conditions. Values for $k_{a\text{-}atm}$ for each condition were also calculated using Equation (2) with the respective $\phi_{atm}$ value and the $k_a$ value from Table 4. The results for the first iteration are presented in Table 6.

TABLE 6

| Parameter | Units | FBV 4A: Before $CO_2$ Injection | FBV 4A: After $CO_2$ Injection | FBV 5: Before $N_2$ Injection | FBV 5: During $N_2$ Injection |
|---|---|---|---|---|---|
| Pressure | psia | 1,146 | 1,146 | 1,146 | 1,704 |
| $\phi$ at Pressure | — | 0.002 | 0.00129 | 0.0012 | 0.0027 |
| $\phi/\phi_{atm}$ ratio | — | 0.8998 | 0.5983 | 0.8434 | 1.8653 |
| $\phi_{atm}$ | — | 0.00222 | 0.002158 | 0.001423 | 0.01451 |
| $k_{a\text{-}atm}$ | md | 5.03 | 4.60 | 2.01 | 2.13 |

As shown in Table 6, the values for $\phi_{atm}$ for each test condition were within 2 to 3% of each other and the values for $k_{a\text{-}atm}$ for each test condition were within 6 to 9% of each other. Accordingly, the estimated values for $\epsilon_{\infty\text{-}CH4}$ and $p_{\epsilon i}$ values were adjusted iteratively in the manner described above under "Selecting Sorption Strain & SPS Porosity Values." The inventors used a Microsoft® Excel™ spreadsheet to assist in the iterative computation. The iteration continued until substantially equal values for $\phi_{atm}$ and $k_{a\text{-}atm}$ were independently obtained for each of the test conditions. $\phi_{atm}$ values were within 1% or less and $k_{a\text{-}atm}$ values were within 3% or less.

Table 7 lists the ultimate estimates for strain parameters used in the final iteration, while Table 8 summarizes estimates for $\phi$, $\phi_{atm}$ and $k_{a\text{-}atm}$ based upon E and v values of 353,210 psi and 0.21, respectively.

TABLE 7

| Parameter | Units | $CH_4$ | $CO_2$ | $N_2$ |
|---|---|---|---|---|
| Strain at Infinite Pressure, $\epsilon_{\infty i}$ | — | 0.013 | 0.01593 | 0.00774 |
| Pressure at 0.5 Infinite Strain, $p_{\epsilon i}$ | psia | 600 | 550 | 750 |

TABLE 8

| Parameter | Units | FBV 4A: Before $CO_2$ Injection | FBV 4A: After $CO_2$ Injection | FBV 5: Before $N_2$ Injection | FBV 5: During $N_2$ Injection |
|---|---|---|---|---|---|
| Pressure | psia | 1,146 | 1,146 | 1,146 | 1,704 |
| $\phi$ at Pressure | — | 0.002 | 0.00129 | 0.0012 | 0.0027 |
| $\phi/\phi_{atm}$ ratio | — | 0.6095 | 0.3975 | 0.4836 | 1.0790 |
| $\phi_{atm}$ | — | 0.003282 | 0.003249 | 0.002482 | 0.002509 |
| $k_{a\text{-}atm}$ | md | 16.17 | 15.69 | 10.64 | 11.00 |

Figure 5:
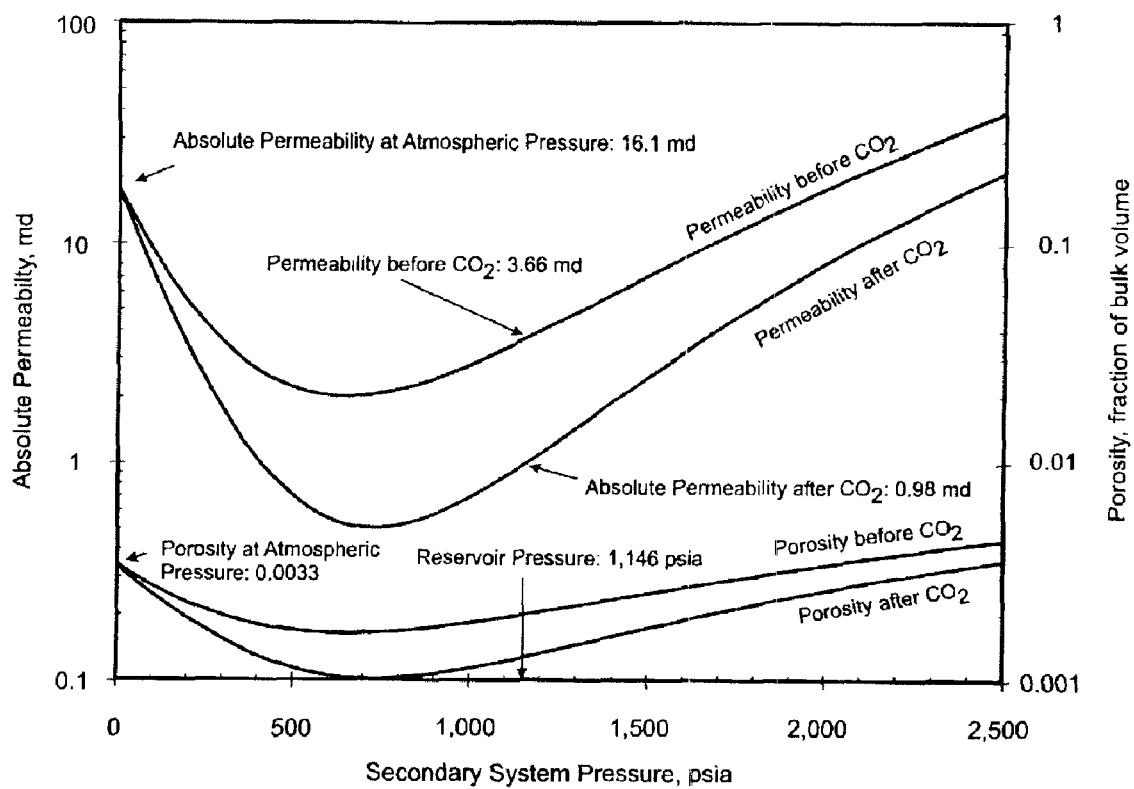
FIG. 5 is a graphical illustration of the relationship between $k_a$ and $\phi$ as a function of SPS pressure for well FBV 4A in Example 1.
Figure 6:
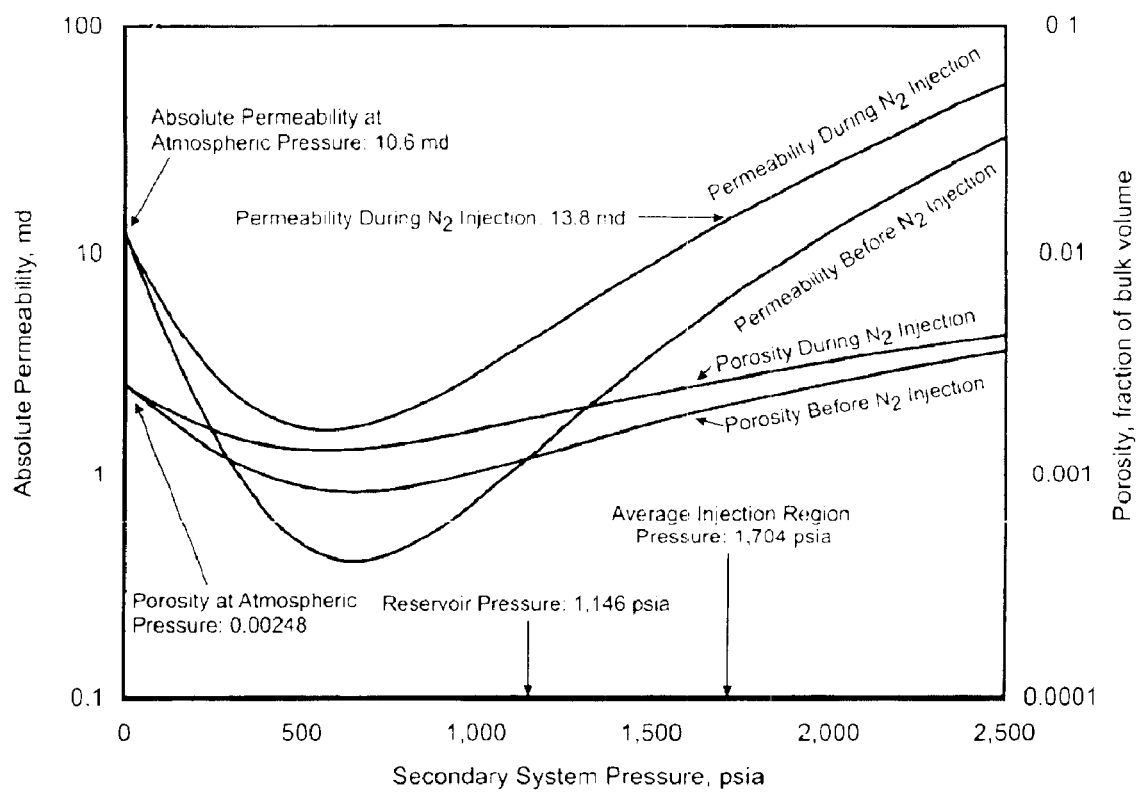
FIG. 6 is a graphical illustration of the relationship between $k_a$ and $\phi$ as a function of SPS pressure for well FBV 5 in Example 1.

Once the $\phi_{atm}$ and $k_{a\text{-}atm}$ estimates were obtained, the values were used in Equations (1) and (2) to determine $\phi$ and $k_a$ values at pressures greater than atmospheric pressure. FIGS. 5 and 6 illustrate the calibrated absolute permeability and porosity estimates for the two FBV 4A and the two FBV 5 gas compositions, respectively. The $\phi_{atm}$ and $k_{a\text{-}atm}$ values were substantially equal for each test condition at atmospheric pressure. However, as pressure increased, the values for $\phi$ and $k_a$ differed for the different fluid compositions due to differing sorption strain relationships. The pressure strain relationship was the same for both SAG and WAG cases as it is independent of gas composition.

Figure 7:
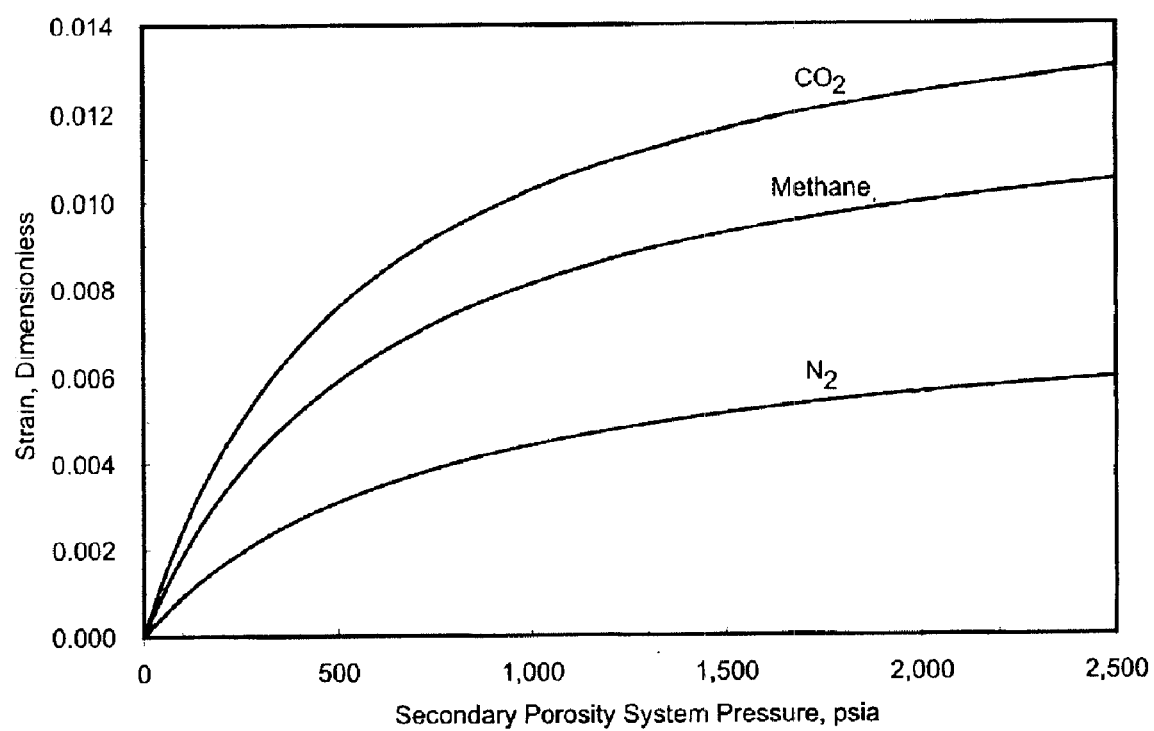
FIG. 7 is a graphical illustration of sorption strain for $CO_2$, $CH_4$ and $N_2$ as a function of SPS pressure for Example 1.

Although the Table 7 values for $\epsilon_{\infty i}$ were similar, there was a dramatic difference between the sorption strain relationships for each gas component. FIG. 7 illustrates these relationships. As expected, the sorption strain magnitude corresponds to the sorptive nature of the gas, i.e. the SAG, $CO_2$, caused the greatest sorption strain, the WAG, $N_2$, caused the least, and $CH_4$ sorption strain was intermediate.

Once the model was calibrated, values for $S_w$ were determined as a function of pressure. First, $S_{w\text{-}atm}$ was determined using Equation (29). Specifically, $S_{w\text{-}atm}$ for FBV 4A was $S_{w\text{-}i}$ (0.60) multiplied by the porosity ratio in Table 8 (0.5463). The resulting estimate of $S_{w\text{-}atm}$ was 0.327. Using the same calculation method, the corresponding $S_{w\text{-}atm}$ value for the FBV 5 data was 0.382.

Once the porosity and absolute permeability at atmospheric pressure were known, the porosity and absolute permeability at other pressures or gas compositions could be computed with Equations (1), (2), (4) and (5). $S_w$ at other pressures and compositions could be computed with Equation (30).

Estimates of the relative permeability to gas and water as a function of pressure were determined by interpolation in Table 2, i.e., $S_w$ dictated $k_{rg}$ and $k_{rw}$. The effective permeability to gas and water were determined as a function of pressure and gas composition by multiplying the absolute permeability by the relative permeability values. FIG. 2 illustrates the relationship between permeability vs. pressure for the FBV 4A gas composition before $CO_2$ injection. FIG. 3 illustrates the water saturation and relative permeability to gas and water vs. pressure for the same composition.

EXAMPLE 2

Example 2 illustrates how the inventors' model can be used to predict injection rates for a desired fluid composition. After the $N_2$ injection test was completed in the FBV 5 well, a simulated flue gas injection test was required. During this test a 50% $CO_2$–50% $N_2$ mixture was planned to be injected at pressures up to 2,500 psia. Accordingly, an estimate of the maximum possible injection rate was required.

From experience, it was known that the in-situ gas composition after injection would not be the same as the injected gas composition because CBM would be desorbed and mixed with the injected gases. Also, SAG would be sorbed in the coal matrix. Therefore, for the purposes of design, the free gas composition after injection was assumed to be approximately 45 mol. % $CH_4$, 45 mol. % $CO_2$, and 10 mol. % $N_2$.

Based on the expected free gas composition, the sorbed gas composition was computed using Equations (17), (18), and (19) to be 16.4 mol. % $CH_4$, 83.0 mol. % $CO_2$, and 0.6 mol. % $N_2$. For this sorbed gas composition, Equations (4) and (5) were used to estimate $\epsilon$ at atmospheric pressure and at 2,000 psia, the pressure within the region affected by injection. These estimates were $3.96(10^{-4})$ and $1.207(10^{-2})$, respectively. The $\epsilon$ values were used in Equation (1) with the $\phi_{atm}$ (0.002482) computed in Example 1 to calculate $\phi/\phi_{atm}$ at 2,000 psia, which was 0.7094. The corresponding $k_a/k_{a\text{-}atm}$ ratio was 0.3571. Then, using the $k_a/k_{a\text{-}atm}$ ratio and $k_{a\text{-}atm}$ (10.64) from Example 1, a value of 3.80 md was calculated for $k_a$ at 2,000 psia.

The $\phi/\phi_{atm}$ ratio was also used in Equation (30) to calculate $S_w$ at 2,000 psia. Specifically, $S_w$ at 2,000 psia was $S_{w\text{-}atm}$ (0.4401) divided by $\phi/\phi_{atm}$ (0.7094), resulting in an estimate of 0.6203. Interpolation in Table 2 above resulted in an estimate for $k_{rg}$ of 0.1352. Therefore, $k_{eg}$ at 2,000 psia during injection was estimated to be about 0.513 md.

The injection rate for the proposed gas composition was then predicted using Equation (33), using the calculated values for $k_{eg}$ (0.513 md). To make the flow rate calculations, additional information was required. The thickness was 13 feet. $T_R$ was 117° F. The skin factor, s, caused by injection was often about $-4$ based upon the inventors' experience. The geometrical term in Equation (27) was 8.07 for a drainage area of 200 acres and a wellbore radius of 0.25 feet. The real gas potential, m(p), at $T_R$ and $P_R$ was calculated using Equation (28), resulting in a value of $7.281(10^7)$ psia$^2$/cp. And, at 2,500 psia and $T_R$, m(p) was $3.179(10^8)$ psia$^2$/cp. Substituting these values into Equation (33) resulted in an estimated injection rate of 489 Mscf/D corresponding to 340 scf/min for injecting the proposed gas mixture at 2,500 psia.

Accordingly, Example 2 illustrated how the inventors' model can be used to predict injection rates for a desired fluid composition.

EXAMPLE 3

This example demonstrates the sensitivity of the inventors' model to rock mechanical properties. Specifically, this example shows the effect of changing values for rock mechanical properties on the $\phi_{atm}$ and $k_{a\text{-}atm}$ values determined in Example 1. As demonstrated below, accuracy in predicting $\phi$ and $k_a$ using the inventors' model is improved with more accurate rock mechanical property values. Accordingly, rock mechanical properties are preferably determined from water injection test data.

As discussed in Example 1, the inventors used data measured during a water injection test to calibrate for M. A value for $\nu$ based on San Juan Basin coal samples (Mavor et al., SPE 39105, ibid) was used to estimate a value for Young's modulus, E. Accordingly, the values used in calibrating the model in Example 1 were 353,210 psi for E, 0.21 for $\nu$, 397,600 for M and 202,994 psi for the bulk modulus, K.

In contrast, Palmer and Mansoori ("P&M," SPE 36737 and SPE 52607, ibid) reported that E can range from 124,000 to 445,000 psi for the San Juan Basin Reservoir. The P&M data value for $\nu$ was 0.39, significantly greater than the Mavor et al. data. The effect of E and $\nu$ on values for M, K, 1/M, and (1-K/M), used in the inventors' model, is compared for Example 1, the upper and lower limits for the P&M E range and the midpoint of the P&M E range.

TABLE 9

| Parameter | Example 1 Values | Palmer & Mansoori Values | | |
|---|---|---|---|---|
| | | Lower Limit | Midpoint | Upper Limit |
| E (psi) | $3.53(10^5)$ | $1.24(10^5)$ | $2.85(10^5)$ | $4.45(10^5)$ |
| $\nu$ (–) | 0.21 | 0.39 | 0.39 | 0.39 |
| M (psi) | $3.98(10^5)$ | $2.47(10^5)$ | $5.68(10^5)$ | $8.88(10^5)$ |
| K (psi) | $2.03(10^5)$ | $1.88(10^5)$ | $4.32(10^5)$ | $6.74(10^5)$ |
| 1/M (psi$^{-1}$) | $2.51(10^{-6})$ | $4.04(10^{-6})$ | $1.76(10^{-6})$ | $1.13(10^{-6})$ |
| 1-K/M (–) | 0.4895 | 0.2404 | 0.2404 | 0.2404 |

The 1/M value in Table 9 is a multiplier in the dynamic pressure strain component of the inventors' model, while the (1-K/M) value is a multiplier in the dynamic sorption strain component of the inventors' model.

The 1/M values for the P&M E range were 1.6 to 0.45 times the 1/M value for Example 1. Accordingly, P&M's E and $\nu$ values affect the dynamic pressure strain component by 1.6 to 0.45 times, as compared to those in Example 1.

And, with respect to the dynamic sorption strain component of the inventors' model, the P&M E and $\nu$ values resulted in a (1-K/M) value about 50% less than the (1-K/M) value for Example 1. This difference causes the $\epsilon_\infty$ value for $CH_4$ and $CO_2$ to be roughly twice those of Example 1. The $\epsilon_{\infty\text{-}N2}$ values and $p_{\epsilon i}$ values for all gases were adjusted as necessary to obtain a match subject to the constraints discussed earlier.

Table 10 compares the $\phi_{atm}$ and $k_{a\text{-}atm}$ values for Example 1 to values obtained using P&M's E and $\nu$ values for their midpoint and upper limit values. It was not possible to obtain reasonable $\phi_{atm}$ and $k_{a\text{-}atm}$ values for P&M's lower or upper limit E value as the $N_2$ injection test could not be matched with ranges of $N_2$ strain parameters that met the inventors' criteria for reasonableness. The $\phi_{atm}$ and $k_{a\text{-}atm}$ values were greater for P&M's midpoint E value and their higher $\nu$ value

TABLE 10

| Parameter | Units | FBV 4A: Before $CO_2$ Injection | FBV 4A: After $CO_2$ Injection | FBV 5: Before $N_2$ Injection | FBV 5: During $N_2$ Injection |
|---|---|---|---|---|---|
| Pressure | psia | 1,146 | 1,146 | 1,146 | 2,262 |
| $\phi$ at Pressure | — | 0.002 | 0.001 | 0.0012 | 0.0027 |
| | | Example 1 Values E = $3.53(10^5)$, $\nu$ = 0.21 | | | |
| $\phi_{atm}$ | — | 0.003282 | 0.003249 | 0.002482 | 0.002509 |
| $k_{a\text{-}atm}$ | md | 16.2 | 15.7 | 10.6 | 11.0 |

TABLE 10-continued

| Parameter | Units | FBV 4A: Before $CO_2$ Injection | FBV 4A: After $CO_2$ Injection | FBV 5: Before $N_2$ Injection | FBV 5: During $N_2$ Injection |
|---|---|---|---|---|---|
| | | Palmer & Mansoori's Midpoint E = 2.85(10⁵), v = 0.39 | | | |
| $\phi_{atm}$ | — | 0.00332 | 0.00330 | 0.00252 | 0.00254 |
| $k_{a\text{-}atm}$ | md | 16.8 | 16.4 | 11.2 | 11.4 |

The range in rock mechanical properties affected the characteristic strain parameters as indicated in Table 11. Use of the E and v values reported by Palmer and Mansoori resulted in $\epsilon_{\infty j}$ values that were substantially greater than those reported by Levine due to the use of the high v value.

TABLE 11

| Parameter | Units | $CH_4$ | $CO_2$ | $N_2$ |
|---|---|---|---|---|
| | | Example 1 | | |
| Strain at Infinite Pressure, $\epsilon_\infty$ | — | 0.013 | 0.0159 | 0.00774 |
| Pressure at 0.5 Infinite Strain, $P_\epsilon$ | psia | 600 | 550 | 750 |
| | Palmer & Mansoori's Midpoint E = 2.85(10⁵), v = 0.39 | | | |
| Strain at Infinite Pressure, $\epsilon_\infty$ | — | 0.02053 | 0.02736 | 0.02040 |

TABLE 11-continued

| Parameter | Units | $CH_4$ | $CO_2$ | $N_2$ |
|---|---|---|---|---|
| Pressure at 0.5 Infinite Strain, $P_\epsilon$ | psia | 600 | 550 | 750 |

This comparison indicates that the estimates of the strain parameters and the rock mechanics properties are highly interrelated. Accordingly, rock mechanical properties are preferably measured as accurately as possible for determining $\phi_{atm}$ and $k_{a\text{-}atm}$.

EXAMPLE 4

The SPS porosity estimate has an impact on the calibration process as evidenced by this example that investigates the calibration results if the SPS porosity before $CO_2$ injection for the FBV 4A well and the SPS porosity before $N_2$ injection for the FBV 5 well were assumed to be half the original estimates.

Reducing the SPS porosity for FBV 5 (before $N_2$ injection) by a factor of two, increases the calibrated M value determined from the FBV 5 water injection test by a factor of two to 795,200 psi. Therefore, based upon a value for v of 0.21, the estimate for E was equal to 706,400 psi.

The use of a smaller SPS porosity value has a substantial effect upon the estimates of $k_{a\text{-}atm}$ as summarized in Table 12. The estimates of $k_{a\text{-}atm}$ are approximately 11 to 18 times greater for the lower SPS porosity case than for Example 1. This comparison demonstrates the benefit of estimating SPS porosity from water production rather than arbitrarily assuming values.

TABLE 12

| Parameter | Units | FBV 4A: Before $CO_2$ Injection | FBV 4A: After $CO_2$ Injection | FBV 5: Before $N_2$ Injection | FBV 5: During $N_2$ Injection |
|---|---|---|---|---|---|
| SPS Pressure | psia | 1,146 | 1,146 | 1,146 | 2,262 |
| $\phi$ at Pressure | — | 0.002 | 0.001 | 0.0012 | 0.0027 |
| | | Example 1 Values E = 3.53(10⁵), v = 0.21 | | | |
| $\phi,$ | — | 0.0020 | 0.001291 | 0.0012 | 0.00207 |
| $\phi_{atm}$ | — | 0.003282 | 0.003249 | 0.002482 | 0.002509 |
| $k_{a\text{-}atm}$ | md | 16.2 | 15.7 | 10.6 | 11.0 |
| | | E = 7.06(10⁵), v = 0.21 with reduced porosity | | | |
| $\phi,$ | — | 0.0010 | 0.000646 | 0.00060 | 0.001353 |
| $\phi_{atm}$ | — | 0.003647 | 0.003628 | 0.003247 | 0.003273 |
| $k_{a\text{-}atm}$ | md | 177.6 | 174.9 | 190.8 | 195.3 |

The reduction in SPS porosity resulted in the same sorption strain parameters as for Example 1 as summarized in Table 11. This comparison indicates that calibration of the rock mechanical properties with water injection test data reduces the potential variation in the sorption strain parameters.

Preferred processes for practicing the invention have been described. It will be understood that the foregoing is illustrative only and that other embodiments of the process can be employed without departing from the true scope of the invention defined in the following claims.

For convenience, the nomenclature used in the Detailed Description and claims is summarized in Table 13.

TABLE 13

| Symbol | Description, Units  SPS = Secondary Porosity System | Equation # |
|---|---|---|
| $\alpha$ | grain thermal expansitivity, $°F.^{-1}$ | 9 |
| $\epsilon$ | total multicomponent volumetric sorption strain at SPS pressure, dimensionless | 1, 5 |
| $\epsilon_{atm}$ | total multicomponent volumetric sorption strain at atmospheric pressure, dimensionless | 1 |
| $\epsilon_{CH4}$ | volumetric sorption strain of $CH_4$, dimensionless | |
| $\epsilon_i$ | volumetric sorption strain for component i in a multicomponent gas, dimensionless | 4, 5 |
| $\epsilon_L$ | volumetric sorption strain at infinite pressure, dimensionless | |
| $\epsilon_{\infty i}$ | characteristic volumetric sorption strain at infinite pressure for component i in a multicomponent gas, dimensionless | 4 |
| $\epsilon_{\infty s}$ | single component characteristic volumetric sorption strain at infinite pressure, dimensionless | 3 |
| $\epsilon_s$ | single component volumetric sorption strain, dimensionless | 3 |
| $\epsilon_{SAG}$ | volumetric sorption strain of SAG, dimensionless | |
| $\epsilon_{WAG}$ | volumetric sorption strain of WAG, dimensionless | |
| $\gamma$ | grain compressibility, $psi^{-1}$ | 9 |
| $\lambda_T$ | total mobility, md/cp | 34 |
| $\mu_g$ | gas viscosity, cp | 24, 28, 34 |
| $\mu_w$ | water viscosity, cp | 24, 34 |
| $\phi$ | SPS porosity at SPS pressure, dimensionless | 1, 2, 29, 30 |
| $\phi_{atm}$ | SPS porosity at atmospheric pressure, dimensionless | 1, 2, 29, 30 |
| $d\phi$ | infinitesimal change in SPS porosity, dimensionless | 9 |
| $\overline{\rho}_c$ | average coal seam density, $g/cm^3$ | 10 |
| $\rho_r$ | rock density, $lbm/ft^3$ | 7 |
| $\sigma$ | total stress, psia | 6 |
| $\sigma_e$ | effective stress, psia | 6, 8 |
| $\sigma'_v$ | vertical stress gradient, psi/ft | 7, 8 |
| $\nu$ | Poisson's ratio, dimensionless | 12, 16 |
| A | area, $ft^2$ | 27 |
| $A_{inj}$ | area of sorbed gas region, $ft^2$ | 10, 11 |
| $a_{i-c}$ | pressure component of sorption strain (i.e., strain contribution factor) for component i under test condition c | 22, 23 |
| $B_g$ | gas formation volume factor, in-situ gas volume/surface gas volume | 24 |
| $B_w$ | water formation volume factor, in-situ water volume/surface water volume | 24 |
| b | poroelastic constant, dimensionless | 6, 8 |
| c | number of tests | |
| $C_A$ | shape factor, dimensionless | 27 |
| E | Young's modulus, psi | 12 |
| f | a fraction ranging from 0 to 1 (Palmer and Mansoori assumed 0.5) | 9 |
| $G_s$ | total gas storage capacity, scf/ton | 10, 18, 19 |
| $G'_{sL}$ | multicomponent Langmuir storage capacity, dry, ash-free basis, scf/ton | |
| $G_{si}$ | storage capacity of component i in a multicomponent gas, in-situ basis, scf/ton | 17, 18, 19 |
| $G_{sLi}$ | Langmuir storage capacity of component i in a multicomponent gas, dry, ash-free basis, scf/ton | 17 |
| h | coal thickness, feet | 10, 25, 33 |
| K | bulk modulus, psi | 1, 9, 16 |
| k | permeability, md | 26 |
| $k_a$ | absolute permeability at SPS pressure, md | 2, 31, 32, 34 |
| $k_{a\text{-}atm}$ | absolute permeability at atmospheric pressure, md | 2 |
| $k_{a\text{-}i}$ | initial absolute permeability, at reservoir pressure, md | |
| $k_{a\text{-}H2O\text{-}inj}$ | absolute permeability at a water injection pressure, md | |
| $k_{a\text{-}WAG\text{-}inj}$ | WAG injection absolute permeability at a WAG injection pressure, md | |
| $k_{a\text{-}SAG\text{-}p}$ | SAG production absolute permeability at a SAG production pressure, md | |
| $k_e$ | effective permeability, md | |
| $k_{eg}$ | effective permeability to gas, md | 24, 25, 32, 33 |
| $k_{eg\text{-}atm}$ | effective permeability to gas at atmospheric pressure, md | |
| $k_{eg\text{-}i}$ | initial effective permeability to gas, md | |
| $k_{eg\text{-}SAG\text{-}p}$ | effective permeability to gas at SAG production pressure, md | |
| $k_{eg\text{-}WAG\text{-}inj}$ | effective permeability to gas at WAG injection pressure, md | |
| $k_{ew}$ | effective permeability to water, md | 24, 32 |
| $k_{ew\text{-}atm}$ | effective permeability to water at atmospheric pressure, md | |
| $k_{ew\text{-}i}$ | initial effective permeability to water, md | |
| $k_{ew\text{-}H2O\text{-}inj}$ | effective permeability to water at water injection pressure, md | |
| $k_{ew\text{-}SAG\text{-}p}$ | effective permeability to water at SAG production pressure, md | |
| $k_{ew\text{-}WAG\text{-}inj}$ | effective permeability to water at WAG injection pressure, md | |
| $k_m$ | modified permeability, md | 26 |
| $k_r$ | relative permeability, dimensionless | |
| $k_{rg}$ | relative permeability to gas, dimensionless | 24, 31, 33 |
| $k_{rg\text{-}atm}$ | relative permeability to gas at the water saturation at atmospheric pressure, dimensionless | |
| $k_{rg\text{-}i}$ | initial relative permeability to gas, dimensionless | |
| $k_{rg\text{-}SAG\text{-}p}$ | relative permeability to gas at SAG production pressure, dimensionless | |
| $k_{rg\text{-}WAG\text{-}inj}$ | relative permeability to gas at WAG injection pressure, dimensionless | |

TABLE 13-continued

| Symbol | Description, Units SPS = Secondary Porosity System | Equation # |
|---|---|---|
| $k_{rw}$ | relative permeability to water, dimensionless | 24, 32, 34 |
| $k_{rw\text{-}atm}$ | relative permeability to water at the water saturation at atmospheric pressure, dimensionless | |
| $k_{rw\text{-}i}$ | initial relative permeability to water, dimensionless | |
| $k_{rw\text{-}H2O\text{-}inj}$ | relative permeability to water at water injection pressure, dimensionless | |
| $k_{rw\text{-}SAG\text{-}p}$ | relative permeability to water at SAG production pressure, dimensionless | |
| $k_{rw\text{-}WAG\text{-}inj}$ | relative permeability to water at WAG injection pressure, dimensionless | |
| n | number of components in multicomponent gas | 4, 5, 17 |
| M | constrained axial modulus, psi | 1, 9, 12, 16 |
| m(p) | real gas potential, psia$^2$/cp | 25, 28, 33 |
| p | SPS pressure, psia | 1, 3, 4, 6, 8, 17, 28 |
| dP | infinitesimal change in SPS pressure, psi | 9 |
| $p_\epsilon$ | characteristic pressure at a strain of $0.5\epsilon_\infty$, psia | |
| $p_{\epsilon s}$ | single component characteristic pressure at a sorption strain of $0.5\epsilon_\infty$, psia | 3 |
| $p_{\epsilon i}, p_{\epsilon j}$ | characteristic pressures at a sorption strain of $0.5\ \epsilon_\infty$, for components i and j, respectively, in a multicomponent gas, psia | 4 |
| $p_{atm}$ | atmospheric pressure, psia | 1 |
| $P_E$ | fracture extension pressure, psia | |
| $P_F$ | fracture pressure, psia | |
| $p_{H2O\text{-}inj}$ | water injection pressure, psia | |
| $p_{Li}, p_{Lj}$ | Langmuir pressures for component i and j, respectively, in a multicomponent gas, psia | 17 |
| $p_{SAG\text{-}p}$ | SAG production pressure, psia | |
| $p_{WAG\text{-}inj}$ | WAG injection pressure, psia | |
| $P_R$ | reservoir pressure, psia | 25 |
| $p_{sc}$ | pressure at standard conditions, 14.69 psia | 25, 33 |
| $P_w$ | bottom-hole pressure, psia | 25 |
| $q_g$ | gas production rate at standard conditions, Mscf/D | 24, 25, 33 |
| $q_w$ | water production rate, STB/D | 24 |
| $r_d$ | equivalent steady-stage drainage radius, feet | 25, 27, 33 |
| $r_{inj}$ | gas penetration distance from the wellbore for circular injection area, feet | 10 |
| $r_m$ | modified region radius, feet | 26 |
| $r_w$ | wellbore radius, feet | 25, 26, 27, 33 |
| S | skin factor, dimensionless | 25, 26, 33 |
| $S_w$ | water saturation, dimensionless | 30 |
| $S_{w\text{-}atm}$ | water saturation at atmospheric pressure, dimensionless | 29, 30 |
| $S_{w\text{-}i}$ | initial water saturation, dimensionless | 29 |
| $S_{w\text{-}SAG\text{-}p}$ | water saturation at SAG production pressure, dimensionless | |
| $S_{w\text{-}WAG\text{-}inj}$ | water saturation at WAG injection pressure, dimensionless | |
| $T_R$ | reservoir temperature, ° R | 25, 33 |
| $dT_R$ | infinitesimal change in reservoir temperature, ° R | 9 |
| $T_{sc}$ | temperature at standard conditions, 519.67° R (60° F.) | 25, 33 |
| $t_s$ | sorption time, days | |
| $t_{s\text{-}CBM}$ | sorption time for original in-situ CBM at reservoir temperature, days | |
| $t_{s\text{-}SAG}$ | sorption time for SAG at reservoir temperature, days | |
| $V_{inj}$ | volume of injected gas, scf | 10 |
| $V_p$ | pore volume, ft$^3$ | |
| $V_w$ | water volume in SPS, ft$^3$ | |
| $w_a$ | ash content, weight fraction | 17 |
| $w_{we}$ | equilibrium moisture content, weight fraction | 17 |
| $x_i, x_j$ | mole fractions of component i and j, respectively, in the sorbed gas phase, dimensionless | 4, 19 |
| $y_i, y_j$ | mole fractions of component i and j, respectively, in the free gas phase, dimensionless | 17 |
| z | depth, feet | 7, 8 |
| dz | infinitesimal change in depth, feet | 7 |
| $z_g$ | real gas deviation factor, dimensionless | 28 |

We claim:

1. A method for producing a calculated secondary porosity system (SPS) porosity value for a coal bed, comprising:

(a) determining an initial condition in the coal bed, including an initial (SPS) pressure and an initial sorbed gas composition having an initial methane content;

(b) determining a pressure strain effect on the coal bed due to increasing the SPS pressure to a value greater than the initial SPS pressure;

(c) determining a sorption strain effect on the coal bed due to changes in the sorbed gas composition resulting from decreasing the methane content and increasing the content of a stronger adsorbing fluid (SAG) relative to the initial sorbed gas composition;

(d) selecting a reference SPS pressure and a reference sorbed gas composition;

(e) correlating the initial condition, the pressure strain effect and the sorption strain effect in a quantitative relationship to determine:

(i) a reference SPS porosity, (ii) a reference absolute permeability, and (iii) reference characteristic sorption strain parameters for at least methane and the SAG, for the reference SPS pressure and reference sorbed gas composition; and (f) producing the calculated SPS porosity value for a pre-selected SPS pressure and a pre-selected sorbed gas composition, using the quantitative relationship and reference values determined in part (e).

2. The method of claim 1, wherein the quantitative relationship includes a SPS porosity that is substantially equal to the reference SPS porosity plus the pressure strain effect plus the sorption strain effect.

3. The method of claim 2, wherein the quantitative relationship is:

$$\frac{\phi}{\phi_{ref}} = 1 + \frac{(p - p_{ref})}{\phi_{ref} M} + \frac{1}{\phi_{ref}}\left(1 - \frac{K}{M}\right)(\varepsilon_{ref} - \varepsilon)$$

$$\frac{k_a}{k_{a\text{-}ref}} = \left(\frac{\phi}{\phi_{ref}}\right)^3$$

where $\phi$ SPS porosity at SPS pressure p, dimensionless $\phi_{ref}$ SPS porosity at reference SPS pressure and reference sorbed gas composition, dimensionless $p_{ref}$ reference pressure, psia p SPS pressure, psia M constrained axial modulus, psi $\varepsilon$ total multicomponent volumetric sorption strain at SPS pressure p, dimensionless $\varepsilon_{ref}$ total multicomponent volumetric sorption strain at reference SPS pressure and reference sorbed gas composition, dimensionless K bulk modulus, psi $k_a$ absolute permeability at SPS pressure p, md $k_{a\text{-}ref}$ absolute permeability at reference SPS pressure and reference sorbed gas composition, md.

4. The method of claim 1, wherein the reference SPS pressure is atmospheric pressure and the reference sorbed gas composition has 0% methane and 0% SAG.

5. The method of claim 1, further comprising calculating the absolute permeability for the calculated SPS porosity value, using the quantitative relationship and the reference values determined in part (e).

6. A method for producing a calculated secondary porosity system (SPS) porosity value for a coal bed having an in-situ sorbed gas composition, the method comprising:

obtaining test results from at least three independent field tests, $c_1$, $c_2$ and $C_3$, on the coal bed comprising an initial-condition field test, an injection field test using an injection fluid selected from the group consisting of water and a weaker adsorbing fluid (WAG), and a production field test using a stronger adsorbing fluid (SAG), where the test results from $c_1$, $c_2$ and $c_3$ each independently include at least:

a field test SPS pressure, a field test absolute permeability, and a field test sorbed gas composition, so that the test results from each of $c_1$, $c_2$ and $c_3$ can be correlated in a quantitative relationship to determine:

(i) a reference SPS porosity, (ii) a reference absolute permeability, and (iii) reference characteristic sorption strain parameters for at least methane and a SAG, for a reference SPS pressure and a reference sorbed gas composition; and thereby allowing the calculated SPS porosity value to be produced for a pre-selected SPS pressure and a pre-selected sorbed gas composition, using the quantitative relationship and the reference values of (i), (ii) and (iii).

7. The method of claim 6, wherein the injection fluid is water.

8. The method of claim 7, further comprising obtaining test results from a second injection field test using WAG as the injection fluid.

9. The method of claim 6, wherein one or both of the pre-selected SPS pressure and pre-selected sorbed gas composition is different from each of the field test SPS pressures and each of the field test sorbed gas compositions, for $c_1$, $c_2$ and $c_3$ respectively.

10. The method of claim 6, wherein the quantitative relationship includes a SPS porosity that is substantially equal to the reference SPS porosity plus a dynamic pressure strain component plus a dynamic multicomponent sorption strain component.

11. The method of claim 6, wherein the number of field tests is at least (n+1), where n is the number of major components in a pre-selected sorbed gas composition.

12. The method of claim 10, wherein the quantitative relationship is:

$$\frac{\phi}{\phi_{ref}} = 1 + \frac{(p - p_{ref})}{\phi_{ref} M} + \frac{1}{\phi_{ref}}\left(1 - \frac{K}{M}\right)(\varepsilon_{ref} - \varepsilon)$$

$$\frac{k_a}{k_{a\text{-}ref}} = \left(\frac{\phi}{\phi_{ref}}\right)^3$$

where $\phi$ SPS porosity at SPS pressure p, dimensionless $\phi_{ref}$ SPS porosity at reference SPS pressure and reference sorbed gas composition, dimensionless $p_{ref}$ reference SPS pressure, psia p SPS pressure, psia M constrained axial modulus, psi $\varepsilon$ total multicomponent volumetric sorption strain at SPS pressure p, dimensionless $\varepsilon_{ref}$ total multicomponent volumetric sorption strain at reference SPS pressure and reference sorbed gas composition, dimensionless K bulk modulus, psi $k_a$ absolute permeability at SPS pressure p, md $k_{a\text{-}ref}$ absolute permeability at reference SPS pressure and reference sorbed gas composition, md.

13. The method of claim 6, wherein the reference SPS pressure is atmospheric pressure and the reference sorbed gas composition has 0% methane and 0% SAG.

14. The method of claim 6, further comprising calculating the absolute permeability for the calculated SPS porosity value, using the quantitative relationship and the reference values of (i), (ii) and (iii).

15. A method for producing a calculated secondary porosity system (SPS) porosity value for a coal bed, comprising:

(a) determining, from the data of test 1, an initial absolute permeability, $k_{a\text{-}1}$, at an initial SPS pressure, $p_1$, and a test 1 free gas composition;

(b) determining, from the data of test 2 comprising injecting an injection fluid selected from the group consisting of water and a weaker adsorbing fluid (WAG) into the coal bed, an injection absolute permeability, $k_{a-2}$, at an injection SPS pressure, $p_2$, and a test 2 free gas composition;

(c) determining, from the data of test 3 comprising injecting a stronger adsorbing fluid (SAG) into the coal bed, and producing gas from the coal bed, SAG production absolute permeability, $k_{a-3}$, at a SAG production SPS pressure, $p_3$, and a test 3 free gas composition;

(d) determining a sorbed gas composition corresponding to each of the free gas compositions for each test in parts (a), (b) and (c);

(e) producing values for total multicomponent volumetric sorption strain, $\epsilon_1$, $\epsilon_2$, and $\epsilon_3$, and total multicomponent volumetric sorption strain at atmospheric pressure, $\epsilon_{atm-1}$, $\epsilon_{atm-2}$, and $\epsilon_{atm-3}$, for each sorbed gas composition in part (d);

(f) solving Equations (1) and (2) for
  (i) SPS porosity at atmospheric pressure, $\phi_{atm}$,
  (ii) an absolute permeability at atmospheric pressure, $k_{a-atm}$, and
  (iii) characteristic sorption strain parameters, for a reference pressure=atmospheric pressure, $p_{atm}$, at which pressure, there is a substantially negligible sorbed gas composition effect on $\phi_{atm}$, $\phi_{a-atm}$, and characteristic sorption strain parameters, using SPS pressures $p_1$, $p_2$ and $p_3$, absolute permeability values $k_{a-1}$, $k_{a-2}$ and $k_{a-3}$ and total multicomponent volumetric sorption strain, $\epsilon_1$, $\epsilon_{atm-1}$, $\epsilon_2$, $\epsilon_{atm-2}$, $\epsilon_3$, and $\epsilon_{atm-3}$, from part (e):

$$\frac{\phi_c}{\phi_{atm}} = 1 + \frac{(p_c - p_{atm})}{\phi_{atm} M} + \frac{1}{\phi_{atm}}\left(1 - \frac{K}{M}\right)(\varepsilon_{atm-c} - \varepsilon_c) \quad (1)$$

$$\frac{k_{a-c}}{k_{a-atm}} = \left(\frac{\phi_c}{\phi_{atm}}\right)^3 \quad (2)$$

where
  $\phi_c$ SPS porosity at SPS pressure $p_c$, dimensionless
  $\phi_{atm}$ SPS porosity at atmospheric pressure, dimensionless
  $p_{atm}$ atmospheric pressure, psia
  $p_c$ SPS pressure, psia
  M constrained axial modulus, psi
  $\epsilon_c$ total multicomponent volumetric sorption strain at SPS pressure $p_c$, dimensionless
  $\epsilon_{atm-c}$ total multicomponent volumetric sorption strain at atmospheric pressure, dimensionless
  K bulk modulus, psi
  c test number 1, 2, 3, ... c
  $k_{a-c}$ absolute permeability at SPS pressure $p_c$, md
  $k_{a-atm}$ absolute permeability at atmospheric pressure, md (g) producing the calculated SPS porosity value for a pre-selected SPS pressure and a pre-selected sorbed gas composition, using Equation (1) and $\phi_{atm}$, $k_{a-atm}$ and the characteristic sorption strain parameters determined in part (f).

16. The method of claim 15, further comprising calculating the absolute permeability for the calculated SPS porosity value using Equation (2) and the values for $\phi_{atm}$, $k_{a-atm}$ and the characteristic sorption strain parameters determined in part (f).

17. The method of claim 15, wherein the fluid injected in test 2 is water and the water injection free gas composition is the same as the initial free gas composition.

18. The method of claim 17, further comprising repeating part (b) for a test using WAG as the injection fluid.

19. The method of claim 18, further comprising repeating part (b) for a test using a different WAG as the injection fluid.

20. The method of claim 15, wherein the fluid injected in test 2 is WAG and the WAG injection free gas composition is determined by producing gas from the coal bed after injecting WAG.

21. The method of claim 20, further comprising determining, from the results of test 4, a WAG production absolute permeability, $k_{a-4}$, at a WAG production SPS pressure, $p_4$, and WAG production free gas composition, and performing parts (d) through (f) for the results of test 4.

22. The method of claim 15, further comprising determining, from the result of test 5, a SAG injection absolute permeability, $k_{a-5}$, at a SAG injection SPS pressure, $p_5$, and a SAG injection free gas composition, and performing parts (d) through (f) for the results of test 5.

23. The method of claim 15, further comprising repeating part (c) for test using a different SAG.

24. The method of claim 15, wherein the number of field tests is at least (n+1), where n is the number of major components in a pre-selected sorbed gas composition.

25. The method of claim 15, wherein (f) includes providing an initial value for a first $\phi_{c1}$ for one of the tests 1, 2 or 3, having an absolute permeability $k_{a-c1}$, and determining a second $\phi_{c2}$ for another of the tests 1, 2 or 3, having an absolute permeability $k_{a-c2}$, according to:

$$\phi_{c2} = \phi_{c1}\left(\frac{k_{a-c2}}{k_{a-c1}}\right)^{\frac{1}{3}}.$$

26. The method of claim 25, wherein part (f) further includes determining a total multicomponent volumetric sorption strain difference, $(\epsilon_{c1} - \epsilon_{c2})$, for $\phi_{c1}$ and $\phi_{c2}$ at their respective SPS pressures, $p_{c1}$ and $p_{c2}$, according to:

$$\varepsilon_{c1} - \varepsilon_{c2} = \frac{\phi_{c2} - \phi_{c1} + \frac{p_{c1} - p_{c2}}{M}}{1 - \frac{K}{M}}.$$

27. The method of claim 26, wherein part (f) further includes determining characteristic sorption strain parameters from the total multicomponent volumetric sorption strain difference.

28. The method of claim 15, wherein Equation (1) further comprises a temperature strain component.

29. The method of claim 15, wherein parts (b) and (c) are performed using test results obtained from injecting the injection fluid in part (b) and the SAG into the same well.

30. The method of claim 15, wherein parts (b) and (c) are performed using test results obtained from injecting the injection fluid in part (b) into a first well and injecting the SAG into a second well.

31. The method of claim 15, further comprising determining water saturation at atmospheric pressure, $S_{w-atm}$, according to equation (30) after a value for $\phi_{atm}$ is determined in part (f):

$$S_w = \frac{S_{w-atm}}{\frac{\phi}{\phi_{atm}}} \quad (30)$$

where
  $S_w$ water saturation, dimensionless
  $S_{w-atm}$ water saturation at atmospheric pressure, dimensionless.

32. A well-test procedure for producing a calculated secondary porosity system (SPS) porosity value for a coal bed, the coal bed having at least one injection means comprising a wellbore and at least one producing means that can communicate with at least a portion of the coal bed, comprising:

(a) obtaining a $1^{st}$ data set
    so that an initial absolute permeability, $k_{a-1}$, of a coal bed can be determined for an initial SPS pressure and an initial free gas composition;

(b) injecting a first injection fluid into the at least one injection means at a pressure greater than the initial SPS pressure and obtaining a $2^{nd}$ data set
    so that an injection absolute permeability, $k_{a-2}$, can be determined for an injection SPS pressure, $p_2$;

(c) shutting in the at least one injection means;

(d) injecting a second injection fluid having a different sorption capacity than the first injection fluid into the at least one injection means at a pressure greater than the initial SPS pressure;

(e) shutting in the at least one injection means;

(f) producing fluid from the coal bed through the at least one producing means and obtaining a $3^{rd}$ data set
    so that a production absolute permeability, $k_{a-3}$, can be determined for a production SPS pressure, $p_3$; and (g) obtaining a $4^{th}$ data set of production data for the fluid produced in part (f), wherein at least the first injection fluid and the second injection fluid recited in parts (b) and (d) are independently selected from the group consisting of the following first injection fluid/second injection fluid combinations:

(i) WAG/SAG,
(ii) SAG/WAG,
(iii) water/SAG, and
(iv) SAG/water, wherein a WAG is a fluid comprising at least about 70% (by vol.) of a weaker adsorbing fluid and a SAG is a fluid comprising at least about 70% (by vol.) of a stronger adsorbing fluid,
so that the $1^{st}$, $2^{nd}$, $3^{rd}$, and $4^{th}$ data sets can be correlated in a quantitative relationship to determine the coal bed's (i) reference SPS porosity,
(ii) reference absolute permeability, and
(iii) reference characteristic sorption strain parameters for at least methane and SAG, for a reference SPS pressure and a reference sorbed gas composition; and
thereby allowing the calculated SPS porosity value to be produced for a pre-selected SPS pressure and a pre-selected sorbed gas composition.

33. The well-test procedure of claim 32, wherein the reference SPS pressure is atmospheric pressure and $\phi_{atm}$ is determined by solving Equations (1) and (2):

$$\frac{\phi}{\phi_{atm}} = 1 + \frac{(p - p_{atm})}{\phi_{atm} M} + \frac{1}{\phi_{atm}}\left(1 - \frac{K}{M}\right)(\varepsilon_{atm} - \varepsilon) \quad (1)$$

$$\frac{k_a}{k_{a-atm}} = \left(\frac{\phi}{\phi_{atm}}\right)^3 \quad (2)$$

where $\phi$ SPS porosity at SPS pressure p, dimensionless
$\phi_{atm}$ SPS porosity at atmospheric pressure, dimensionless
$p_{atm}$ atmospheric pressure, psia
p SPS pressure, psia
M constrained axial modulus, psi
$\varepsilon$ total multicomponent volumetric sorption strain at SPS pressure p, dimensionless
$\varepsilon_{atm}$ total multicomponent volumetric sorption strain at atmospheric pressure, dimensionless
K bulk modulus, psi
$k_a$ absolute permeability at SPS pressure, md
$k_{a-atm}$ absolute permeability at atmospheric pressure, md.

34. The well-test procedure of claim 33, wherein Equation (1) further comprises a temperature strain component.

35. The well-test procedure of claim 32, wherein the first injection fluid/second injection fluid combination is selected from the group consisting of (i) WAG/SAG and (iii) water/SAG.

36. The well-test procedure of claim 35, wherein part (c) further comprises producing fluid from the coal bed through the at least one producing means; and obtaining production data for the produced fluid.

37. The well-test procedure of claim 32, wherein the first injection fluid/second injection fluid combination is (iii), water/SAG.

38. The well-test procedure of claim 37, wherein part (b) further comprises, after injecting water, injecting WAG into the at least one injection means at a pressure greater than the initial SPS pressure and determining a second injection absolute permeability, $k_{a-2a}$, at a second injection SPS pressure, $p_{2a}$; shutting in the at least one injection means; producing fluid from the coal bed through the at least one producing means; and obtaining production data for the produced fluid.

39. The well-test procedure of claim 32, wherein the WAG is selected from the group consisting of helium, hydrogen, nitrogen, carbon monoxide, argon, and oxygen.

40. The well-test procedure of claim 32, further comprising repeating parts (b) and (c) for a different WAG.

41. The well-test procedure of claim 32, wherein the production data is selected from the group consisting of coal thickness, bottom-hole temperature, bottom-hole pressure, surface pressure, surface temperature, fluid production rate, free gas composition and sorbed gas composition.

42. The well-test procedure of claim 32, wherein the number of field tests is at least (n+1), where n is the number of major components in a pre-selected sorbed gas composition.

43. The well-test procedure of claim 32, wherein the SAG is selected from the group consisting of carbon dioxide, nitric oxide, sulfur hexafluoride, hydrogen sulfide, sulfur dioxide, nitrogen dioxide, sulfur trioxide, trichlorofluoromethane, dichlorodifluoromethane, chlorotrifluoromethane, tetrafluoromethane, dichloromonofluoromethane, fluoroform, 1,1,2-trichloro-1,2,2-trifluoroethane, dichlorotetrafluoroethane, hexafluoroethane, chloropentafluoroethane, and combinations thereof.

44. The well-test procedure of claim 32, further comprising repeating parts (d) through (g) for a different SAG.

45. The well-test procedure of claim 33, further comprising conducting a water injection test after part (g) for determining effect of the second injection fluid on M and K in equation (1).

46. The well-test procedure of claim 32, wherein the shut-in time in part (c) is in a range from about $0.5t_{s-CBM}$ to about $4t_{s-CBM}$.

47. The well-test procedure of claim 32, wherein the shut-in time in part (c) is in a range from about $t_{s-CBM}$ to about $2t_{s-CBM}$.

48. The well-test procedure of claim 32, wherein the shut-in time in part (e) is in a range from about $0.5t_{S\text{-}CBM}$ to about $4t_{S\text{-}CBM}$.

49. The well-test procedure of claim 32, wherein the shut-in time in part (e) is in a range from about $t_{S\text{-}CBM}$ to about $2t_{S\text{-}CBM}$.

50. The well-test procedure of claim 32, wherein the shut-in time in part (c) is in the range from about the injection time to 1.5 times the injection time.

51. The well-test procedure of claim 32, wherein the shut-in time in part (e) is in the range from about the injection time to 1.5 times the injection time.

52. The well-test procedure of claim 38, wherein WAG is injected for a time in a range from about 6 hours to about 30 days.

53. The well-test procedure of claim 37, wherein water is injected for a time in a range from about 2 hours to about 24 hours.

54. The well-test procedure of claim 32, wherein SAG is injected for a time in a range from about 6 hours to about 30 days.

55. The method of claim 6, further comprising obtaining, based on the calculated SPS porosity value, at least one value selected from the group consisting of:

absolute permeability, relative permeability, effective permeability, water saturation, injection pressure, injection rate, injected fluid composition, produced fluid composition, gas flow rate, and water flow rate.

56. The method of claim 55, wherein the calculated SPS porosity value is used in a process selected from the group consisting of:

fluid production from the coal bed, fluid sequestration in the coal bed and combinations thereof.

57. The well-test procedure of claim 32, further comprising obtaining, based on the calculated SPS porosity value, at least one value selected from the group consisting of:

absolute permeability, relative permeability, effective permeability, water saturation, injection pressure, injection rate, injected fluid composition, produced fluid composition, gas flow rate, and water flow rate.

58. The well-test procedure of claim 57, wherein the calculated SPS porosity value is used in a process selected from the group consisting of:

fluid production from the coal bed, fluid sequestration in the coal bed and combinations thereof.

59. A use comprising:

(i) obtaining the calculated SPS porosity value produced by claim 1, part (f), and (ii) using the calculated SPS porosity value for determining at least one value selected from the group consisting of:

absolute permeability, relative permeability, effective permeability, water saturation, injection pressure, injection rate, injected fluid composition, produced fluid composition, gas flow rate in the coal bed, and water flow rate in the coal bed;

in a process selected from the group consisting of:

fluid production from the coal bed, fluid sequestration in the coal bed and combinations thereof.

60. A use comprising:

(i) obtaining the calculated SPS porosity value produced by claim 15, part (g), and (ii) using the calculated SPS porosity value for determining at least one value selected from the group consisting of:

absolute permeability, relative permeability, effective permeability, water saturation, injection pressure, injection rate, injected fluid composition, produced fluid composition, gas flow rate in the coal bed, and water flow rate in the coal bed;

in a process selected from the group consisting of:

fluid production from the coal bed, fluid sequestration in the coal bed and combinations thereof.

* * * * *